United States Patent [19]

Thomas et al.

[11] Patent Number: 4,465,848
[45] Date of Patent: Aug. 14, 1984

[54] SPECTINOMYCIN COMPOUNDS

[75] Inventors: Richard C. Thomas, Oshtemo Township, Kalamazoo County; Edward L. Fritzen, Kalamazoo, both of Mich.

[73] Assignee: The Upjohn Company, Kalamazoo, Mich.

[21] Appl. No.: 417,313

[22] Filed: Sep. 13, 1982

Related U.S. Application Data

[63] Continuation-in-part of Ser. No. 314,261, Oct. 23, 1981, abandoned.

[51] Int. Cl.$^3$ .................. C07D 319/20; C07D 309/10
[52] U.S. Cl. .................................... 549/361; 549/417; 549/332; 548/526; 546/270; 546/256; 544/378; 544/372; 544/365; 544/360; 544/357; 544/148; 544/141; 544/124; 544/121; 424/283; 424/274; 424/263; 424/250
[58] Field of Search ...................... 549/417, 361, 332; 548/526; 546/270, 256; 544/357, 378, 148, 121, 124, 141, 360, 365, 372

[56] References Cited

U.S. PATENT DOCUMENTS

| | | | |
|---|---|---|---|
| 3,147,277 | 9/1964 | Hoeksema | 549/361 |
| 3,184,478 | 5/1965 | Birkenmeyer et al. | 549/361 |
| 3,207,764 | 9/1965 | Hoeksema et al. | 549/361 |
| 3,234,092 | 2/1966 | Bergy et al. | 167/65 |
| 3,427,321 | 2/1969 | Hoeksema et al. | 549/361 |
| 4,173,647 | 11/1979 | Maier et al. | 424/283 |
| 4,282,152 | 8/1981 | White | 549/361 |
| 4,351,771 | 9/1982 | White et al. | 549/361 |

FOREIGN PATENT DOCUMENTS 2756912 5/1979 Fed. Rep. of Germany.
2756913 5/1979 Fed. Rep. of Germany.

OTHER PUBLICATIONS

Boissonnas, R. A., Selectively Removable Amino Protective Groups Used in the Synthesis of Peptides, Adv. Org. Chem. 3:159-190 (1963).
Grewe et al., Abbau der Chinasaure nach Hunsdiecker, Chem. Ber. 98:104-110 (1965).
Hanessian, S., et al., Synthesis of 4-Amino-4-(S)-Dihydrospectinomycin, J. Antibiotics 34:350-352 (1981).
House, H. O., et al., Preparation and Decomposition of Unsaturated Esters of Diazonacetic Acid, J. Org. Chem. 33:53-60 (1968).
Knight, J. C., et al., Reduction Products of Spectinomycin, J. Antibiotics 28:136-138 (1975).
Maier, R., et al., Modification of Spectinomycin 1. Synthesis of 4-Amino-Spectinomycins, J. Antibiotics 34:16-21 (1981).
Mathieu, et al., "Formation of C-C Bonds," G. Thieme Publ., Stuttgart, W. Germany, vol. I, pp. 429-440 (1973).
Wiley, P. F., et al., The Chemistry of Actinospectacin, IV. J. Amer. Chem. Soc., 85:2652-2659 (1963).
Windholz, T. B., et al., Trichloroethoxycarbonyl: A Generally Applicable Protecting Group, Tetrahedron Letters, 27:2555-2557 (1967).
Woitun, E., et al., Modification of Spectinomycin. 2. Derivatives of 4-Dihydro-4-Deoxy-4(R)-Aminospectinomycin, J. Antibiotics 34:22-27 (1981).

*Primary Examiner*—Nicky Chan
*Attorney, Agent, or Firm*—L. Ruth Hattan

[57] ABSTRACT

The present specification provides novel antimicrobial analogs of spectinomycin and intermediates and processes for their preparation. Particularly described are novel 3'-diazo-secospectinomycin derivatives useful in the preparation of a variety of 3'-substituted spectinomycin analogs.

6 Claims, No Drawings

SPECTINOMYCIN COMPOUNDS

DESCRIPTION

CROSS REFERENCE TO RELATED APPLICATION

This application is a continuation-in-part application of Ser. No. 314,261, filed Oct. 23, 1981, now abandoned.

TECHNICAL BACKGROUND

1. Field of the Invention

The present invention relates to novel compounds and processes. In particular, the invention relates to novel analogs of the aminocyclitol antibiotic spectinomycin and novel processes and intermediates for synthesizing these novel analogs.

The novel analogs of spectinomycin disclosed herein are useful as antimicrobial agents and the novel intermediates are useful in synthetic processes for making the novel antimicrobial analogs.

Spectinomycin is the compound illustrated, with numbering of carbon positions, in formula XX.

The present invention relates to novel C-3′ analogs of
(i) spectinomycin (formula XX),
(ii) C-6′ analogs of spectinomycin, including the 5′-desmethyl analog, of spectinomycin illustrated in formula XXI wherein $R_3$ is:
  (a) hydrogen
  (b) alkyl of 2 to 8 carbon atoms, inclusive,
  (c) —$R_{31}$—O—$R_{32}$, wherein $R_{31}$ is alkylene of 1 to 4 carbon atoms, inclusive, and $R_{32}$ is hydrogen or alkyl of 1 to 6 carbon atoms, inclusive, with the proviso that the sum of the number of carbon atoms in $R_{31}$ and the number of carbon atoms in $R_{32}$ is less than or equal to 7,
  (d) —$R_{31}$—$NR_{33}R_{34}$, wherein $R_{31}$ is as defined above, wherein $R_{33}$ is hydrogen or alkyl of 1 to 6 carbon atoms, inclusive, and wherein $R_{34}$ is hydrogen, alkyl of 1 to 6 carbon atoms, inclusive, or a blocking group with the proviso that when $R_{34}$ is not a blocking group, the sum of (a) the number of carbon atoms in $R_{31}$ and (b) the number of carbon atoms in whichever of $R_{33}$ or $R_{34}$ has the larger number of carbon atoms is less than or equal to 7, or
  (e) alkyl of 1 to 4 carbon atoms, inclusive, substituted with 1, 2, or 3 halogen atoms,
(iii) analogs of spectinomycin (formula XX) and C-6′ analogs thereof (formula XXI) in which the hydrogen atom attached to each of the nitrogen atoms bonded to C-1 and C-3 in the molecules are replaced by a blocking group.

Unless otherwise qualified, reference herein to a C-3′ analog or C-3′ analogs of spectinomycin includes reference to the aforementioned analogs with the nitrogen atoms bonded to C-1 and C-3 blocked and to analogs of formula XXI (including analogs of formula XXI with nitrogen atoms bonded to C-1 and C-3 blocked).

Blocking groups as referred to above are sometimes called "protective groups" in the art and are well known in many fields of organic chemistry, including peptide chemistry, fatty acid chemistry and especially semi-synthetic and synthetic antibiotic chemistry. Two commonly used blocking groups are carbobenzyloxy and t-butoxycarbonyl. Such groups can be removed easily and replaced by hydrogen atoms with suitable treatments, which may vary in detail depending on the particular blocking group and the particular molecule to which it is bonded, with acids or by reduction. A quite comprehensive list of blocking groups which can be attached to spectinomycin analogs is disclosed in U.S. Pat. No. 4,173,647, the selection, preparation, use and hydrolysis of which is incorporated herein by reference. Regarding the chemistry of adding and removing such blocking groups, see, e.g., Biossonnas, Adv. Org. Chem. 3, 159 (1963) and Windholz, et al., Tetrahedron Lett., 8, 2555 (1967).

Spectinomycin itself is a known natural product. Bergy, et al., U.S. Pat. No. 3,234,092. Numerous spectinomycin analogs in which the nitrogen atom bonded to C-1 and C-3 are blocked are also known. Maier, et al., U.S. Pat. No. 4,173,647; Federal Republic of Germany Offenlegungschriften Nos. 2,756,912 (Derwent Farmdoc Accession No. 50959B) and 2,756,913 (Derwent Farmdoc Accession No. 50960B).

Numerous C-6′ analogs, including the 5′-desmethyl, of spectinomycin as well as such analogs with nitrogen atoms bonded to C-1 and C-3 blocked, are known. U.S. patent application Ser. No. 150,530, filed May 16, 1980 now U.S. Pat. No. 4,351,771.

The present invention also concerns novel synthetic processes. In particular, it concerns:
(i) the novel, base-catalyzed synthesis of novel 3′-deoxo-3′-diazo analogs of spectinomycin from known 3′-deoxo-3′-arylsulfonylhydrazone analogs of spectinomycin;
(ii) the novel synthesis of novel 3′-deoxo-3′-(N,N′-dialkyl)-enamino-analogs of spectinomycin from novel 3′-deoxo-3′-diazo analogs thereof and (N,N-dialkyl)methyleneammonium halides in the presence of base in dry acetonitrile or other lower-alkyl-cyanide solvents;
(iii) the novel synthesis of both 3′-(R)-spectinomycin cyanohydrins and 3′-(S)-spectinomycin cyanohydrins from the corresponding spectinomycins themselves (with keto-oxygen at C-3′) and a source of cyano groups (e.g., hydrogen cyanide or acetone cyanohydrin) in the presence of base or basic ion exchange resin; and
(iv) the novel synthesis of 3′-(S)-spectinomycin cyanohydrins from the corresponding 3′-(R)-spectinomycin cyanohydrins in the presence of base or basic ion exchange resin.

With respect to novel process (iii), either epimer can be synthesized in excess of the other, depending on reaction conditions (especially reaction time, the base or basic ion-exchange resin used, and the concentration or amount thereof in the reaction mixture) as described in greater detail below. Base catalyzes both hydrocyanation and isomerization at C-3′ in novel process (iii).

All of the analogs of the present invention which contain one or more blocking groups, and all of the analogs which contain a diazo group at C-3′ are useful intermediates in processes for making C-3′ analogs of spectinomycin which are useful as antimicrobial agents.

The present invention also includes the pharmacologically acceptable acid addition salts of the novel antimicrobial C-3′ analogs of spectinomycin disclosed herein.

Similar to the known antimicrobial spectinomycin and C-6′ spectinomycin-analog precursors, the novel C-3′ spectinomycin analogs of the present invention, useful as antimicrobial agents, are either microbistatic or microbicidal. The novel antimicrobial C-3′ spectinomycin analogs within the scope of the present invention are useful for inhibiting the growth of, or eliminating, microorganisms in various environments wherein the presence or unchecked growth of the microorganism is undesirable or harmful. Each of the antimicrobial C-3' spectinomycin analogs of the present invention is microbistatic or microbicidal against at least one microorganism in at least one environment in which the presence of the microorganism is undesirable or harmful. Microorganisms against which at least one of the antimicrobial C-3' spectinomycin analogs of the present invention are active include *E. coli, K. pneumoniae, S. marcescens, S. typhi, S. faecalis, P. vulgaris, P. mirabilis, Ps. aeruginosa*, as well as others, including both gram-negative and gram-positive bacteria. Some of the novel, antimicrobial C-3' spectinomycin analogs of the present invention are also useful for treating or preventing microbial infections in mammals, including humans.

Other than well known deprotection reactions required to replace blocking groups with hydrogen atoms on blocked nitrogen atoms, the chemical transformations disclosed in the present specification occur at C-3'. None of the chemical transformations disclosed in the present specification alter the configuration at any chiral center, other than C-3', from the configuration exhibited by spectinomycin, its actinamine-ring-nitrogen-blocked analogs, or any of the C-6' analogs of spectinomycin (including actinamine-ring-nitrogen-blocked) of concern in the present specification as starting materials in the synthesis of the novel C-3' analogs. Consequently, in many of the structural formulas used in the present specification, only the region of the structure near the C-3' position will be depicted. In such formulas, the portion of the structure not shown, including configurations at chiral centers not shown, is as in spectinomycin (formula XX) or the relevant C-6' analog thereof. The configuration about any chiral center that may be present in a blocking group or a substituent at C-6' is not changed by any of the chemical transformations disclosed in the present specification.

Configurations at C-3' of the novel compounds disclosed herein are specified as either "R" or "S" in accordance with sequence rules well known to the art. Configurations about olefinic double bonds are specified using "E" to designate the trans-configuration and "Z" to designate the cis-configuration utilizing similarly art-recognized procedures for identifying geometric isomers.

2. Prior Art

Several C-3' analogs of spectinomycin, with and without blocking groups on the actinamine-ring nitrogens (i.e., the nitrogens bonded to C-1 and C-3) are known. In aqueous solution, spectinomycin exists as the C-3' ketone hydrate (formula XXII). Wiley, et al., J. Am. Chem. Soc. 85, 2652 (1963).

Wiley, et al., J. Am. Chem. Soc. 85, 2652 (1963) also report the preparation of both C-3' epimers of 3'-dihydro-spectinomycin (formula XXIII).

Knight and Hoeksema, J. Antibiotics 28, 136 (1975), disclose the N,N'-di(carbobenzyloxy) derivative of spectinomycin itself and both epimers of the 3'-dihydro analog. (The nitrogen atoms bonded to C-1 and C-3 are designated herein as N and N', respectively.)

Maier, et al., U.S. Pat. No. 4,173,647, disclose both epimers of 3'-deoxo-3'-amino-3'-dihydrospectinomycin (formula XXIV) and a large number of actinamine-ring-nitrogen-blocked analogs of both including specifically the N,N'-di(carbobenzyloxy), N,N'-di(p-methoxybenzyloxycarbonyl), N,N'-di[(2,2,2-trichloroethoxy)carbonyl], and N,N'-di(isobornyloxycarbonyl) analogs. The Maier, et al. U.S. patent also discloses a large number of actinamine-ring-nitrogen-blocked analogs of spectinomycin itself, including specifically the same five named above for the 3'-deoxo-3'-amino-3'-dihydro-epimers. The Maier, et al. U.S. patent also discloses numerous oximes and hydrazones of spectinomycin and numerous actinamine-ring-nitrogen-blocked analogs of spectinomycin. The patent discloses specifically spectinomycin benzyloxime and the N,N'-di(carbobenzyloxy) analog thereof, the N,N'-di(carbobenzyloxy) analog of spectinomycin methyloxime, spectinomycin benzylhydrazone and spectinomycin acethydrazone.

Numerous oximes and hydrazones of spectinomycin, and actinamine-ring-nitrogen-blocked analogs thereof, are also disclosed in Federal Republic of Germany Offenlegungschrift No. 2,756,912, published July 5, 1979 and abstracted at Derwent Farmdoc Accession No. 50959B. Methylsulfonylhydrazone and (p-toly)sulfonylhydrazone (i.e., tosylhydrazone) of spectinomycin and many of its N,N'-diblocked analogs are described in German Offenlegungschrift No. 2,756,912.

Formula XXV shows the C-3'-region of spectinomycin hydrazone, a compound generically disclosed in U.S. Pat. No. 4,173,647. Formula XXVI shows the C-3' region of spectinomycin tosylhydrazone.

Maier, et al., in J. Antibiotics 34, 16 (1981), report information on the synthesis and biological activity of both C-3'-epimers of 3'-deoxo-3'-amino-3'-dihydrospectinomycin, which is closely related to the disclosure of U.S. Pat. No. 4,173,647.

Woitun, et al., in J. Antibiotics 34, 22 (1981), a reference not necessarily subsequent to any invention disclosed herein, disclose numerous 3'-substituted amino analogs of 3'-deoxo-3'-(R)-3'-amino-3'-dihydrospectinomycin and its N,N'-di(carbobenzyloxy) analog. The compounds disclosed in the Woitun, et al. reference which are closest to the subject matter of the present invention are illustrated by formula XXVII, wherein $R_{27}$ is methyl, ethyl, isopropyl, n-pentyl, n-nonyl, n-dodecyl or n-octadecyl, and formula XXVIII, wherein $R_{28}$ is methyl or ethyl. Both compounds represented by formula XXVIII are reported in the Woitun, et al. reference to be inactive as antimicrobial agents.

Hanessian, et al., in J. Antibiotics 34, 350 (1981), another reference not necessarily subsequent to any invention disclosed herein, disclose 3'-deoxo-3'-(S)-methylsulfonyloxy-N,N'-di(carbobenzyloxy)-3'-dihydrospectinomycin and 3'-deoxo-3'-(S)-3'azido-N,N'-di(-carbobenzyloxy)-3'-dihydrospectinomycin (formula XXIX).

Numerous analogs of both 3'-epimers of 3'-dihydrospectinomycin are reported in U.S. patent application Ser. No. 020,073, filed Mar. 13, 1979. The analogs include actinamine-ring-nitrogen unblocked and blocked with a wide variety of blocking groups, 5'-desmethyl compounds and compounds substituted at C-6' with a variety of substituents, including all the C-6' substituents within the scope of the present invention except the nitrogen-containing 6'-substituents in which the nitrogen atom is bonded to a blocking group. The C-3' region of compounds disclosed in U.S. patent application Ser. No. 020,073, filed Mar. 13, 1979, is displayed in formula XXX, wherein $R_{30}$ includes hydrogen and alkyl of 1 to 8 carbon atoms, inclusive. Formula XXX is intended to indicate both the 3'-(R) and 3'-(S) stereoisomer of each analog.

No analogs of spectinomycin appear known to the art wherein a halogen or carbon atom is bonded directly to C-3' or wherein a nitrogen atom, where present in a C-6' substituent, is bonded to a blocking group.

Maier, et al., U.S. Pat. No. 4,173,647; Federal Republic of Germany Offenlegungschriften Nos. 2,756,913 (Derwent Farmdoc Accession No. 50960B) and 2,756,914 (Derwent Farmdoc Accession No. 50961B); and Maier, et al., J. Antibiotics 34, 16 (1981) teach the reduction of spectinomycin hydrazones (formulas XXV and XXVI) and oximes to both epimers of 3'-deoxo-3'-amino-3'-dihydrospectinomycins. The references teach the presence of acid is advantageous in the reductions.

Hanessian, et al., J. Antibiotics 34, 350 (1981), discloses reduction by precious metal-catalyzed hydrogenolysis of 3'-deoxo-N,N'-di(carbobenzyloxy)-3'-(S)-3'-azido-3'-dihydrospectinomycin to 3'-deoxo-3'-(S)-3'-amino-3'-dihydrospectinomycin.

House, et al., J. Org. Chem. 33, 53 (1968), teach the formation of diazoacetic acid esters of unsaturated alcohols by the reaction of acetic acid tosylhydrazone esters of unsaturated alcohols with triethylamine in methylene chloride. In view of the known base-sensitivity of spectinomycin and its analogs, as well as the significant structural and chemical differences between the C-3' region of 3'-arylsulfonylhydrazones of spectinomycin and its analogs and the carboxylate-carbon region of acetic acid arylsulfonylhydrazone esters, provide no basis to predicting whether the reaction conditions employed by House, et al., could be used to successfully form 3'-deoxo-3'-diazo-spectinomycin.

There appear to be no examples of reactions between diazo ketones (e.g., in formula XXXI, the C-2'-C-3' region of 3'-deoxo-3'-diazo-spectinomycin), and (N,N-dialkyl)methyleneammonium halides prior to the disclosure herein of such a reaction used to link a carbon atom to the C-3' of spectinomycins by formation of 3'-deoxo-3'-(N,N-dialkyl)-enamino-spectinomycins, which, as shown in the present specification, are valuable as intermediates in synthesis of antimicrobial 3'-analogs of spectinomycin.

A review of hydrocyanation reactions of aldehydes and ketones, and the stereoselectivity thereof, is provided by Mathieu, et al., *Formation of C—C Bonds*, G. Thieme Publ. Stuttgart, W. Germany, Vol. I, pp. 429-440 (1973). See also Grewe, et al., Chem. Ber. 98, 104 (1965). In accordance with the disclosure herein hydrocyanation occurs at the C-3' ketone in spectinomycins under reaction conditions of novel processes (iii) described briefly above and in greater detail below. The prior art teaches that the 3'-(R)-spectinomycin cyanohydrins would be expected as the predominant products under such reaction conditions. Surprisingly and unexpectedly this kinetically favored product of the hydrocyanation, the 3'-(R)-spectinomycin cyanohydrin, is thermodynamically less stable than the 3'-(S)-epimer.

The known spectinomycin analogs described herein, with the exception of the two compounds of formula XXVIII disclosed by Woitun, et al., J. Antibiotics 34, 22 (1981), for which no utility is described, are asserted in the various references cited to be useful as either antimicrobial agents or intermediates in processes for synthesizing analogs which are antimicrobials. All analogs which have blocking groups on the nitrogens bonded to C-1 and C-3 in the actinamine ring, and all 3'-hydrazone and 3'-oxime analogs, are described to be useful as such intermediates. The other analogs, other than the two of formula XXVIII disclosed in the Woitun, et al. reference, are disclosed to be useful as antimicrobials.

THE INVENTION

SUMMARY OF THE INVENTION

The present invention comprises:
(A) A compound of formula I, wherein $R_1$ is
  (a) hydrogen or
  (b) a blocking group;
  wherein $R_3$ is
  (a) hydrogen
  (b) alkyl of 1 to 8 carbon atoms, inclusive,
  (c) $-R_{31}-O-R_{32}$, wherein $R_{31}$ is alkylene of 1 to 4 carbon atoms, inclusive, and $R_{32}$ is hydrogen or alkyl of 1 to 6 carbon atoms, inclusive, with the proviso that the sum of the number of carbon atoms in $R_{31}$ and the number of carbon atoms in $R_{32}$ is less than or equal to 7,
  (d) $-R_{31}-NR_{33}R_{34}$, wherein $R_{31}$ is as defined above, wherein $R_{33}$ is hydrogen or alkyl of 1 to 6 carbon atoms, inclusive, and $R_{34}$ is hydrogen, alkyl of 1 to 6 carbon atoms, inclusive, or a blocking group, with the proviso that if $R_{34}$ is not a blocking group, the sum of the number of carbon atoms in $R_{31}$ and the number of carbon atoms in whichever of $R_{33}$ or $R_{34}$ has the larger number of carbon atoms is less than or equal to 7, or
  (e) alkyl of 1 to 4 carbon atoms, inclusive, substituted with 1, 2, or 3 halogen atoms;
  wherein A is
  (a) $=N_2$,
  (b) $\alpha-H:\beta-H$,
  (c) $\alpha-H:\beta-X$, wherein X is chlorine or bromine, i.e., the configuration at C-3' is (R),
  (d) $\alpha-Cl:\beta-Cl$,
  (e) $=CH(NR_5R_6)$, with the proviso that
    (i) $R_1$ is a blocking group and
    (ii) $R_{34}$ is not hydrogen and, if $R_{33}$ is hydrogen, $R_{34}$ is a blocking group, and wherein $R_5$ and $R_6$, being the same or different, are alkyl of 1 to 6 carbon atoms, inclusive, and wherein the configuration at the vinylogous carbon bonded to C-3' is, with respect to C-2', E or Z, but not both,
  (f) $\alpha-CHO:\beta-H$, i.e., the configuration at C-3' is (R), with the proviso that
    (i) $R_1$ is a blocking group and
    (ii) $R_{34}$ is not hydrogen and, if $R_{33}$ is hydrogen, $R_{34}$ is a blocking group,
  (g) methylene ($=CH_2$), with the proviso that
    (i) $R_1$ is a blocking group and
    (ii) $R_{34}$ is not hydrogen and, if $R_{33}$ is hydrogen, $R_{34}$ is a blocking group,
  (h) $\alpha-CH_2OH:\beta-H$, i.e., the configuration at C-3' is (R),
  (i) $\alpha-H:\beta-CH_2NR_5R_6$ or $\alpha-CH_2NR_5R_6:\beta-H$, i.e., the configuration at C-3' is (R) or (S) but not both,
  (j) $\alpha-CH_2OH:\beta-OH$, i.e., the configuration at C-3' is (S),
  (k) epoxymethano ($-O-CH_2-$ or $-CH_2-O-$), with the proviso that
    (i) $R_1$ is a blocking group and
    (ii) $R_{34}$ is not hydrogen and, if $R_{33}$ is hydrogen, $R_{34}$ is a blocking group,
  (l) $\alpha-OH:\beta-CH_2N_3$ or $\alpha-CH_2N_3:\beta-OH$, i.e., the configuration at C-3' is (R) or (S), with the proviso that
    (i) $R_1$ is a blocking group and (ii) $R_{34}$ is not hydrogen and, if $R_{33}$ is hydrogen, $R_{34}$ is a blocking group, (m) $\alpha$—OH:$\beta$—(CH$_2$)$_m$—CN or $\alpha$—(CH$_2$)$_m$—CN:$\beta$—OH, wherein m is 0 or 1, i.e., the configuration at C-3' is (R) or (S), (n) $\alpha$—OH:$\beta$—(CH$_2$)$_p$—NR$_{41}$R$_{42}$ or $\alpha$—(CH$_2$)$_p$—NR$_{41}$R$_{42}$:$\beta$—OH, wherein p is 1 or 2, and $R_{41}$ and $R_{42}$, being the same or different, are
  (i) hydrogen
  (ii) alkyl of 1 to 12 carbon atoms, inclusive,
  (iii) aryl of 6 to 12 carbon atoms, or
  (iv) aralkyl of 7 to 12 carbon atoms, inclusive, optionally substituted by one or two
    (1) fluoro, chloro or iodo,
    (2) —NR$_{46}$R$_{47}$, wherein R$_{46}$ and R$_{47}$ are hydrogen or alkyl of one to 6 carbon atoms, inclusive, being the same or different,
    (3) cyano,
    (4) hydroxy,
    (5) carboxy,
    (6) alkoxycarbonyl of 2 to 5 carbon atoms, inclusive, or
    (7) alkoxy of one to 4 carbon atoms, inclusive,
  (v) —R$_{43}$—R$_{44}$, wherein —R$_{43}$— is a single bond or R$_{43}$ is alkylene of 1 to 4 carbon atoms, inclusive, and R$_{44}$ is cycloalkyl of 3 to 10 carbon atoms, inclusive, or R$_{41}$ and R$_{42}$ taken together with N form a heterocyclic amine ring with 3 to 10 carbon atoms, inclusive, in the ring, or
  (vi) —CO—R$_{45}$, wherein R$_{45}$ is
(a) alkyl of one to 12 carbon atoms, inclusive, or aryl or aralkyl of 7 to 12 carbon atoms optionally substituted by one or two
    (1) fluoro, chloro or iodo,
    (2) —NR$_{46}$R$_{47}$, wherein R$_{46}$ and R$_{47}$ are hydrogen or alkyl of one to 6 carbon atoms, inclusive, being the same or different,
    (3) cyano,
    (4) hydroxy,
    (5) carboxy,
    (6) alkoxycarbonyl of 2 to 5 carbon atoms, inclusive, or
    (7) alkoxy of one to 4 carbon atoms, inclusive,
(b) —R$_{43}$—R$_{44}$ wherein R$_{43}$ and R$_{44}$ are as defined above, or
(c) pyridyl, piperazyl, pyrollyl or morpholinyl optionally substituted by
    (1) fluoro, chloro or iodo,
    (2) —NR$_{46}$R$_{47}$, wherein R$_{46}$ and R$_{47}$ are hydrogen or alkyl of one to 6 carbon atoms, inclusive, being the same or different,
    (3) cyano,
    (4) hydroxy,
    (5) carboxy,
    (6) alkoxycarbonyl of 2 to 5 carbon atoms, inclusive, or
    (7) alkoxy of one to 4 carbon atoms, inclusive;
and wherein B$_1$ is $\alpha$—OH:$\beta$—H and B$_2$ is oxo, when A is =N$_2$ or =CH(NR$_5$R$_6$), or B$_1$ is $\alpha$—B$_3$:$\beta$—H and B$_2$ is $\alpha$—B$_4$:$\beta$—OH wherein B$_3$ and B$_4$ are taken together to form oxa (—O—), when A is not =N$_2$ or =CH(NR$_5$R$_6$); or the pharmacologically acceptable acid addition salts thereof when R$_1$ and R$_{34}$ are not blocking groups and A is not =N$_2$.

(B) A process for preparing a compound of formula II wherein R$_1$ and R$_3$ are as defined above, which comprises:
reacting in an inert organic solvent a compound of formula III wherein R$_4$ is an aryl group, with an organic amine base.

(C) A process for preparing a compound of formula IV,
wherein R$_7$ is a blocking group;
wherein R$_3$ is as defined above;
wherein R$_5$ and R$_6$, being the same or different, are alkyl of 1 to 6 carbon atoms, inclusive; and
wherein the configuration at the carbon atom to which —NR$_5$R$_6$ is bonded is, with respect to C-2', E or Z but not both, which comprises:
reacting a compound of formula V, wherein R$_7$ is as defined above, with a compound of formula VI, wherein X$_6$ is chlorine or bromine, in the presence of a tertiary amine base in a solvent R$_8$CN, wherein R$_8$ is alkyl of 1 to 3 carbon atoms, inclusive.

(D) A process for C-3' stereoselectively preparing a compound of formula VII, wherein R$_1$ and R$_3$ are as defined above, such that said compound is present in an amount greater than the amount of the co-produced C-3' epimer thereof, which comprises:
  (a) combining a compound of formula VIII with a compound which is a source of cyano groups, in an unreactive organic solvent in the presence of base or basic ion exchange resin, and
  (b) isomerizing at the C-3' position of the compound of the reaction product of step (a) by allowing the reaction product to remain in the solution for a length of time sufficient to result in the formation of a mixture of the compound of formula VII with its C-3' epimer, characterized by an amount of the compound of formula VII which is greater than the amount of its C-3' epimer.

(E) A process for C-3' stereoselectively preparing a compound of formula X, wherein R$_1$ and R$_3$ are as defined above, such that said formula X compound is present in an amount greater than the amount of the C-3' epimer thereof, which comprises:
  (a) combining a compound of formula VIII with a compound which is a source of cyano groups, in an unreactive organic solvent in the presence of base or basic ion exchange resin, and
  (b) permitting reaction of step (a) to proceed in the solution for a length of time sufficient to result in the formation of compound of formula X, and
  (c) terminating the reaction of step (b) prior to the formation of an amount of said C-3' epimer which is larger than the amount of said formula X compound by (i) quenching said reaction by the addition of acid to neutralize said base of said basic ion-exchange resin or (ii) removing said ion-exchange resin if no other base is present.

(F) A process for preparing a compound of formula VII wherein R$_1$ and R$_3$ are as defined above, from a compound of formula X which comprises:
combining a compound of formula X with a base or a basic ion-exchange resin in an unreactive organic solvent.

Bivalent substituents herein, e.g., A, B$_1$ and B$_2$ are defined, at least in part in the form $\alpha$—R$_i$:$\beta$—R$_j$, wherein R$_i$ represents the substituent in the alpha configuration and R$_j$ represents the substituent in the beta configuration with respect to the plane of the ring to which said substituent is attached.

The term "aryl group" and "aralkyl group" in the definitions above are defined as is conventional in the art. See the discussion pertaining to the Charts. For convenience in assigning trivial names to compounds herein when $B_1$ is $\alpha$—$B_3$:$\beta$—H and $B_2$ is $\alpha$—$B_4$:$\beta$—OH, the chemical skeleton described when $R_1$ is hydrogen and $R_3$ is methyl in formula I shall be referred to as "secospectinomycin".

The compounds within the scope of the invention are useful as either antimicrobial agents or intermediates and processes for synthesizing antimicrobial agents. The compounds within the scope of the present invention which are antimicrobial agents are the compounds of formula I wherein $R_1$ and $R_{34}$ are no blocking groups and A is not $=N_2$, and pharmacologically acceptable acid addition salts thereof. The compounds within the scope of the present invention which are useful as intermediates in synthetic processes to make the antimicrobial compounds of the invention are those of formula I wherein $R_1$ or $R_{34}$ or both $R_1$ and $R_{34}$, are blocking groups or A is $=N_2$.

The compounds within the scope of the invention which are useful as antimicrobial agents are microbistatic or microbicidal. They can be used to inhibit the growth of, or eliminate, microorganisms, including gram-negative and gram-positive bacteria, from environments in which the presence of microorganisms is undesirable or harmful. While the microbistatic or microbicidal potency of the antimicrobial agents within the scope of the invention will vary against any undesirable or harmful species of microorganisms in a particular environment, each antimicrobial agent within the scope of the invention will be useful against at least one species of microorganism in at least one environment in which the presence of members of the species is harmful or undesirable.

Some of the antimicrobial agents within the scope of the invention are useful for treating or preventing microbial, especially bacterial, infections in mammals, including humans. It is contemplated that the antimicrobial agents within the scope of the invention wherein A is $\alpha$—Cl:$\beta$—Cl, $\alpha$—H:$\beta$—Cl and $\alpha$—H:$\beta$—Br will not be useful for treating or preventing microbial infections in mammals. It is contemplated that most, if not all, of the other antimicrobial agents within the scope of the invention will be useful for treating or preventing microbial infections in mammals, including possibly humans. Whether an antimicrobial agent within the scope of the present invention is useful for treating or preventing microbial infections in mammals or not, it will nonetheless be useful for inhibiting the growth of, or eliminating, microorganisms from environments, other than mammalian systems, in which the presence of the microorganisms is undesirable or harmful.

To be effective as microbistatic or microbicidal agents in an environment, the antimicrobial compounds within the scope of this invention must be introduced into the environment, by one of several means which are well known in the art and which are described in more detail below, in a quantity sufficient to inhibit the growth of, or eliminate, the target microorganisms.

DETAILED DESCRIPTION OF THE INVENTION

The illustrative examples below and Charts A to F describe the preparation and use of the novel compounds and processes herein. Variations from the details given herein, e.g., solvent or temperature or other reaction conditions, provided in the Examples and Charts, are also contemplated as part of the invention. The Examples and Charts are intended therefore to be illustrative, not comprehensive. Except as otherwise noted, however, the Examples do set forth preferred conditions for the reactions exemplified.

Compounds of formula VIII in Charts A and F are the starting materials for synthesizing all compounds within the scope of this invention. All compounds of formula VIII, except those in which $R_{34}$ within $R_3$ is a blocking group, are known. For such starting materials see U.S. patent application Ser. No. 150,530, filed May 16, 1980, the relevant disclosure of which is incorporated here by reference. A blocking group can be incorporated into $R_3$ (as $R_{34}$) by employing the procedures exemplified in examples below for blocking the actinamine-ring nitrogens of spectinomycin with an unblocked or actinamine-ring nitrogen-blocked spectinomycin-analog starting material wherein $R_3$ is an aminoalkyl or substituted aminoalkyl group. After this blocking reaction, wherein the starting material is unblocked, $R_{34}$ will be the same as the blocking groups on the actinamine-ring nitrogens. If the starting-material spectinomycin analog is blocked before use in the reaction to block a nitrogen optionally present in $R_3$, $R_{34}$ can be optionally different from the blocking groups on the actinamine-ring nitrogens.

As disclosed by Maier et al., U.S. Pat. No. 4,173,647, and Federal Republic of Germany Offenlegungsschrift No. 2,756,912, the hydrazone or arylsulfonylhydrazone of formula XLII can be formed by well known methods for synthesis of hydrazones from ketones and hydrazine or arylsulfonylhydrazides, respectively.

In Chart A, $R_{60}$ is hydrogen or arylsulfonyl. The preferred route of synthesis of the formula XLIII diazo ketone is through an arylsulfonylhydrazone intermediate.

Chemical transformations of the formula XLII to formula XLIII compounds described in Chart A are undertaken in any organic solvent which is inert with the reactants and in which the reactants are soluble. For the formation of the formula XLIII diazo ketone from the formula XLII arylsulfonylhydrazone, such solvents include, for example, benzene, hexane, dimethyl ether, diethyl ether, tetrahydrofuran, unreactive chlorinated hydrocarbons such as methylene chloride and ethylene chloride, and the like. The preferred solvent is methylene chloride.

The transformation of the formula VIII compound to the formula XLIII compound can be carried out at any temperature at which it proceeds at a rate acceptable to the person conducting it, at which reactants remain in solution in the solvent being employed, and at which reactants or products do not thermally decompose. Generally temperatures between 0° C. and 60° C. are acceptable. Preferred temperatures are 20°–30° C. Any organic amine base which is soluble in the solvent employed can be used in the reaction. The preferred base is triethylamine. Preferably the amount of base employed in the reaction is two times the amount of arylsulfonylhydrazone employed. $R_4$, the aryl moiety on the arylsulfonyl groups, can be phenyl optionally substituted with one or two alkyl of 1 to 6 carbon atoms, inclusive, cycloalkyl of 3 to 8 carbon atoms, inclusive, or phenyl likewise optionally substituted by one or two alkyl of 1 to 6 carbon atoms, inclusive. Preferred are p-tolyl, m-tolyl and phenyl. Especially preferred is p-tolyl. The reaction is carried out with nitrogen atoms in the spectinomycin moiety (other than at C-3') blocked or unblocked. Preferably the nitrogens are blocked, most preferably with carbobenzyloxy or t-butoxycarbonyl.

In Chart B, $X_{70}$ is chloro or bromo and Y is hydrogen or chlorine, provided that Y is chloro only when $X_{70}$ is chloro. In Chart B, the diazo ketone of formula XLIII is blocked or unblocked at nitrogens other than those in the diazo group, except that, in the process leading to compound of formula LXXVII, the formula XLIII diazo ketone must be blocked. The preferred route to the compound of formula LXXVIII is to start with a diazo ketone of formula XLIII blocked with carbobenzyloxy. The preferred route to compounds LXXV or LXXIX is to start with a diazo ketone of formula XLIII blocked with t-butoxycarbonyl and proceed through the compound LXXVI intermediate.

The starting materials, compounds V, XLV, LIII and LIV, in the processes illustrated in Charts C, D, and E are necessarily blocked with a blocking group on the actinamine-ring nitrogen atoms.

"Blocking groups", including those optionally present on the nitrogen atom, if any, in the substituent on C-6', are selected from a large number of such groups well known from peptide chemistry. The list of such groups in columns 2 and 3 of U.S. Pat. No. 4,173,647 includes all that can be used in the present invention as well as several (4-acetoxy- or 4-ethoxycarbonyloxybenzyloxycarbonyl, alkoxycarbonyl groups substituted with a furyl-(2)- or p-tolylsulfonyl group, a phenoxycarbonyl group substituted by a nitro group, and any dialkylaminooxycarbonyl group) that are not utilizable for the present invention. Those skilled in the art will readily recognize how to modify reaction conditions from those provided in the examples to add and remove blocking groups other than those for which conditions are specifically exemplified. In this specification, "blocking group" and "protecting group" are synonymous, as are "block" and "protect", and "deblock" and "deprotect". Preferred blocking group in all reactions within the scope of the present invention, except the sequences XLIII→LXXVI→LXXV and XLIII→LXXVI→LXXIX illustrated in Chart B, is carbobenzyloxy. In these two excepted reaction sequences, the preferred group is t-butoxycarbonyl.

Except as otherwise noted herein, the deblocking steps indicated in the various Charts are required to obtain antimicrobially active compounds from blocked intermediates. In the Charts, compounds are not redrawn after the arrows indicating deblocking because deblocking simply replaces blocking groups on the nitrogen atoms to which they are bonded with hydrogen atoms and does not affect the molecules in any other way. Because deblocking does not affect substituents or configurations at C-3', redrawing structures after arrows indicating deblocking is superfluous.

When deblocking leads directly to an acid addition salt, the free base can be generated from such salt by methods well known in the art, e.g., passing a solution of the salt in a solvent such as water, methanol, ethanol, tetrahydrofuran, 1,2-dimethoxyethane or the like through a basic ion exchange resin and collecting fractions of eluate which contain the free base.

Pharmacologically acceptable acid addition salts can be produced from the free bases by methods well known in the art, e.g., neutralizing the free base in solution in a solvent such as water, methanol, ethanol, isopropanol, ether, 1,2-dimethoxyethane, p-dioxane or the like with any acid which has a pharmacologically acceptable conjugate base and then isolating the salt by filtration and direct crystallization or by evaporation of solvent followed by subsequent recrystallization from a suitable solvent. Acids which have pharmacologically acceptable conjugate bases include hydrochloric, hydrobromic, hydroiodic, sulfuric, phosphoric, maleic, citric, tartaric, fumaric, acetic, and the like. Especially preferred among the pharmacologically acceptable acid addition salts within the scope of the present invention is hydrochloric.

The starting materials in the processes illustrated in Charts A, B, and F (i.e., compound VIII or compound XLIII) are optionally either without any blocking groups, with both actinamine-ring nitrogens blocked and any nitrogen atom optionally present in $R_3$ unblocked, or with both actinamine-ring nitrogens and any nitrogen atom optionally present in $R_3$ blocked. In the process illustrated in Chart F, all steps are preferably carried out with carbobenzyloxy blocking groups on both actinamine ring nitrogens and the nitrogen atom, if any, present in $R_3$. If any of these nitrogen atoms is blocked, the deblocking steps indicated will be necessary to produce an antimicrobial final product. If compound VIII in Chart F contains no blocking groups, all steps through synthesis of 3'-aminomethyl compounds LXIII and LXIV can be carried out. However, to proceed with reductive alkylation of compounds LXIII and LXIV, they must be blocked at both actinamine-ring nitrogens and the nitrogen atom optionally present in $R_3$. The preferred method for synthesizing compounds of formulas LXIII, LXIV, LXV and LXVI is the process illustrated in Chart F.

The sub-processes in Chart D, LV→LXIX→LXXI and LVI→LXX→LXXII can be carried out in the same way as sub-processes LXVIII→LXIV→LXVI and LXVII→LXIII→LXV in Chart F, with possibly minor variations in reaction conditions, because of the additional methylene group in the compounds in Chart D, which would be readily ascertainable by one of ordinary skill.

The formula LXXXVII and LXXXVIII compounds of Chart F are prepared by acylation of N,N'-dibenzyloxycarbonyl-3'-aminomethyldihydrospectinomycins (formulas LXIII and LXIV) by employing methods known in the art such as:

(a) reaction with an acid anhydride,
 (b) reaction with an acid chloride in the presence of base, or
 (c) reaction with an acid and a coupling reagent such as dicyclohexylcarbodiimide or an alkylchloroformate.

Preferred antimicrobial agents within the scope of the present invention are compounds of formula I wherein $R_3$ is alkyl of 1 to 4 carbon atoms, inclusive, and A is $\alpha$—OH:$\beta$—CH$_2$NHR$_{80}$ or $\alpha$—CH$_2$NHR$_{80}$:$\beta$—OH, especially wherein the configuration at C-3' is (R) and wherein $R_{80}$ is n-alkyl of 1 to 8 carbon atoms, inclusive, or (cyclohexyl)methyl. Especially preferred are such compounds wherein $R_3$ is methyl.

In the compounds of formula IV, the configuration at the vinylogous carbon bonded to C-3', with respect to C-2', is not known. However, the process (V+VI)→IV illustrated in Chart C produces a compound stereospecifically at that position. Thus, the configuration is E or Z but not both.

Similarly, in compounds of formula XLVI, the configuration at C-3' is not known, although it is known that the process IV→XLVI illustrated in Chart C is stereospecific at C-3'. Thus, the compound of formula XLVI has configuration 3'—(S) or 3'—(R) but not both.

Compounds of formula VI used in the process illustrated in Chart C are known or are easily synthesized on the basis of the teachings of Schreiber et al., Angew, Chem. (Int'l Ed., English) 10, 330 (1971) and Kinast et al., Angew, Chem. (Int'l Ed., English) 15, 239 (1976). It is important to carrying out the reaction (V+VI) that as little water as possible be present in the reaction medium. Thus, the solvent and amine base should be dry; the salts of formula VI and the compound of formula V should be as dry as possible, the reaction vessel should be dried before the introduction of reactants and the vessel should be flushed with a stream of unreactive, dry gas (e.g., $N_2$) during the reaction. Those of skill in the art will be familiar with methods to minimize the amount of water in a reaction medium. The reaction (V+VI)→IV can be carried out at any temperature at which reactants and products are soluble in the solvent used and stable and at which the reaction proceeds at an acceptable rate. A person skilled in the art will be able to ascertain temperature limits easily. Preferred temperature range is 20°–30° C. Examples of tertiary amine bases that can be used in the process (V+VI)→IV are provided above in the section on Summary of the Invention. Preferred is triethylamine. Preferred solvent is acetonitrile.

The preferred method for making compounds of formula XLV is using the $Na[AlH_2(O(CH_2)_2OCH_3)_2]$ reaction illustrated in Chart C.

$R_{61}$ and $R_{62}$ in Chart D and $R_{63}$ and $R_{64}$ in Charts D, E and F are the same as $R_{41}$ and $R_{42}$ defined above except that not both $R_{63}$ and $R_{64}$ can be hydrogen.

Unless otherwise specified, specific rotations reported in the examples are measure at room temperature, 24±2° C. Gram-molecular weights reported in the examples are determined by high resolution mass spectrometry using, when necessary, trimethylsilated compounds. The extent of silation is indicated for each example. A designation "(M+−Q)", wherein Q is the formula for a functional group or other molecular fragment indicates that the reported mass is determined from the mass of the molecular ion (M+) missing molecular fragment or function group Q.

The compounds of formula I are useful either as intermediates in processes to synthesize antimicrobial agents or as antimicrobial agents.

The compounds of formula I which contain one or more blocking groups or wherein A is $=N_2$ are useful as intermediates in processes to synthesize compounds within the scope of the present invention which are antimicrobial agents.

The compounds of formula I which contain no blocking group and wherein A is not $=N_2$ are antimicrobial agents.

The antimicrobial agents within the scope of the present invention inhibit the growth of, or eliminate, microorganisms in various environments where the presence of microorganisms is undesirable or harmful.

The antimicrobial activity of compounds within the scope of the invention is determined by a serial-dilution technique whereby, for each of several species of microorganisms the minimum concentration of a compound required to prevent an increase in the concentration of cells in an inoculum containing a known initial concentration of cells in a growth phase is determined.

Based on results with the technique applied to the known antibiotic, spectinomycin dihydrochloride, a compound is judged active against species of microorganisms if its "minimum inhibitory concentration" against the microorganisms using the technique is less than 250 mcg/ml. By this criterion, all of the antimicrobial compounds within the scope of the invention were found to be active against at least one of the following species of microorganisms:

S. aureus
S. faecalis
E. coli
K. pneumoniae
Ps. aeruginosa
P. vulgaris
P. mirabilis
S. flexneri
S. marcescens
S. schottmuelleri.

Minimum inhibitory concentrations (in mcg/ml) for several antimicrobial compounds within the scope of the invention are provided in the following Table:

| | Compound | | | | | |
|---|---|---|---|---|---|---|
| | A | B | C | D | E | F |
| S. aureus (UC#76) | 7.8 | 62.5 | 31.2 | 3.9 | 3.9 | <0.25 |
| S. faecalis (UC#694) | 31.2–62.5 | >1000 | 7250 | 125 | 125 | 3.9 |
| E. coli (UC#45) | 3.9–7.8 | 15.6 | 31.2 | 1.0 | 0.5 | 1.0 |
| K. pneumoniae (UC#58) | 2.0 | 7.8 | 3.9 | 1.0 | 1.0 | 3.9 |
| Ps. aeruginosa (UC#95) | 31.2 | 1000 | >250 | 31.2 | 62.5 | 7.8 |
| P. vulgaris (UC#93) | 7.8 | 250 | 62.5 | 3.9 | 15.6 | 31.2 |
| P. mirabilis (UC#667) | 3.9–7.8 | 62.5 | 62.5 | 7.8 | 7.8 | 62.5 |
| S. flexneri (UC#143) | 7.8–15.6 | 31.2 | 15.6 | 3.9 | 3.9 | 3.9 |
| S. marcescens (UC#131) | 3.9 | 62.5 | 15.6 | 1.0 | 1.0 | 7.8 |
| S. schottmuelleri (UC#126) | 15.6–31.2 | >1000 | 250- | — | — | — |
| P. stuartii (UC#6570) | >250–1000 | — | — | 15.6 | 15.6 | 12.5 |

A: Spectinomycin dihydrochloride pentahydrate (control) (Ranges reflect values obtained on different days)
B: 3'-deoxo-3'-(R)-3'-bromo-spectinomycin
C: 3'(S)-3'-hydroxymethyl-dihydrospectinomycin
D: 3'-(R)-3'-aminomethyl-dihydrospectinomycin
E: 3'-(R)-3'-(ethylamino)methyl-dihydrospectinomycin
F: 3'-(R)-3'-[n-octylamino)methyl-dihydrospectinomycin Antimicrobial compounds within the scope of the present invention are active against E. coli and can be used, for example, to reduce, arrest and eradicate slime production in papermill systems caused by this microorganism. The antimicrobial compounds can also be used to prolong the life of cultures of Trichomonas foetus, Trichomonas hominis and Trichomonas vaginalis by freeing them of E. coli contamination. The antimicrobial compounds can be used to swab laboratory benches and equipment in mycological laboratories. The antimicrobial compounds can also be used effectively against K. pneumoniae.

To be used as suggested above, the antimicrobial compounds of the present invention are incorporated into solutions, powders, suspensions, water-in-oil emulsions and like means of delivery which are well known and are described in greater detail below in connection with administration to mammals and humans. The concentration of antimicrobial compound in these means of delivery or application must be at least sufficient to inhibit the growth of target microorganisms at site of application. These minimum effective concentrations will vary, depending on the target microorganism, the environment in which its growth is to be slowed or it is to be eliminated, and the particular means of delivery used. The minimum effective concentration could be determined readily by a person skilled in the art. It is contemplated that the minimum effective concentration will range from about 1 part per million to about 10,000 parts per million, preferably 10 parts per million to 1000 parts per million in the solution, powder, suspension or emulsion. The preferred carrier is water.

The antimicrobial compounds within the scope of the present invention, other than those wherein A is $\alpha$—H:-$\beta$—Br, $\alpha$—H:$\beta$—Cl, $\alpha$—Cl:$\beta$—Cl, or $\alpha$—CH$_2$OH:-$\beta$—H are useful for treating or preventing microbial infections, particularly bacterial infections, in mammals, including humans, suffering from or susceptible to such infections. The antimicrobial activity of a compound in mammals, including humans, is suggested by a minimum inhibitory concentration in the in vitro test described above of less than about 50 $\mu$g/ml against a microorganism. The antimicrobial activity of a compound against a microorganism in mammals, including humans, is ascertained more definitely by testing the ability of the compound to cure mammals, such as mice, rats or rabbits, which have been challenged with an acute dose of the microorganism.

The compounds of formula I are also effective for treating bacterial infections, such as gonorrhea, in mammals, including humans.

The compositions of the present invention are presented for administration to humans and animals in unit dosage forms, such as tablets, capsules, pills, powders, granules, sterile parenteral solutions or suspension, eye drops, oral solutions or suspensions, and water-in-oil emulsions containing suitable quantities of the compound of formula I.

For oral administration, either solid or fluid unit dosage forms can be prepared. For preparing solid compositions such as tablets, the compound of FIG. I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methyl-cellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1–2.5 gm.

The term "unit dosage form" as used in the specification refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampoules, vials, aerosols with metered discharges, segregated multiples of any of the foregoing, and other forms as herein described.

An effective quantity of the compound is employed in treatment. The dosage of the compound for treatment depends on many factors that are well known to those skilled in the art. They include for example, the route of administration and the potency of the particular compound. A dosage schedule for humans of from about 2 to about 4000 mg of compound in a single dose, administered parenterally or in the compositions of this invention, are effective for treating bacterial infections. More specifically, the single dose is from 5 mg to about 5000 mg in a single dose. More specifically, the dose is from about 10 mg to about 2500 mg of compound.

EXAMPLES

The operation of the present invention is further illustrated by the examples below:

EXAMPLE 1

N,N'-dicarbobenzyloxyspectinomycin tosylhydrazone (Formula XLII: $R_{60}$ is tosyl, $R_1$ is carbobenzyloxy and $R_3$ is methyl)

Refer to Chart A.

In 40 ml of absolute ethanol is dissolved 2.5 g (4.2 mmol) of N,N'-dicarbobenzyloxyspectinomycin (formula VIII) and 0.77 g (4.2 mmol) of p-toluenesulfonhydrazide. The reaction is stirred for 2 hr at room temperature under $N_2$. At this time TLC shows no remaining N,N'-dicarbobenzyloxyspectinomycin. Removal of the solvent in vacuo affords 3.13 g (98%) of title product as a white solid foam, which is used without further purification: CMR ($d_6$-Acetone) δ 167.6, 153.4, 144.6, 137.9, 136.4, 130.1, 129.9, 129.0, 128.3, 97.3, 89.9, 74.7, 69.0, 67.2, 66.4, 66.0, 57.70, 57.5, 53.5, 33.2, 31.7, 31.4, 31.2 and 21.3.

EXAMPLE 2

N,N'-dicarbobenzyloxy-3'-deoxo-3'-diazosecospectinomycin (Formula XLIII: $R_1$ and $R_3$ are as in Example 1)

Refer to Chart A.

In a 500 ml round-bottomed flask is dissolved 13.16 g (17.1 mmol) of N,N'-dicarbobenzyloxy-spectinomycin tosylhydrazone (Example 1) in 300 ml of $CH_2Cl_2$. To this solution is then added 2.4 ml (17.1 mmol) of triethylamine. The solution immediately turns yellow and is stirred under $N_2$ for 5 hr. Removal of the solvent in vacuo affords 14.25 g of crude title product as a yellow, brittle foam. The product is chromatographed on 1 kg of silica gel slurry-packed with ethyl acetate. The column is eluted with ethyl acetate. The elution sequence is as follows: 750 ml ethyl acetate, nil; 2450 ml ethyl acetate, 4.75 g of starting tosylhydrazone; 4900 ml ethyl acetate, 6.29 g of diazoketone. The yield of product based on recovered starting material is 94.2%. The product is obtained as a yellow solid: mp 84°–90° (decomp);

IR (KBr), 3450 (a), 2950 (m), 2100 (s), 1675 (s) $cm^{-1}$; PMR ($CDCl_3$) δ 1.38 ($CH_3CH$), 2.7, 3.1 ($CH_2$), 3.1 ($CH_3$—N) 3.2 (CH—N, CH—O), 5.1 (anomeric, $OCH_2Ph$) and 7.3 (aromatic); CMR (Acetone-$d_6$) δ 189.5, 157.5, 138.0, 129.0, 128.2, 102.1, 92.2, 74.5, 73.8, 69.2, 67.9, 67.11, 64.2, 60.1, 59.8, 59.5, 59.3, 31.8, 31.7, 31.46, 31.3, 30.7, 29.8, 29.2, 28.8, and 20.9; $[\alpha]_D = -25°$ (c, 0.7495, $CHCl_3$); UV ($CH_3CN$) λ (max) 297μ (ε=8181); M.S. no M+ observed.

Anal. calc'd for $C_{30}H_{36}O_{10}H_2$: C, 58.82; H, 5.92; N, 9.15; Found: C, 55.84; H, 5.79; N, 7.03.

When this reaction is repeated using 2 equivalents of triethylamine, N,N'-dicarbobenzyloxy-3'-deoxo-3'-diazospectinomycin is isolated in 75% yield.

EXAMPLE 3

N,N'-di-tert-butoxycarbonylspectinomycin (Formula VIII: $R_1$ is tert-butoxycarbonyl and $R_3$ is methyl)

Refer to Chart A.

In 700 ml of $H_2O$ contained in a 3 l Morton flask with overhead stirrer and addition funnel is dissolved 200 g (0.40 mol) of spectinomycin sulfate tetrahydrate. To this solution is carefully added 64 g (0.80 mol) of $NaHCO_3$ in batches. After stirring for 0.5 hr, 700 ml of t-butanol is added, followed by the addition of 176.6 g (0.81 mol) of di-t-butyl-dicarbonate is added over a period of 15 min. The reaction is then stirred for 65 hr at room temperature. The reaction is then transferred to a 4 l separatory funnel and the aqueous phase is separated from the tert-butanol. The tert-butanol is removed in vacuo using a dry ice condenser under high vacuum. The residue consists of a gum which is taken up in 500 ml of ethyl acetate. The aqueous phase is concentrated and extracted with ethyl acetate (2×300 ml). All of the ethyl acetate solutions are combined and washed with water (1×500 ml). An emulsion forms which is broken up with the addition of 500 ml of brine. The aqueous wash is backwashed with 200 ml of ethyl acetate and the combined organics are washed with brine (2×500 ml) and dried over $Na_2SO_4$. The solvent is removed in vacuo and the product is placed under high vacuum overnight to afford 131.38 g (62%) title product of a white solid. No residual tert-butanol is seen by $C^{13}$ NMR. The title product is used without further purification: IR ($CHCl_3$) 3420, 1740 (s), 1675 (s), 1365 (s), 1255 (s), 1160 (s), 1130 (s), 1060 (s), and 885 $cm^{-1}$; NMR ($CDCl_3$) δ 1.4 ($CH_3)_3$ (C—O), 1.4 ($CH_3$—CH), 2.0–3 ($CH_2CO$, CHN's), 2.9, 3.0 ($CH_3N$'s), 3.1–5.0 (CH—O's);

CMR δ 97.3, 91.8, 79.5, 75.1, 68.1, 66.3, 65.6, 60.4, 30.8, 29.8, 28.8, 28.5, 27.9, and 21.5; $[\alpha]_D = -2°$ (C, 0.904, $CHCl_3$).

Anal. calc'd for $C_{24}H_{40}N_2O_{11}$: C, 54.13; H, 7.57; N, 5.26. Found: C, 52.8; H, 7.41; N, 4.76.

Exact mass calc'd for $C_{33}H_{64}N_2O_{11}Si_3$: 748.3818; Found: 748.3772.

EXAMPLE 4

N,N'-di-tert-butoxycarbonylspectinomycin tosylhydrazone (Formula XLII: $R_{60}$ and $R_3$ are as in Example 1 and $R_1$ is as in Example 3)

Refer to Chart A.

A solution containing 100 g (0.19 mol) of N,N'-di-tert-butoxycarbonyl-spectinomycin and 35 g (0.19 mol) of p-toluenesulfonhydrazide in 475 ml of absolute ethanol is stirred for 6.5 hr under $N_2$ at room temperature. The solvent is removed in vacuo and the product is placed under high vacuum overnight. This affords 131 g (100%) of a white solid which is used without further purification. IR (KBr) 3500 (s), 2950 (s), 1650 (s), 1340 (s, broad), 1120 (s, broad), 1090 (s, broad), 925 (s) and 885 (s) $cm^{-1}$; $[\alpha]_D = -2$ (C, 0.982, $CHCl_3$); PMR ($CDCl_3$) δ 1.4 (tButyl), 2.8–3.0 ($CH_3N$'s), 3.4–4.8 (CH—O's), 7.3, 7.8 (aromatic). CMR ($d_6$-Acetone) δ 153.7, 130.2, 129.8, 128.6, 97.4, 90.0, 79.6, 74.9, 69.1, 66.4, 57.7, 30.8, 30.7, 29.8, 28.9, 28.5, 27.9, 21.3 and 18.6.

Anal. calc'd for $C_{31}H_{48}N_4O_{12}S$: C, 53.13; H, 6.90; N, 7.99; S, 4.58. Found: C, 51.85; H, 6.90; N, 7.67.

EXAMPLE 5

N,N'-di-tert-butoxycarbonyl-3'-deoxo-3'-diazo-secospectinomycin (Formula XLIII: $R_1$, $R_3$ and $R_{60}$ are as in Example 4)

Refer to Chart A.

To a solution containing 50 g (71.3 mmol) of N,N'-di-tert-butoxycarbonyl-spectinomycin tosylhydrazone in 500 ml of $CH_2Cl_2$ is added 15 ml (107.6 mmol) of triethylamine. The solution turns yellow/orange and is stirred at room temperature under $N_2$. During the course of the reaction an additional 10 ml (71.3 mmol) of triethylamine is added. After stirring for 8 hr at room temperature, the reaction is stored in the freezer overnight. The next morning the reaction is concentrated to a volume of 100 ml and chromatographed on 1.2 kg of silica gel which has been slurry packed in $CH_2Cl_2$ and then the column was eluted with ethyl acetate. Chromatography affords 33.0 g (85%) of N,N'-di-tert-butoxycarbonyl-3'-deoxo-3'-diazospectinomycin as a yellow solid;

IR (KBr) 3350 (s) 2850 (s), 2050 (s), 1625 (s), 1400 (s), 1325 (s), 1220 (s), 1125 (s), 1030 (s) and 885 (s) cm$^{-1}$; CMR (d$_6$-Acetone) δ 189.3, 102.17, 92.7, 79.32, 74.3, 69.1, 68.0, 67.1, 64.0, 59.7, 59.6, 59.2, 30.8, 30.6, 29.9, 29.2, 28.9, 28.6, 27.9 and 21.0; [α]$_D$ = −26° (C, 1.095, CHCl$_3$).

Anal. calc'd for C$_{24}$H$_{40}$N$_4$O$_{10}$: C, 52.93; H, 7.40; N, 10.29. Found: C, 51.96; H, 7.25; N, 7.48%.

EXAMPLE 6

3'-chloro-3'-deoxospectinomycin via non-N-protected diazo spectinomycin intermediates (Formula LXXV: X$_{70}$ is chloro and R$_3$ is methyl)

Refer to Chart B.

A. To a solution of 3.0 g (6.06 mmol) of spectinomycin dihydrochloride pentahydrate in 25 ml of water is added a solution of 1.13 g (6.06 mmol) of p-toluenesulfonylhydrazide in 35 ml of absolute ethanol. The solution is stirred 22 hrs at room temperature and concentrated to dryness. The residue is dissolved in ethanol, concentrated to 20 ml and diluted with ether until cloudy and stored in the refrigerator. The resulting white powder is collected by filtration: yield 1.8 g of formula XLII (R$_7$ is hydrogen) spectinomycin-3'-tosylhydrazone dihydrochloride: $^{13}$C NMR (CD$_3$OD) δ 176.0, 152.8, 145.4, 137.1, 130.6, 128.8, 97.7, 91.1, 71.9, 70.1, 67.6, 67.4, 63.0, 61.8, 59.6, 33.7, 31.9, 21.5, 21.4.

B. A 200 mg (0.35 mmol) sample of the part A tosylhydrazone is suspended in 10 ml of dry CH$_2$Cl$_2$ with rapid stirring for 5 min. Triethylamine (0.19 ml, 1.40 mmol) is added resulting is dissolution of most of the solid and the formation of a bright yellow color. After 10 min, the solution is cooled to 0° and HCl gas is bubbled in, causing the yellow color to dissipate. The excess HCl is purged with an argon stream and the solvent is removed in vacuo to give a white solid. A sample is silyllated with 1:1 dimethylformamide/hexamethyldisilizone at 50° for 30 min and analyzed by GC-MS on an OV-17 column. This analysis shows the product to be a mixture (ca. 1:1) of spectinomycin and the desired 3'-chloro-3'-deoxospectinomycin.

The presence of the diazo ketone in the yellow solution is further demonstrated by infrared spectroscopy. A drop of the solution is concentrated on a salt plate and the infrared spectrum obtained. A strong band at 2101 cm$^{-1}$ is observed, showing the presence of the diazo group. This band is absent in the starting material and is also eliminated by treatment with acid (N$_2$ evolution observed).

EXAMPLE 7

N,N'-dicarbobenzyloxy-3'-diazosecospectinomycin via hydrazone oxidation (Formula XLIII: R$_3$ is methyl)

Refer to Chart A.

In 10 ml of CHCl$_3$ is dissolved 500 mg (0.814 mmol) N,N'-dibenzyloxycarbonylspectinomycin hydrazone. To this solution is added 500 mg (5.75 mmol) of active MnO$_2$. The resulting slurry is stirred for 24 hr at room temperature. The mixture is filtered through a pad of magnesium silicate and the filtrate is concentrated to dryness in vacuo to afford 258 mg of a yellow solid. The product is taken up in ethyl acetate and chromatographed on 20 g of silica, slurry packed in ethyl acetate. The column is eluted with ethyl acetate (2 L). In elution volume 0–200 ml there is obtained 180 mg of a mixture of title product and rearranged product. Elution volume 200–500 ml contains 63 mg of pure title product (12.6% yield) whose $^{13}$C—NMR is identical with that obtained from the treatment of N,N'-dibenzyloxycarbonylspectinomycin tosylhydrazine with triethylamine.

EXAMPLE 8

N,N'-dicarbobenzyloxy-3'-deoxospectinomycin (Formula LXXVII: R$_3$ and R$_1$ are as in Example 1)

Refer to Chart B.

In a 500 ml round-bottomed flask is placed 29 g of zinc dust and 30 ml of 60:40 water/acetic acid. To this stirred zinc suspension is added 7.02 g (11.6 mmol) of Example 7 diazoketone. The solution is decolorized and N$_2$ evolves. The reaction is stirred for 1 hr and is filtered. The filtrate is concentrated in vacuo to a thick liquid which is then partitioned between 100 ml of CHCl$_3$ and 50 ml of water. The CHCl$_3$ phase is separated and combined with two, 50 ml CHCl$_3$ extracts of the aqueous phase. The combined CHCl$_3$ extracts are washed with water (2×50 ml) and saturated aqueous NaHCO$_3$ (1×100 ml). The aqueous washes are backwashed with 50 ml of CHCl$_3$ and the combined organic phases are washed with 100 ml of brine and dried over Na$_2$SO$_4$. Removal of the solvent in vacuo leaves 6.54 g of a white solid. Chromatography on 600 g of silica gel eluting with ethyl acetate affords 2.51 g of N,N'-dicarbobenzyloxy-spectinomycin and 3.03 g of a mixture containing the desired product. The mixture is rechromatographed on 100 g of silica gel and eluted with a methanol/CHCl$_3$ gradient. This affords 1.03 g of pure 3'-deoxo-N,N'-di-carbobenzyloxyspectinomycin (15%): mp 126°–130° (decomp); IR(KBr) 3402 (s), 2950 (s), 1680 (s), 1450 (s), 1350 (s), 1170 (s), 1060 (s), 890 (m), 780 (m), and 710 (m) cm$^{-1}$; CMR (d$_6$-Acetone) δ 157.5, 157.4, 156.8, 138.13, 129.1, 128.3, 97.0, 90.7, 74.5, 72.6, 67.2, 66.4, 65.1, 602, 57.4, 36.2, 31.5, 30.7 and 21.41; NMR (CDCl$_3$) δ 1.2 (CH$_3$CH), 1.4–2.0 (CH$_2$—CH$_2$), δ 3.0 (CH$_3$N), 3.5–4 (CH—O's) 5.1 (anomeric) 7.25 (aromatic); [α]$_D$ = 26° (C 0.44, CHCl$_3$).

Anal. calc'd for C$_{30}$H$_{38}$N$_2$O$_{10}$: C, 61.42, H, 6.53, N, 4.78; Found: C, 59.32; H, 6.32, N, 4.98.

EXAMPLE 9

3'-Deoxospectinomycin dihydrochloride (Formula LXXVIII: R$_3$ is methyl.)

Refer to Chart B.

A 500 mg (0.85 mmol) sample of N,N'-di-CBz-3'-deoxospectinomycin (Example 8) dissolved in 30 ml of isopropyl alcohol is hydrogenated in the presence of 517 mg of a 10% Pd on BaSO$_4$ catalyst for 5 hrs at a pressure of 30 psi. TLC (thin layer chromatography) shows remaining N,N'-dicarbobenzyloxy-3'-deoxospectinomycin. An additional 237 mg 10% Pd/BaSO$_4$ catalyst is added and the hydrogenation continues at 40 psi for 12 hrs. TLC shows only a trace of N,N'-dicarbobenzyloxy-3'-deoxospectinomycin. The reaction is filtered twice through celite and the filtrate acidified with 21 ml of 0.1N HCl/isopropanol solution. Removal of the solvent in vacuo affords 255 mg of a light brown solid. The product is dissolved in water, filtered through a cotton plug and crystallized from aqueous acetone. After cooling for 1 hr at 5° C., 85 mg of a white crystalline solid, pure title product, is collected (25.5%). Mp 195°–198° C. (decom); IR (KBr) 3420 (s), 1450 (m), 1380 (m), 1175

(m), 1100 (m) and 1040 (s) cm$^{-1}$; CMR (d$_6$-Acetone) δ 96.2 (d), 91.4 (s), 74.2 (d), 70.9 (d), 67.1 (d), 66.1 (d), 62.5 (d), 61.0 (d), 59.5 (d), 35.1 (t), 30.9 (q) 30.01 (t) and 21.1 (q).

Exact mass calc. for C$_{29}$H$_{66}$Si$_5$N$_2$O$_6$ (penta—O—TMS): 678.3767; Found: 678.3723.

EXAMPLE 10

3′-chloro-3′-deoxo-N,N′-di-tert-butoxycarbonyl spectinomycin (Formula LXXVI: R$_3$ and R$_7$ are as in Example 3 and X$_{70}$ is as in Example 6)

Refer to Chart B.

In 100 ml of CH$_2$Cl$_2$ is dissolved 10.2 g (18.6 mmol) of N,N′-di-tert-butoxycarbonyl-3′-deoxo-3′-diazo-secospectinomycin, Example 5. The solution is cooled to −70° (Dry Ice/isopropanol) under N$_2$ and is treated with 143 ml of a freshly titrated 0.13M HCl/CH$_2$Cl$_2$ solution. The addition takes 15 min and N$_2$ is evolved. The solution is warmed to room temperature and an additional 20 ml of HCl/CH$_2$Cl$_2$ solution is added. After warming, the solvent is removed in vacuo to afford 9.29 g of an off-white solid. The material is dissolved in ether and chromatographed on 300 g of silica gel packed in ether. The column is eluted with 2 liters of ether followed by 2 liters of ethyl acetate. This affords 2.64 g (25%) of title product, 3′-chloro-3′-deoxo-N,N′-di-tert-butoxycarbonyl spectinomycin as a white solid. A $^{13}$C NMR shows the presence of only one isomer: IR (KBr) 3300 (s), 2900 (s), 1625 (s), 1440 (s), 1410 (s), 1330 (s), 1225 (s), 1125 (s), 1050 (br,s), 870 (s) and 600 (s) cm$^{-1}$; CMR (d$_6$-Acetone) δ 93.8, 90.5, 79.4, 74.9, 74.5, 74.4, 66.6, 66.4, 63.0, 60.6, 60.4, 39.2, 28.61 and 20.8;

[α]$_D$ 18° (C, 1.006, CHCl$_3$); PMR (d$_6$-Acetone) δ 1.3 (CH$_3$), 1.45 (t-Butyl), 1.7 (CH$_2$'s) 3.0 (CH$_3$'s), 3.2–4.7 (CH—O's) and 4.96 (CH—O$_2$).

Exact mass calc'd for tri—O—TMS derivative: C$_{33}$H$_{65}$ClN$_2$O$_{10}$Si$_3$: 768.3635; Found: 768.3679.

EXAMPLE 11

3′-bromo-3′-deoxo-N,N′-di-tert-butoxycarbonyl spectinomycin (Formula LXXVI: X$_{70}$ is bromo and R$_1$ and R$_3$ are as in Example 3)

Refer to Chart B.

In 50 ml of CH$_2$Cl$_2$ is dissolved 10.2 g (18.6 mmol) of N,N′-di-tert-butoxycarbonyl-3′-deoxo-3′-diazo-secospectinomycin, Example 5. The solution is cooled to 0° in an ice bath and treated with 210 ml of a freshly titrated 0.087M HBr/CH$_2$Cl$_2$ solution (18.6 mmol). Nitrogen is evolved during the addition. At the completion of the addition, the reaction is stirred for 2 min, until the evolution of N$_2$ had ceased and the solvent was immediately removed in vacuo to afford 10.1 g of an off-white solid. The product is dissolved in methanol and adsorbed on silica gel. The dry silica gel was then placed on top of a column which had been slurry-packed in ether. The column was then eluted with ether and afforded 4.78 g (43%) of title product, 3′-bromo-3′-deoxo-N,N′-di-tert-butoxycarbonyl spectinomycin as a white solid. A $^{13}$C NMR shows the presence of only 1 isomer. IR (KBr) 3400 (s), 2900 (m), 1640 (s), 1420 (s), 1350 (s), 1230 (s), 1130 (br, s), 1050 (s), 880 (s) and 770 (m) cm$^{-1}$; CMR (d$_6$-Acetone) δ 93.4, 89.4, 79.0, 74.2, 74.0, 73.8, 67.1, 66.1, 65.9, 60.0, 57.1, 57.0, 56.7, 56.6, 56.4, 55.9, 39.1, 28.0 and 27.3; [α]$_D$=+8° (C, 0.984, CHCl$_3$).

Exact mass calc'd for C$_{33}$H$_{65}$N$_2$O$_{10}$Si$_3$Br: 812.3131; Found: 812.3159.

EXAMPLE 12

3′-deoxo-N,N′-di-tert-butoxycarbonyl-3′,3′-dichlorospectinomycin (Formula LXXVI: X$_{70}$ and Y are both chloro, R$_1$ and R$_3$ are as in Example 3)

Refer to Chart B.

In a 1-liter, three-necked round-bottomed flask equipped with addition funnel and thermometer is placed 150 ml of a 0.24M Cl$_2$ solution in CCl$_4$ (36 mmol) and 180 ml of CH$_2$Cl$_2$. The solution is cooled to −70° (Dry Ice/isopropanol) and 10 g (18.4 mmol) of 3′-diazo-N,N′-di-tert-butoxycarbonyl-3′-deoxo-secospectinomycin (Example 5) in 150 ml of CH$_2$Cl$_2$ is added rapidly. N$_2$ evolved during the addition. The reaction is stirred for 5 min after completion of the addition and the solvent is removed in vacuo immediately. This affords 11.16 g of a white solid. The product is dissolved in diethyl ether/CH$_2$Cl$_2$ and chromatographed on 250 g of silica gel slurry packed in diethyl ether. The column is eluted with ether to afford 4.31 g of a white solid which still contains an impurity. Trituration with ether affords 1.77 g of pure material. The mother liquors are concentrated and chromatographed on 100 g of silica eluting with 1% methanol/CHCl$_3$ to afford an additional 2.08 g of pure material. This is combined with the triturated material to give 3.85 g of title product 3′-deoxo-N,N′-di-tert-butoxycarbonyl-3′,3′-dichlorspectinomycin as a white solid; (35%)

IR (KBr) 3350 (s), 2900 (s), 1625 (s) 1450–965 (br, strong), 915 (s), 870 (s), 795 (s) and 760 (s) cm$^{-1}$; CMR (d$_6$-Acetone) δ 94.6, 92.5, 79.5, 74.5, 68.4, 67.0, 66.6, 66.5, 60.8, 50.4, 28.7 and 20.32; [α]$_D$=+10° (C, 1.05, CHCl$_3$).

Exact mass calc'd for C$_{35}$H$_{64}$N$_2$O$_{10}$Cl$_2$Si$_3$: 802.3245; Found: 802.3270.

EXAMPLE 13

3′-chloro-3′-deoxospectinomycin dihydrochloride (Formula LXXV: R$_3$ is methyl and X$_{70}$ is chloro)

Refer to Chart B.

In 1 liter of CH$_2$Cl$_2$ is dissolved 2.0 g (3.6 mmol) of 3′-chloro-3′-deoxo-N,N′-di-tert-butoxycarbonyl-spectinomycin, Example 10. The solution is cooled to 0° in an ice bath and anhydrous HCl is bubbled through the solution for 1 min. The reaction turns cloudy and is stirred for 1 hr at 0°. Removal of the solvent in vacuo affords 1.82 g of a light yellow solid. The product is crystallized from aqueous acetone to afford 586 mg of a white crystalline solid. The mother liquors are lyophilized and the residue crystallized from aqueous acetone to afford an additional 302 mg of product. The total yield of crystallized product is 888 mg (58%); mp 211°–220° (dec); IR (KBr) 3500 (s), 1600 (br, m), 1450 (m), 1380 (m), 1175 (s), 1075 (s) 1040 (s) and 925 (m) cm$^{-1}$; CMR (d$_6$-Acetone) δ 95.9, 93.6, 73.6, 70.9, 69.8, 69.6, 65.2, 64.2, 63.8, 62.0, 41.0, 34.5, and 23.2; [α]$_D$=+11° (C, 0.828, H$_2$O).

Exact mass calc'd for C$_{29}$H$_{65}$ClN$_2$O$_6$Si$_5$: 712.3377; Found: 712.3360.

EXAMPLE 14

3′-bromo-3′-deoxospectinomycin dihydrochloride (Formula LXXV: R$_3$ is methyl, X$_{70}$ is bromo)

Refer to Chart B.

In 1.2 liters of CH$_2$Cl$_2$ is dissolved 3.0 g (5.0 mmol) of 3′-bromo-3′-deoxo-N,N′-di-tert-butoxycarbonyl-spectinomycin, Example 11. The solution is cooled to 0° C. and anhydrous HCl is bubbled through for 1 min. The reaction turns cloudy and is stirred for 1 hr and 10 min at 0°. Removal of the solvent in vacuo left 2.71 g of a white solid. The mother liquors all are lyophilized to afford 1.56 g of a white fluffy solid: CMR ($d_6$-acetone) δ 93.47, 90.6, 71.0, 69.34, 67.5, 67.0, 62.6, 61.2, 59.5, 54.3, 38.9, 31.9, 31.8 and 20.5; $[\alpha]_D$ 7° (C, 0.5900, water).

EXAMPLE 15

3',3'-dichloro-3'-deoxospectinomycin dihydrochloride (Formula LXXIX)

Refer to Chart B.

In 700 ml of $CH_2Cl_2$ is dissolved 3.0 g (5.1 mmol) of dichloride 3'-deoxo-N,N'-di-tert-butoxycarbonyl-3,3'-dichlorospectinomycin, Example 12. The solution is cooled to 0° in an ice bath and anhydrous HCl gas is bubbled through for 1 min. The reaction mixture turns cloudy and is stirred for 1 hr at 0°. Removal of the solvent in vacuo leaves 2.44 g of a white solid. The product is dissolved in 150 ml of water and is crystallized by the addition of 1400 ml of acetone. The solution is cooled for 1 hr and the product collected by vacuum filtraton. The first crop amounts to 856 mg of a white crystalline solid. The mother liquors are lyophilized and the lyophilized material is recrystallized from acetone/water to afford an additional 430 mg of product. Finally, the mother liquors are lyophilized to afford 625 mg of a white solid. The total yield of crystalline title product is 1.286 g (55): mp 240–250 (dec); IR (KBr), 3500 (s), 3000 (s), 1610 (m) 1450 (m), 1380 (m) 1170 (s), 1120 (s), 1060 (s), 930 (m), 805 (m) and 765 (m) cm$^{-1}$; CMR ($d_6$-Acetone) δ 93.8, 92.7, 91.8, 70.5, 69.7, 68.5, 66.8, 62.4, 59.3, 49.3, 33.3, 31.90 and 20.1; $[\alpha]_D = -10°$ (C, 0.9465, water).

Exact mass calc'd for $C_{29}H_{64}Cl_2N_2O_6Si_5$ (penta—O—TMS): 746.2988;

EXAMPLE 16

3'-(Dimethylamino)methylene-N,N'-dicarbobenzyloxy-secospectinomycin (Formula IV: $R_1$ and $R_3$ are as in Example 1 and $R_5$ and $R_6$ are methyl)

Refer to Chart C.

A 100 ml Morton flask is flame-dried under a stream of nitrogen. After cooling, the flask is charged with 2.0 g (21.4 mmol) of N,N-dimethylmethylene ammonium chloride (formula VI: $R_5$ and $R_6$ are methyl and $X_6$ is chloro) and 50 ml of acetonitrile. To this suspension is added 1.7 ml (23.1 mmol) of dry $Et_3N$ followed by 5.0 g (8.2 mmol) of N,N'-dicarbobenzyloxy-3'-deoxo-3'-diazo-secospectinomycin (Example 2). The solution is stirred for 4.5 hr at room temperature under nitrogen. During this time a slow evolution of nitrogen is observed, the yellow color of the starting material fades and a white precipitate forms. The reaction mixture is filtered and the filtrate concentrated in vacuo to afford 6.73 g of a yellow solid. The product is taken up in $CHCl_3$ and chromatographed on 250 g of silica slurry packed in $CHCl_3$. The column is eluted with an acetone/$CHCl_3$ gradient as follows with 50-ml fractions being collected: 500 ml, 10% acetone/$CHCl_3$; 500 ml 20% acetone/$CHCl_3$; 5 liter 30% acetone/$CHCl_3$ and 1 liter 40% acetone/$CHCl_3$. Fractions 50–133 contain title product. These fractions are pooled and the solvent is removed in vacuo to afford 3.14 g (60%) of product: $^{13}$C—NMR ($d_6$-Acetone) δ 190.0, 154.1, 138.2, 129.1, 128.3, 128.0, 102.6, 99.4, 91.6, 74.5, 69.7, 68.1, 67.9, 67.2, 60.1, 43.6, 33.3, 31.8, and 21.4; $^1$H NMR ($CDCl_3$) δ 1.32 ($CH_3CH$, d, J=6 Hz) 3.11 (N—$CH_3$'s) 3.3–4.4 (OCH, NCH), 5.1 (anomeric, $OCH_2Ph$) 7.25 (aromatic) and 7.7 (=CH—N($CH_3$)$_2$); $[\alpha]_D$ +64(C, 0.998, $CHCl_3$); UV max (EtOH) 204 (ε, 22150) and 338 (ε17,500); IR ($CHCl_3$) 3439 (m), 3009 (m), 2905 (m), 1691 (s), 1652 (m), 1539 (s), 1485 (s), 1453 (s), 1421 (s), 1385 (s), 1343 (s), 1268 (s), 1171 (s) and 1024 cm$^{-1}$.

Exact mass calc'd for $C_{39}H_{57}N_3O_9Si_2$ (tri—O—TMS—TMSOH): 767.3633; Found: 767.3648.

EXAMPLE 17

N,N'-dicarbobenzyloxy-3'-deoxo-3'-formylspectinomycin (Formula XLIV: $R_1$ and $R_3$ are as defined in Example 1)

Refer to Chart C.

To a solution containing 1.0 g (1.6 mol) of Example 16 product in 25 ml of tetrahydrofuran is added 1.6 ml of 1N HCl. The reaction is stirred at room temperature for 2 hr. The tetrahydrofuran is then removed in vacuo and the residue partitioned between $CHCl_3$ and water. The $CHCl_3$ is separated and combined with a 30-ml $CHCl_3$ extract of the aqueous phase. The combined extracts are washed with 25 ml of brine and dried by filtering through a cone of $MgSO_4$. Removal of the solvent in vacuo affords 806 mg of a white solid. The product is dissolved in $CH_2Cl_2$ and chromatographed on 40 g of silica, slurry packed in 1:1 ethyl acetate/hexane. The column is eluted with an ethyl acetate/hexane gradient as follows: 100 ml, 6:4 ethyl acetate/hexane, 100 ml, 7:3 ethyl acetate/hexane, and 1 liter, 8:2 ethyl acetate/hexane. Elution volume 315 ml to 405 ml contains 105 mg of a white solid which is a mixture of isomeric aldehydes by $^{13}$C—NMR. Elution volume 450–630 ml contains 408 mg of pure product, N,N'-dicarbobenzyloxy-3'-deoxo-3'-formylspectinomycin as a white solid: $^{13}$C—NMR ($d_6$-Acetone) δ 138.3, 129.2, 128.5, 96.4, 92.4, 74.5, 73.8, 73.7, 71.1, 67.3, 66.3, 65.4, 61.0, 60.5, 60.4, 57.9, 57.8, 57.4, 56.2, 31.7, 30.8 and 21.4; $^1$H—NMR ($d_6$-Acetone) δ 1.25 (CH—$CH_3$), 1.8–1.9 ($CH_2$, CH) 2.7 (CH—CHO), 3.1 ($CH_3$N), 3.2 ($CH_3$N), 5.1 (anomeric, $OCH_2Ph$), 7.3 (aromatic) and 9.9 (CHO); IR (KBr) 3400 (s), 1650 (s), 1430 (s), 1380 (s), 1330 (s), 1150 (s), 1110 (s) and 1050 (s); $[\alpha]_D = +23°$ (C, 0.969, $CHCl_3$).

Exact mass calc'd for $C_{39}H_{59}N_2O_{11}Si_3$: 815.3426; Found: 815.3444 (M+—$CH_3$).

EXAMPLE 18

N,N'-dicarbobenzyloxy-3'-deoxo-3'-(hydroxymethyl)-spectinomycin (Formula XLVII: $R_1$ and $R_3$ are as in Example 1)

In 10 ml of methanol is dissolved 200 mg (0.325 mmol) of N,N'-dicarbobenzyloxy-3'-deoxo-3'-formylspectinomycin, Example 17. To this solution is added 4 mg (0.105 mmol) of $NaBH_4$. The reaction was stirred for 40 min at room temperature and quenched with 5 ml of 5% aqueous $NaHCO_3$. The methanol is removed in vacuo and the residue partitioned between ethyl acetate (25 ml) and water (25 ml). The ethyl acetate is separated and combined with a 15 ml ethyl acetate extract of the aqueous phase. The combined extracts are washed with 20 ml of brine and dried over $Na_2SO_4$. After filtering, removal of the solvent in vacuo leaves 212 mg of a white solid. This product is dissolved in $CH_2Cl_2$ and chromatographed on 40 g of silica slurry packed in 1:1 ethyl acetate/hexane. The column is eluted with 1 liter of 7:3 ethyl acetate/hexane to afford in elution volume 315–908 ml, 190 mg (95%) of pure N,N'-dicarbobenzyloxy-3'-deoxo-3'-(hydroxy-methyl)spectinomycin as a white solid: $^{13}$C—NMR (d$_6$-Acetone) δ 129.2, 128.4, 96.9, 92.7, 74.9, 74.6, 74.4, 73.8, 71.6, 67.2, 66.6, 64.8, 62.6, 61.2, 61.1, 60.4, 57.9, 57.5, 45.2, 33.0, 31.6 and 21.5; $^1$H—NMR (d$_6$-Acetone) δ 1.1 (CH$_3$CH, d, J=6 Hz), 3.02 (NCH$_3$'s), 3.3–4.2 (N—CH, O—CH), 5.02 (anomeric, OCH$_2$Ph), 7.25 (aromatic); IR (KBr), 3450 (s), 1650 (s), 1425 (s), 1325 (s), 1150 (s), 1125 (s), 1075 (s), 890 (m), 775 (m), 750 (m) and 700 (m) cm$^{-1}$; [α]$_D$=+17° (C, 0.700, CHCl$_3$). Mass spec m/e 817 (tri—O—TMS—CH$_3$), 750, 634, 495, 393, 359, 321, 305, 270, 216, 170, 108, 91 and 73.

EXAMPLE 19

3'-deoxo-3'-(hydroxymethyl)spectinomycin (Formula I: R$_1$ is hydrogen, R$_3$ is methyl, A is α—CH$_2$OH:β—H, B$_1$ is α—B$_3$:β—H and B$_2$ is α—B$_4$:β—OH where B$_3$ and B$_4$ are taken together to form oxa)

Refer to Chart C.

In 2 ml of methanol is dissolved 63 mg (0.102 mmol) of N,N'-dicarbobenzyloxy-3'-deoxo-3'-(hydroxymethyl)spectinomycin. To this solution is added 75 mg of Pd black and 40 μl of formic acid. The mixture is stirred for 7 min, filtered and the solvent removed in vacuo. This affords 50 mg of a material containing some residual solvent. The material is dissolved in water and 2 ml of 0.1N. HCl is added. The sample is immediately frozen and lyophilized overnight. This affords 27 mg of title product as a white solid (62%): $^{13}$C—NMR (D$_2$O) δ 96.3, 93.2, 73.3, 71.3, 67.2, 66.6, 62.5, 61.7, 61.4, 59.5, 45.2, 32.8, 32.6, 31.9 and 21.2.

Exact mass calc'd for C$_{23}$H$_{49}$N$_2$O$_7$Si$_3$ (tri—O—TMS, M+—CH$_3$): 549.2847; Found: 549.2855.

EXAMPLE 20

N,N'-dicarbobenzyloxy-3'-deoxo-3'-methylenespectinomycin by reduction of title product of Example 16 with NaBH$_3$CN (Formula XLV: R$_7$ is as R$_1$ in Example 1 and R$_3$ is methyl)

Refer to Chart C.

In 10 ml of methanol is dissolved 2.0 g (3.1 mmol) of Example 16 product. To this solution is added a trace of bromcresol green indicator in methanol. The solution is adjusted to a pH ≦4 by the addition of 0.1N methanolic HCl and 65 mg (1.03 mmol) of NaCNBH$_3$ in 1 ml of methanol is added. The pH is kept near 4 and the reaction stirred for 2.5 hr. The reaction is then quenched by the addition of 5 ml of saturated NaHCO$_3$ and the methanol is removed in vacuo. The residue is partitioned between 20 ml of water and 20 ml of ethyl acetate. The ethyl acetate is separated and combined with a 10-ml ethyl acetate extract of the aqueous phase. The combined extracts are washed with 20 ml of brine and dried over Na$_2$SO$_4$. Removal of the solvent in vacuo affords 1.73 g of a blue solid. The product is dissolved in CHCl$_3$ and chromatographed on 200 g of silica gel, slurry packed in CHCl$_3$. The column is eluted with an acetone/CHCl$_3$ gradient as follows: 400 ml 10% acetone in CHCl$_3$; 400 ml 20% acetone in CHCl$_3$; 2 liter 30% acetone in CHCl$_3$; 1 liter 1:1 acetone/CHCl$_3$. Elution volume 1400–1650 ml contained 245 mg of overreduced product. Elution volume 1750–2300 ml contains 439 mg of N,N'-dicarbobenzyloxy-3'-deoxo-3'-methylenespectinomycin, title product, as a white solid. Elution volume 3500 ml-finish contains 167 mg of amino compound 3'-deoxo-3'-(N,N-dimethylaminomethyl)-dihydrospectinomycin. The yield of desired methylene compound is 23%: $^{13}$C—NMR (d$_6$-Acetone) δ 146.0, 138.3, 129.1, 128.3, 112.1, 97.5, 92.1, 74.5, 74.0, 72.9, 67.2, 66.4, 65.2, 60.3, 57.8, 57.7, 57.5, 40.8, 31.6 and 21.3; $^1$H—NMR (CDCl$_3$) δ 1.2 (CH$_3$CH, d, J=6 Hz),2.0–2.5 (CH, CH$_2$), 2.9 (NCH$_3$'s), 3.8–4.4 (CH—O, CH—N), 4.5 (CH$_2$=), 5.1 (anomeric, OCH$_2$Ph) and 7.2 (aromatic); IR (CHCl$_3$) 3673 (w), 3587 (m), 3418 (s), 3009 (s), 2952 (s), 1682 (s), 1486 (s), 1454 (s), 1407 (s), 1386 (s), 1346 (s), 1264 (s), 1234 (s), 1167 (s), 1128 (s), 962 (m) and 918 (m) cm$^{-1}$; [α]$_D$=−6° (C, 1,042, CHCl$_3$).

Exact mass calc'd for C$_{30}$H$_{57}$O$_{10}$N$_2$Si$_2$ (M+—CH$_3$ for the bis TMS deriv): 727.3026; Found: 727.3069.

EXAMPLE 21

N,N'-dicarbobenzyloxy-3'-deoxo-3'-methylenespectinomycin and N,N'-dibenzyloxycarbonyl-3'-deoxo-3'-(N,N-dimethylaminomethyl)-dihydrospectinomycin by sodium bis-2-methoxy aluminum hydride reduction of title product of Example 16

Refer to Chart C.

A 300-ml 3-necked Morton flask is flame-dried under a stream of nigrogen. After cooling, the flask is charged with 5.0 g (7.79 mmol) of enaminone and 50 ml of freshly distilled anhydrous tetrahydrofuran. To this solution is then added 2.4 ml of a 3.5M solution of Na[AlH$_2$(OCH$_2$CH$_2$OCH$_3$)$_2$] in toluene, via syringe over a period of 15 min. A vigorous evolution of gas is observed. At completion of the addition, TLC shows a complete loss of starting material. The reaction is then quenched by adding 100 ml of water and 100 ml of ethyl acetate. The entire mixture is then poured into 300 ml of ethyl acetate. The aqueous phase is separated and combined with 2, 100 ml water washes of the ethyl acetate. The combined aqueous washes are re-extracted with ethyl acetate (2×50 ml). The combined ethyl acetate extracts are washed with 200 ml of brine and dried over NaSO$_4$. After filtering, the solvent is removed in vacuo to afford 4.89 g of a white solid. The product is taken up in CHCl$_3$ and chromatographed on 300 g of silica, slurry packed in CHCl$_3$. The column is eluted as follows: 4 L 1% methanol/CHCl$_3$; 4 L 1.5% methanol/CHCl$_3$; 6 L 2% methanol/CHCl$_3$; and 2 L 10% methanol/CHCl$_3$. The first 3 L of eluant are collected and then 50 ml fractions are taken. In elution volume 5.25 l to 9.45 l there appears 1.75 g (36% of theor.) of the title methylene compound. In elution volume 9.5 L to the finish, 1.954 g of mixture of methylene compound and amino compound is obtained.

EXAMPLE 22

N,N'-dicarbobenzyloxy-3'-(hydroxymethyl)dihydrospectinomycin (Formula XLIX: R$_3$ and R$_7$ are as in Example 20)

Refer to Chart D.

In 2 ml of acetone is dissolved 178 mg (0.30 mmol) of N,N'-dicarbobenzyloxy-3'-deoxo-3'-methylenespectinomycin, Example 21, 30 mg (0.114 mmol) of Et$_4$NOAc.4H$_2$O and 66 μl (0.485 mmol) of 70% aqueous tBuOOH. The solution is cooled to 0° and 152 μl of 2.5% OsO$_4$ in tertbutyl alcohol is added. The solution is stirred for an additional 4.5 hr and is quenched with the addition of 2 ml of 10% aqueous NaHSO$_3$ and 2 ml of ethyl acetate. This mixture is stirred for 15 min, poured into 20 ml of brine, and extracted with ethyl acetate (2×20 ml). The combined extracts are washed with 20 ml of brine and dried over $Na_2SO_4$. The solvent is removed in vacuo to afford 171 mg of a brown solid. The product is dissolved in $CHCl_3$ and streaked on two, 2000μ silica gel preparative TLC plates. The plates are eluted with 10% methanol/$CHCl_3$ and visualized under short UV light. The more polar UV active band on each plate is collected and eluted with ethyl acetate. This affords 46 mg (24%) of the title compound as a white solid: $^{13}C$—NMR ($d_6$-Acetone) δ 138.2, 129.2, 128.5, 94.4, 93.9, 74.5, 73.9, 73.6, 67.4, 67.0, 66.6, 65.3, 61.3, 61.2, 61.1, 60.5, 57.9, 57.7, 57.5, 38.6, 31.8, 31.6 and 21.2.

EXAMPLE 23

3'-(hydroxymethyl)dihydrospectinomycin dihydrochloride

Refer to Chart D.

In 6 ml of methanol is dissolved 45 mg (0.071 mmol) of N,N'-dicarbobenzyloxy-3'-(hydroxymethyl)dihydrospectinomycin, Example 22. To this solution is added 57 mg of Pd black and 30 μl (0.75 mmol) of formic acid. The reaction is stirred for 12 min, filtered and the solvent removed in vacuo to afford 32 mg of material. The material is dissolved in water and 1.4 ml of 0.1N HCl is added. The solution is immediately frozen and lyophilized to afford 26 mg (83%) of a white solid: $^{13}C$ NMR ($D_2O$) δ 93.8, 93.7, 74.5, 70.9, 68.4, 67.0, 66.8 59.3, 37.8, 32.5, 31.9 and 20.9; Mass spec. m/e 724 (M+-1) 513, 437, 401, 309, 217, 206, 187, 165, 147, 129, 117, 94, 73, 55 and 43.

EXAMPLE 24

N,N'-dibenzyloxycarbonyl-3'-deoxo-3'-(N,N-dimethylaminomethyl)spectinomycin (Formula XLVI: $R_3$, $R_5$, and $R_6$ are methyl and $R_7$ is as in Example 20)

Refer to Chart C.

A 25 ml two-necked round-bottomed flask is thoroughly dried under nitrogen. After cooling, the flask is charged with 1 g (1.55 mmol) of enaminone and 10 ml of anhydrous methanol, freshly distilled from Mg. To this solution is added 3.1 ml (3.1 mmol) of 1N methanolic HCl followed immediately by 32.6 mg (0.52 mmol) of $NaCNBH_3$. The reaction is stirred for 15 min at room temperature and is quenched by the addition of 5 ml of saturated aqueous $NaHCO_3$. The methanol is removed in vacuo and the residue is partitioned between ethyl acetate and water. The ethyl acetate is separated and combined with one 20-ml ethyl acetate extract of the aqueous phase. The combined extracts are washed with 20 ml of brine and dried over $Na_2SO_4$. The extracts are filtered and the solvent removed in vacuo to afford 972 mg of a white solid. The product is taken up in $CHCl_3$ and chromatographed on 100 g of silica, slurry-packed in $CHCl_3$. The column is eluted as follows: 200 ml 10% acetone in $CHCl_3$; 200 ml 20% acetone in $CHCl_3$; 2 liter, 30% acetone/$CHCl_3$; 1 liter 5% methanol in $CHCl_3$; 10% methanol in $CHCl_3$. Elution volume 1450–3450 contained 329 mg of the title compound as a white solid. In elution volume 3500 ml–4000 ml there is recovered 369 mg of N,N'-dibenzyloxycarbonylactinamine. The yield of desired material is 33%: $^{13}C$—NMR ($d_6$-Acetone) δ 138.0, 129.1, 128.4, 96.8, 93.1, 75.0, 74.7, 71.7, 67.2, 66.4, 64.7, 60.1, 57.3, 45.6, 39.9, 34.1, 31.7, 31.6, and 21.5; $^1H$—NMR ($d_6$-Acetone) δ 1.1 (d, $CHCH_3$, J=6 Hz), 2.2 (N($CH_3$)$_2$; 3.1 ($NCH_3$'s) 3.3–4.7 (OCH, NCH); 5.1 (anomeric, $OCH_2Ph$) and 7.25 (aromatic); IR ($CHCl_3$) 3427 (m), 3363 (m), 3003 (m), 2984 (m), 2955 (m), 2904 (m), 1686 (s), 1454 (s), 1404 (s), 1384 (s), 1343 (s), 1225 (m), 1163 (s), 1125 (s), 1061 (s), 1028 (s), 989 (m), 951 (m), 911 (m) and 694 (m).

Exact mass calc'd for $C_{43}H_{69}N_3O_{10}Si_3$: 859.4290; Found: 859.4316.

EXAMPLE 25

3'-deoxo-3'-(N,N-dimethylaminomethyl)spectinomycin trihydrochloride

Refer to Chart C.

In 5 ml of methanol was dissolved 100 mg (0.155 mmol) of N,N'-dibenzyloxycarbonyl-3'-deoxo-3'-(N,N-dimethylaminomethyl)spectinomycin, Example 24. To this solution was added 100 mg of Pd° and 62 μl (1.55 mmol) of formic acid. The reaction is stirred for 1 hr at room temperature, is filtered and the solvent removed in vacuo to afford 90 mg of a glass. The material is dissolved in water and 4.6 ml (0.46 mmol) of 0.1N aqueous HCl is added. The solution is immediately frozen and lyophilized for 12 hrs to afford 72 mg (96%) of a white solid, title product: $^{13}C$—NMR ($D_2O$) δ 95.6, 92.2, 72.5, 70.8, 67.0, 66.4, 62.3, 61.1, 59.0, 57.5, 45.2, 44.2, 39.7, 33.6, 32.0, 31.9 and 20.9.

Exact mass calc'd for $C_{26}H_{57}N_3O_6Si_3$: 591.3555; Found: 591.3536.

EXAMPLE 26

N,N'-dibenzyloxycarbonyl-3'-deoxo-3'-methylenespectinomycin oxide (Formula LI: $R_3$ and $R_7$ are as defined in Example 20)

Refer to Chart D.

In 10 ml of $CH_2Cl_2$ is dissolved 1.0 g (1.67 mmol) of N,N'-dibenzyloxycarbonyl-3'-deoxo-3'-methylenespectinomycin. To this solution is added 20 mg (0.075 mmol) of vandadium IV bis(2,4-pentanedionate)oxide, VO(acac)$_2$ followed by 2.56 ml of a 0.625M solution of tert-butyl hydroperoxide in $CH_2Cl_2$. The reaction is stirred 22 hr and 1 ml of tert-butyl hydroperoxide solution is added along with an additional 10 mg of VO(acac)$_2$. The reaction is stirred for 5 hr at which time TLC shows complete reaction. The solution is then poured into 20 ml of 5% aqueous $Na_2SO_3$. The $CH_2Cl_2$ is separated and combined with one 20 ml $CH_2Cl_2$ extract of the aqueous phase. The combined extracts are washed with 20 ml of brine and dried over $Na_2SO_4$. The solution is filtered and the solvent is removed in vacuo to afford 1.07 g of a brown solid. The material is dissolved in $CH_2Cl_2$ and chromatographed on 10 g of silica, slurry packed in 1:1 ethyl acetate/hexane. The column is eluted with 1 liter of 1:1 ethyl acetate. In elution volume 200–1000 ml there is obtained 800 mg (78%) of the title compound as a white solid: $^{13}C$—NMR ($d_6$-Acetone) δ 138.2, 129.2, 128.5, 96.8, 90.8, 75.0, 74.6, 74.5, 69.5, 67.4, 66.5, 65.8, 61.2, 60.2, 59.3, 57.8, 57.5, 47.5, 38.4, 31.8 and 21.3. $^1H$—NMR ($CDCl_3$) δ 1.2 (d, J=6 Hz, $CHCH_3$), 2.0–2.8 ($CH_2$, CH), 3.1 ($NCH_3$'s), 3.4–4.8 (OCH, NCH), 5.2 (anomeric, $OCH_2Ph$) and 7.3 (aromatic); IR ($CHCl_3$), 3412 (m), 3004 (m), 1680 (s), 1477 (m), 1450 (s), 1404 (m), 1384 (m), 1343 (s), 1241 (m), 1164 (s), 1120 (s), 1061 (s) and 886 (m) cm$^{-1}$; $[α]_D$=+3° (C, 0.9265, $CHCl_3$).

Exact mass calc'd for $C_{39}H_{59}N_2O_{11}Si_3$ (m+—$CH_3$): 815.3426; Found: 815.3443.

EXAMPLE 27

N,N'-dibenzyloxycarbonyl-3'-azidomethyldihydrospectinomycin (Formula LIII: $R_3$ and $R_7$ are as in Example 20)

Refer to Chart D.

In 30 ml of 1:5 water/EtOH is dissolved 1.139 g (1.85 mmol) of Example 26 product, 1.53 g (18.5 mmol) of $KN_3$ and 1.0 g (18.6 mmol) of $NH_4Cl$. The resulting solution is heated at 85° C. for 20 min, cooled, and concentrated in vacuo. The residue is partitioned between 30 ml of ethyl acetate and 30 ml of water. The ethyl acetate is separated and combined with one 20 ml ethyl acetate extract. The combined extracts are washed with 15 ml of brine and dried over $Na_2SO_4$. The solution is filtered and the solvent removed in vacuo to afford 975 mg of a light yellow solid. The product is dissolved in $CHCl_3$ and chromatographed on 40 g of silica, slurry-packed in $CHCl_3$. The column was eluted as follows: 100 ml 1% methanol/$CHCl_3$; 1 liter 2% methanol/$CHCl_3$; 1 liter 10% methanol/$CHCl_3$. In elution volume 400–700 ml there is 427 mg of the title compound (35%): $^{13}C$—NMR ($d_6$-Acetone) δ 138.1, 129.2, 128.8, 128.4, 94.5, 92.6, 75.3, 74.4, 73.8, 67.3, 66.4, 65.4, 61.2, 61.0, 60.4, 57.7, 57.6, 57.3, 55.7, 39.2, 31.5 and 21.1; $^1$H-NMR ($d_6$-Acetone) δ 1.2 (d, J=6 Hz, $CHCH_3$) 1.3–1.9 ($CH_2$), 3.1 ($NCH_3$); 3.5–4.8 (OCH, NCH); 5.1 (anomeric, $OCH_2Ph$); 5.8 ($CH_2N_3$) and 7.3 (aromatic); IR ($CHCl_3$) 3563 (m), 3450 (m), 3015 (s), 2978 (m), 2936 (m), 2112 (s), 1690 (s), 1485 (s), 1452 (s), 1406 (s), 1383 (s), 1344 (s), 1205 (s), 1169 (s), 1124 (s), 1108 (s), 1080 (s), 1056 (s) and 723 (s) cm$^{-1}$; $[\alpha]_D = -7°$ (C, 0.994, $CHCl_3$).

Exact mass calc'd for $C_{39}H_{60}N_5O_{11}Si_3$ (M+—$CH_3$): 858.3597; Found: 858.3578.

EXAMPLE 28

3-S-3'-aminomethyldihydrospectinomycin trihydrochloride (Formula LXI: $R_3$ is methyl)

Refer to Chart E.

In 5 ml of methanol is dissolved 100 mg (0.152 mmol) of N,N'-dibenzyloxycarbonyl-3'-azidomethyldihydrospectinomycin. Example 27. To this solution is added 100 mg of Pd and 61 μl (1.52 mmol) of formic acid. The reaction was stirred for 10 min, was filtered and the solvent is removed in vacuo to afford 79 mg of a clear glass. The product is taken up in water and 4.6 ml (0.46 mmol) of 0.1N aqueous HCl is added. The sample is frozen and lyophilized overnight to afford 62 mg (86%) of a white solid: $^{13}C$—NMR ($D_2O$) δ 93.5, 92.6, 72.5, 70.6, 68.0, 66.8, 62.3, 61.1, 59.0, 44.4, 38.8, 32.1, 31.8 and 20.6.

EXAMPLE 29

N,N'-dibenzyloxycarbonyl-3'-(cyanomethyl)dihydrospectinomycin (Formula LV: $R_3$ and $R_7$ are as in Example 20)

Refer to Chart D.

In 100 ml of 1:5 water/EtOH is combined 1.0 g (1.62 mmol) of Example 26 product, 1.05 g (16.2 mmol) of KCN and 866 mg of $NH_4Cl$. The reaction is stirred for 5 hr at room temperature, after which the reaction appears complete by TLC. The ethyl acetate is removed in vacuo and the residue partitioned between ethyl acetate and water. The ethyl acetate is separated and combined with one, 15-ml extract of the aqueous phase. The combined extracts are washed with 25 ml of brine and dried over $NaSO_4$. After filtering, the solvent is removed in vacuo to afford 959 mg of a white solid. The product is taken up in $CHCl_3$ and chromatographed on 100 g of silica, slurry packed in $CHCl_3$. The column is eluted as follows: 1 L 1% methanol/$CHCl_3$; 1 L 2% methanol/$CHCl_3$; 1 L 3% methanol/$CHCl_3$; 1 L 4% methanol/$CHCl_3$; 1 L 5% methanol/$CHCl_3$; 2 L 10% methanol/$CHCl_3$. In elution volume 1890 ml to 2835 ml there is obtained 254 mg of epoxide. In elution volume 3510 ml to 4410 ml there is obtained 156 mg of the title compound (19.7% yield based on recovered epoxide): $^{13}C$—NMR ($d_6$-Acetone) δ 138.2, 138.1, 129.2, 128.5, 118.2, 94.5, 92.1, 74.4, 74.2, 73.8, 73.7, 73.3, 67.3, 66.4, 65.7, 61.2, 61.1, 57.8, 57.7, 57.4, 57.3, 40.6, 31.7, 31.6, 24.9 and 20.9. Mass spec (di-TMS deriv) m/e 785 (M+) 512 455, 299, 276, 247, 199, 149, 131, 116, 97, 85, 73 and 57.

EXAMPLE 30

3'-(cyanomethyl)dihydrospectinomycin dihydrochloride

Refer to Chart D.

In 2 ml of methanol is dissolved 37 mg (0.057 mmol) of N,N'-dibenzyloxycarbonyl-3'-(cyanomethyl)dihydrospectinomycin. To this solution is added 50 mg of Pd followed by 23 μl of formic acid. The reaction is stirred for 2 min and is filtered. Removal of the solvent in vacuo affords 25 mg of a white solid. The product is dissolved in 10 ml of 0.1N HCl and lyophilized to afford 28 mg of a white solid (100%). $^{13}C$—NMR ($D_2O$) δ 120.3, 94.0, 92.8, 73.7, 71.1, 68.7, 67.2, 62.7, 61.6, 59.4, 40.5, 32.4, 32.0, 25.5 and 20.9.

Exact mass calc'd for $C_{28}H_{59}N_3O_7Si_4$ (tetra—TMS deriv): 661.3430; Found: 661.3407.

EXAMPLE 31

N,N'-dibenzyloxycarbonyl-3-(S)-3'-aminomethyldihydrospectinomycin (Formula LXIII: $R_3$ and $R_7$ are as in Example 20)

Refer to Chart E.

In a Paar hydrogenation bottle is combined 406 mg (0.63 mmol) of N,N'-dibenzyloxycarbonyl-3'-(S)-3'-(azidomethyl)dihydrospectinomycin (Example 27) and 404 mg of $PtO_2$ and 10 ml of isopropanol. The solution is hydrogenated at 10 psi for 1.5 hr. The solution is then filtered through magnesium silicate and the solvent removed in vacuo to afford 367 mg of a title product as a solid. The product is taken up in 5% methanol/$CHCl_3$ and filtered through 3 g of silica with 100 ml of 10% methanol/$CHCl_3$. Removal of the solvent in vacuo affords 273 mg of an off-white solid: $^{13}C$—NMR ($d_4$-methanol) 138.1, 129.5, 129.0, 128.8, 94.8, 93.7, 74.7, 73.3, 68.3, 67.7, 66.8, 65.7, 61.2, 57.9, 46.9, 40.0, 31.8 and 21.2 ppm.

EXAMPLE 32

N,N'-dibenzyloxycarbonyl-3'-(R)-3'-aminomethyldihydrospectinomycin (Formula LXIV: $R_3$ and $R_7$ are as in Example 20)

Refer to Charts D and E.

A. In 20 ml of methanol is dissolved 1.09 g (1.67 mmol) of N,N'-dicarbobenzyloxy-3'-deoxo-3'-methylenespectinomycin (Example 20) and 531 mg (5.0 mmol) of $Na_2CO_3$. To this solution is added 0.2 ml of 30% $H_2O_2$. The reaction is stirred at room temperature for 10.5 hr, at which time TLC shows complete reaction. The reaction is poured into 50 ml of water and extracted with ethyl acetate (2×30 ml). The combined extracts are washed with 30 ml of brine and dried over $Na_2SO_4$. After filtering, removal of the solvent in vacuo affords 1.027 g of a white solid. The product is taken up in $CH_2Cl_2$ and chromatographed on 75 g of silica slurry packed in 1:1 ethyl acetate/hexane. The column is eluted as follows with 30 ml factions taken: 700 ml, 1:1 ethyl acetate/hexane; 2 1 6:4 ethyl acetate/hexane and 500 ml 7:3 ethyl acetate/hexane. Elution volume 990–1680 ml contained 503 mg of a white solid which contains β-epoxide (Formula LI), approximately 1:1. Elution volume 1830 ml to 3090 ml contains 186 mg of pure α-epoxide (formula LII). (18% yield): $^{13}C$—NMR ($d_6$-Acetone) 138.2, 129.1, 128.4, 96.4, 91.6, 74.9, 74.5, 69.6, 67.2, 66.4, 65.4, 60.5, 60.2, 57.5, 50.8, 38.1, 31.7 and 21.3.

B. The formula LII α-epoxide of part A (90 mg, 0.146 mmol) is dissolved in 4 ml of ethanol and potassium azide (113 mg, 1.4 mmol), ammonium chloride (53 mg, 1.0 mmol) and water (1.0 ml) are added. The mixture is stirred 5.5 hrs at 50° C. under a nitrogen atmosphere, and then 16 hrs at room temperature. The solvent is then removed in vacuo and 50 ml of ethyl acetate and 5 ml of water are added. The organic layer is washed with brine and dried over magnesium sulfate. Removal of solvent in vacuo yields 93 mg (0.142 mmol, 97%) of N,N'-dibenzyloxycarbonyl-3'-(R)-3'-azidomethyl-3'-dihydrospectinomycin (formula LIV) as a white solid: $^{13}C$ NMR ($d_6$-acetone) δ 157.5, 138.5, 129.2, 128.7, 128.4, 95.0, 92.9, 76.6, 74.7, 74.4, 67.5, 67.3, 66.4, 65.5, 60.9, 57.7, 54.5, 39.9, 31.8, 21.5; IR ($CHCl_3$) 3576, 3381, 3065, 3006, 2936, 2908, 2469, 2189, 1484, 1406, 1384, 1282, 1240, 1221, 1025, 1000, 951, 912, 600 cm$^{-1}$; Rf=0.47 (silica gel, 10% methanol/chloroform).

C. Azide of part B, (1.49 g, 2.27 mmol) is dissolved in 30 ml of isopropyl alcohol, 1.3 g of $PtO_2$ is added and the mixture is hydrogenated at 10 psi for 2 hr. An additional 1.0 g of $PtO_2$ is added and the hydrogenation is continued for an additional 2 hr. The mixture is filtered through diatomaceous earth and magnesium silicate and solvent is removed in vacuo to afford 960 mg of a brown solid. The product is chromatographed on 40 g of 230–400 mesh silica gel packed with 1% methanol/$CHCl_3$ and eluted with 200 ml of 2% methanol/$CHCl_3$, 200 ml of 3% methanol/$CHCl_3$, 1 liter of 5% methanol/$CHCl_3$, 2 liters of 7% methanol/$CHCl_3$ and the remainder 10% methanol/$CHCl_3$, collecting 35 ml fractions. Fractions 88–126 are pooled on the basis of TLC to afford 370 mg (0.59 mmol, 26%) of title product as an off-white solid: $^{13}C$—NMR (methanol-$d_4$) δ 159, 138.0, 129.4, 128.8, 128.6, 96.2, 94.2, 74.6, 73.6, 68.1, 66.7, 65.4, 60.7, 58.0, 45.5, 41.6, 31.7 and 21.5.

EXAMPLE 33

N,N'-dibenzyloxycarbonyl-3'-(R)-3'-(N-ethylaminomethyl)dihydrospectinomycin (Formula LXVI: $R_3$ and $R_7$ are as in Example 20, $R_{63}$ is ethyl and $R_{64}$ is hydrogen)

Refer to Chart E.

In 5 ml of methanol is dissolved 591 mg (0.78 mmol) of N,N'-dibenzyloxycarbonyl-3'-(R)-3'-aminomethyldihydrospectinomycin (Example 32). To this solution is added 0.43 ml (7.8 mmol) of acetaldehyde and a trace of methyl orange indicator in methanol. Then 16.3 mg (0.26 mmol) of $NaCNBH_3$ in 1 ml of methanol is added. The pH is adjusted by addition of 1N methanolic HCl. The reaction is stirred for 1 hr and concentrated in vacuo. The residue is partitioned between water and ethyl acetate. The aqueous phase is made alkaline with concentrated $NH_4OH$ and the ethyl acetate is separated. The aqueous phase is extracted again with ethyl acetate (1×20 ml) and the combined extracts are washed with brine (1×30 ml and dried over $MgSO_4$. After filtering, the solvent is removed in vacuo to afford 409 mg of a white solid, title product. The product is taken up in $CHCl_3$ and chromatographed on 20 gm of silica, slurry-packed in $CHCl_3$. The column is eluted as follows: 100 ml 1% methanol/$CHCl_3$; 100 ml 2% methanol/$CHCl_3$; 100 ml 3% methanol/$CHCl_3$; 100 ml 4% methanol/$CHCl_3$; 500 ml 5% methanol/$CHCl_3$; and 500 ml 7% methanol/$CHCl_3$. In elution volume 650–1000 ml there is recovered 123 mg of the title compound as a white solid:

$^{13}C$—NMR ($d_6$-Acetone) 138.1, 129.1, 128.3, 128.1, 97.0, 93.8, 74.5, 71.6, 67.1, 66.4, 65.2, 57.6, 54.0, 44.4, 43.8, 31.6, 21.5 and 14.9 ppm.

Exact mass calc'd for $C_{34}H_{77}N_3O_{11}Si_4$ (tetra—TMS): 947.4635; Found: 947.4601.

EXAMPLE 34

N,N'-dibenzyloxycarbonyl-3'-(R)-3'-(N-octylaminomethyl)dihydrospectinomycin (Formula LXVI: $R_3$ and $R_7$ are as in Example 20 and $R_{63}$ is n-octyl and $R_{64}$ is hydrogen)

Refer to Chart E.

In 5 ml of methanol are combined 500 mg (0.79 mmol) of N,N'-dibenzyloxycarbonyl-3'-(R)-3'-aminomethyldihydrospectinomycin, (Example 32) 1.23 ml of n-octanal and trace of methyl orange indicator. To this solution is added 16.5 mg (0.26 mmol) of $NaCNBH_3$ in 1 ml of methanol. The pH is adjusted to 4 with 1N NCl/methanol and the reaction is stirred for 30 min. The reaction is concentrated in vacuo and the residue is taken up in ethyl acetate. The solution was washed with water (2×20 ml), combined with 1, 10 ml ethyl acetate backwash and washed with brine (1×30 ml). After drying over $MgSO_4$, the solution is concentrated to an oil. The oil is taken up in $CHCl_3$ and chromatographed on 33 g of silica, slurry packed in $CHCl_3$. The column is eluted as follows: 200 ml $CHCl_3$; 500 ml 1% methanol/$CHCl_3$; 1 liter 2% methanol/$CHCl_3$; 500 ml 3% methanol/$CHCl_3$; and 500 ml 5% methanol/$CHCl_3$. Elution volume 900–1400 ml contains 165 mg of the title compound as a white solid: $^{13}C$—NMR ($d_6$-Acetone) 138.2, 138.1, 129.1, 128.3, 97.0, 93.8, 74.6, 71.7, 67.1, 66.5, 65.2, 61.1, 57.6, 49.8, 44.5, 32.4, 32.1, 31.6, 30.8, 30.0, 27.8, 23.2, 21.5 and 14.3 ppm.

Exact mass calc'd for $C_{50}H_{86}N_3O_{11}Si_4$ (tetra—TMS—$CH_3$): 1016.5339; Found: 1016.5327.

EXAMPLE 35

3'-(R)-3'-(N-ethylaminomethyl)dihydrospectinomycin trihydrochloride

Refer to Chart E.

In 10 ml of methanol is dissolved 123 mg (0.19 mmol) of N,N'-dibenzyloxycarbonyl-3'-(R)-3'-(N-ethylaminomethyl)dihydrospectinomycin (Example 33). To this solution is added 123 mg of Pd black followed by 72 μl of formic acid. The reaction is stirred for 20 min, filtered and concentrated in vacuo to afford a white solid. The product is taken up in water and 1 ml of 1N HCl is added. The solution is frozen and lyophilized to afford 83 mg (89% yield) of title product, a white solid: $^{13}C$—NMR ($D_2O$) 94.0, 93.2, 73.2, 70.4, 68.2, 66.8, 66.2, 62.4, 60.5, 59.3, 50.5, 45.1, 40.7, 31.9, 31.5, 21.0, and 11.1 ppm.

Exact mass calc'd for $C_{35}H_{81}N_3O_{11}Si_6$ (hexa—TMS): 823.4690; Found: 823.4665.

EXAMPLE 36

3'-(R)-3'-(N-octylaminomethyl)dihydrospectinomycin trihydrochloride

Refer to Chart E.

In 5 ml of methanol are combined 153 mg (0.21 mmol) of N,N'-dibenzyloxycarbonyl-3'-(R)-3'-(N-octylaminomethyl)dihydrospectinomycin (Example 34) and 153 mg of Pd black. To this mixture is added 80 μl (2.1 mmol) of formic acid. The reaction is stirred for 20 min, filtered and concentrated in vacuo to afford 124 mg of a white solid. The product is taken up in water and 1 ml of 1N HCl is added. The solution is frozen and lyophillized to afford 111 mg of title product a white solid (90% yield): $^{13}C$—NMR ($D_2O$) 91.1, 89.2, 69.2, 66.5, 64.2, 62.8, 62.2, 58.4, 56.5, 55.3, 46.9, 45.7, 36.8, 28.3, 28.2, 27.8, 27.5, 25.4, 22.9, 21.9, 19.1, 17.0 and 10.5 ppm.

Exact mass calc'd for $C_{41}H_{93}N_3O_{11}Si_6$ (hexa—TMS): 907.5629; Found: 907.5627.

EXAMPLE 37

N,N'-dibenzyloxycarbonyl-3'-(S)-3'-(N-ethylaminomethyl)dihydrospectinamycin (Formula LXV: $R_3$ and $R_7$ are as in Example 20 and $R_{63}$ and $R_{64}$ are as in Example 33)

Refer to Chart E.

In 6 ml of methanol are combined 500 mg (0.774 mmol) of N,N'-dibenzyloxycarbonyl-3'-(S)-3'-(aminomethyl)dihydrospectinomycin (Example 31), 44 μl (0.774 mmol) of acetaldehyde and a trace of methyl orange indicator in methanol. To this solutions is then added 16.2 mg (0.258 mmol, 0.774 mmol $H^-$) of NaCNBH$_3$ in 1 ml of methanol. The pH is adjusted with the addition of 1N methanolic HCl until the indicator is just pink. The reaction is then stirred at room temperature and additional 1N HCl/methanol is added to keep the indicator pink. After 2.5 hr the methanol is removed and the residue partitioned between water and ethyl acetate. The aqueous phase is made alkaline with 1N NaOH and the ethyl acetate is then separated. The aqueous phase is extracted again with ethyl acetate (2×30 ml). The combined organics are washed with brine (1×50 ml) and dried over MgSO$_4$. After filtering, the solvent is removed in vacuo to afford 458 mg of a white solid. The product is taken up in CHCl$_3$ and chromatographed on 20 gm of silica gel, slurry packed in CHCl$_3$. The column is eluted as follows: 100 ml, 1% methanol/CHCl$_3$; 100 ml 2% methanol/CHCl$_3$; 100 ml 3% methanol/CHCl$_3$; 100 ml 5% methanol/CHCl$_3$; 100 ml 7% methanol/CHCl$_3$; and 700 ml 10% methanol/CHCl$_3$. In elution volume 520–720 ml there is contained 306 mg of the title compound as a white solid (60% yield):

$^{13}C$—NMR (d$_6$-Acetone) 138.1, 129.1, 128.3, 94.2, 74.4, 73.1, 67.2, 66.6, 65.1, 57.6, 57.5, 57.3, 55.7, 45.0, 40.3, 31.4, 21.1, and 15.3 ppm.

Exact mass calc'd for $C_{41}H_{66}N_3O_{11}Si_3$ (tri—OTMS,—CH$_3$: 860.4005; Found: 860.4008.

EXAMPLE 38

3'-(S)-3'-(N-ethylaminomethyl)dihydrospectinomycin trihydrochloride

Refer to Chart E.

In 10 ml of methanol are combined 294 mg (0.44 mmol) of N,N'-dibenzyloxycarbonyl-3'-(S)-3'-(N-ethylaminomethyl)dihydrospectinomycin (Example 37) and 200 mg of Pd black. To this solution is added 170 μl of formic acid. The reaction is stirred for 40 min and is filtered. Removal of the solvent in vacuo affords 225 mg of a white solid. The product is dissolved in 2 ml of water and 1.5 ml of 1N HCl is added. The solution is frozen and lyophillized to afford 215 mg of a white solid (97.5% yield): $^{13}C$—NMR ($D_2O$) 96.3, 95.1, 75.5, 74.2, 70.6, 70.5, 70.3, 65.5, 65.0, 62.2, 54.5, 47.6, 41.7, 35.3, 34.6, 23.2 and 13.79 ppm.

Exact mass calc'd for $C_{35}H_{81}N_3O_7Si_6$ (hexa TMS): 823.4690 Found: 823.4690.

EXAMPLE 39

N,N'-dibenzyloxycarbonyl-3'-(S)-3'-(N-butylaminomethyl)dihydrospectinomycin (Formula LXV: $R_3$ and $R_7$ are as in Example 20 and $R_{63}$ is butyl and $R_{64}$ is hydrogen)

Refer to Chart E.

In 10 ml of methanol is dissolved 507 mg (0.803 mml) of N,N'-dibenzyloxycarbonyl-3'-(S)-3'-(aminomethyl)-dihydrospectinomycin, (Example 31). To this solution is added 0.71 ml of n-butyraldehyde and a drop of methyl orange indicator in methanol. This is followed by the addition of 17 mg of NaCNBH$_3$ in 1 ml of methanol. The pH is adjusted to 4 with the addition of 1N HCl/methanol. The pH is maintained at 4 for 0.5 hr while the reaction is stirred. The methanol is then removed in vacuo and the residue partitioned between ethyl acetate and water. The ethyl acetate is separated and combined with 1, 25 ml ethyl acetate extract of the aqueous phase. The combined extracts are washed with 50 ml of brine and dried over MgSO$_4$. After filtering, removal of the solvent affords 616 mg of a white solid. The product is taken up in CHCl$_3$ and chromatographed on 30 g of silica gel, slurry packed in CHCl$_3$. The column is eluted as follows: 100 ml 1% methanol/CHCl$_3$; 100 ml 2% methanol/CHCl$_3$; 100 ml 3% methanol/CHCl$_3$; 100 ml 4% methanol/CHCl$_3$; 1.3 liter 5% methanol/CHCl$_3$. In elution volume 850–1400 ml there is recovered 250 mg of the title compound as a white solid: (45.3% yield): $^{13}C$—NMR (d$_6$-Acetone) 138.2, 129.2, 128.4, 94.2, 74.5, 73.1, 67.3, 66.7, 65.2, 57.6, 57.5, 55.9, 50.5, 40.3, 32.5, 31.6, 21.2, 20.9 and 14.2 ppm.

Exact mass calc'd for $C_{46}H_{78}N_3O_{11}Si_4$ (tetra TMS—CH$_3$: 960.4713; Found: 960.4722.

EXAMPLE 40

3'-(S)-3'-(N-butylaminomethyl)dihydrospectinomycin trihydrochloride

Refer to Chart E.

In 10 ml of methanol is dissolved 245 mg (0.39 mmol) of N,N'-dibenzyloxycarbonyl-3'-(S)-3'-(N-butylaminomethyl)dihydrospectinomycin (Example 39). To this solution is added 250 mg of Pd black followed by 152 μl of formic acid. The reaction is stirred for 45 min and is filtered. Removal of the solvent in vacuo affords 195 mg of a white solid. The material is taken up in 2 ml of water and 1.5 ml of 1N HCl is added.

The solution is frozen and lyophillized to afford 166 mg of a white solid (80% yield): $^{13}$C—NMR (D$_2$O) 96.2, 95.3, 75.6, 73.4, 70.8, 69.7, 69.5, 65.1, 63.9, 61.7, 54.9, 52.4, 41.7, 34.8, 34.6, 30.8, 23.4, 22.9 and 16.6 ppm.

Exact mass calc'd for C$_{37}$H$_{85}$N$_3$O$_7$Si$_6$ (Hexas—TMS): 851.5003; Found: 851.4980;

Exact mass calc'd for C$_{36}$H$_{82}$N$_3$O$_7$Si$_6$ (Hexa—TMS—CH$_3$): 836.4768; Found: 836.4757.

EXAMPLE 41

N,N'-dibenzyloxycarbonyl-3'-(S)-3'-(N-octylaminomethyl)dihydrospectinomycin (Formula LXV: R$_3$ and R$_7$ are as in Example 20 and R$_{63}$ and R$_{64}$ are as in Example 34)

Refer to Chart E.

In 5 ml of methanol is dissolved 500 mg (0.79 mmol) of N,N'-dibenzyloxycarbonyl-3'-(S)-3'-(aminomethyl)-dihydrospectinomycin (Example 31). To this solution is added 1.23 ml of n-octanal and a drop of methyl orange/methanol solution. Then 17 mg of NaCNBH$_3$ in 1 ml of methanol is added. The pH is lowered to 4 with 1N HCl/methanol. The reaction is stirred for 1 hr, maintaining the pH at 4. The methanol is then removed in vacuo and the residue is taken up in CHCl$_3$. The solution is washed with 5 ml of brine and dried over MgSO$_4$. After filtering, the solvent is removed to afford an oil. The product is taken up in CHCl$_3$ and chromatographed on 30 g of silica, slurry packed in CHCl$_3$. The column is eluted as follows: 200 ml CHCl$_3$; 500 ml 1% methanol/CHCl$_3$; 1 liter 2% methanol/CHCl$_3$; 500 ml 3% methanol/CHCl$_3$; 1 liter 5% methanol/CHCl$_3$. In elution volume 1100–1400 ml there is recovered 186 mg of the title compound as a white solid (32% yield): $^{13}$C—NMR (d$_6$-Acetone) 138.2, 129.2, 128.4, 94.2, 74.5, 74.2, 74.1, 72.9, 67.3, 66.7, 66.5, 65.2, 61.4, 61.1, 60.6, 60.5, 57.6, 57.4, 55.8, 50.8, 40.4, 32.5, 31.5, 30.8, 30.3, 30.1, 29.9, 27.8, 23.2, 21.2, and 14.3 ppm.

Exact mass calc'd for C$_{51}$H$_{89}$N$_3$O$_{11}$Si$_4$ (tetra TMS): 1031.5574; Found: 1031.5585.

EXAMPLE 42

3'-(S)-3'-(N-octylaminomethyl)dihydrospectinomycin trihydrochloride

Refer to Chart E.

In 5 ml of methanol is dissolved 180 mg of N,N'-dibenzyloxycarbonyl-3'-(S)-3'-(N-octylaminomethyl)-dihydrospectinomycin. To this solution is added 200 mg of Pd black followed by 94 μl of formic acid. The reaction is stirred for 30 min and is filtered. The solvent is removed in vacuo to afford 150 mg of a white solid. The product is taken up in 2 ml of water and 0.8 ml of 1N HCl is added. The solution is frozen and lyophillized overnight to afford 135 mg of a white solid (96% yield): $^{13}$C—NMR (D$_2$O) 96.2, 95.3, 75.6, 73.4, 70.6, 69.7, 69.5, 65.1, 63.9, 61.7, 54.9, 50.7, 41.8, 34.8, 34.6, 32.0, 29.5, 28.8, 25.8, 23.4, and 17.2 ppm.

Exact mass calc'd for C$_{14}$H$_{93}$N$_3$O$_7$Si$_6$ (hexa TMS): 907.5629; Found: 907.5618.

EXAMPLE 43

3'-(R)-3'-aminomethyldihydrospectinomycin trihydrochloride (Formula LXII: R$_3$ is methyl)

The azide of Example 32, part B, (36 mg, 0.055 mmol) is dissolved in 0.5 ml of methanol and 36 mg of palladium black is added followed by 21 μl (0.55 mmol) of formic acid. The mixture is stirred 10 min at room temperature, and filtered, rinsing the catalyst with four portions of methanol. The filtrate is concentrated in vacuo to afford a colorless material which is dissolved in 5 ml of water and treated with 0.18 ml (0.18 mmol) of 1N HCl. Lyophillization affords 30 mg of the title product as a white solid. $^{13}$C—NMR (D$_2$O, CH$_3$CN internal reference) δ 94.3, 93.6, 73.0, 70.7, 68.4, 67.0, 66.3, 62.6, 60.7, 59.5, 43.4, 40.8, 31.9, 31.6 and 21.1.

EXAMPLE 44

3'-(S)-3'-(n-propylaminomethyl)-3'-dihydrospectinomycin trihydrochloride

A. In 5 ml of freshly distilled propylamine is dissolved 93 mg (0.151 mmol) of formula LI β-epoxide of Example 32, part A. The resulting solution is refluxed for 2 hr at which time TLC shows complete loss of starting material, with the formation of one more polar, ninhydrin active product. The PrNH$_2$ is removed in vacuo and the residue is stripped down twice from ethyl acetate. The product is then placed on the hi-vacuum pump for 2 hr. This affords 84 mg of a white solid (83% yield). $^{13}$C—NMR (d$_6$-Acetone) 138.2, 129.1, 128.3, 94.2, 74.9, 74.4, 74.0, 73.0, 67.2, 66.7, 66.5, 66.3, 65.1, 64.7, 60.3, 57.5, 57.4, 55.8, 52.5, 40.2, 31.5, 23.4, 21.2 and 11.9 δ.

B. In 5 ml of methanol is dissolved 80 mg (0.12 mmol) of N,N'-dicarbobenzyloxy-3'-(n-propylaminomethyl)-dihydrospectinomycin, reaction product of part A. To this solution is added 93 mg of palladium black and 46 μl of formic acid. The reaction is stirred for 30 min, filtered, and the solvent removed in vacuo to afford 73 mg of a white solid. The product is taken up in 1 ml of water and 4 ml of 0.1N HCl is added. The sample is frozen and lyophillized to afford 71 mg of a white solid (100%): $^{13}$C—NMR (D$_2$O) 92.6, 91.7, 71.9, 69.8, 67.0, 66.1, 65.9, 61.5, 60.3, 58.0, 51.4, 50.5, 38.2, 31.2, 19.9, 18.8, and 10.4 δ.

Exact mass calc'd for C$_{29}$H$_{64}$M$_3$O$_7$Si$_4$ (M+—CH$_3$): 678.3821; Found: 678.3791.

EXAMPLE 45

3'-R-3'[(3-dimethylaminopropyl)-aminomethyl]-dihydrospectinomycin tetrahydrochloride A. The epoxide (600 mg, 0.98 mmol, Example 32, part A) is dissolved in 5 ml of 3-dimethylaminopropylamine and heated at 60° for 71 hr. The excess is removed in vacuo and the residue is dissolved in 75 ml of EtOAc which is extracted with 2×5 ml of H$_2$O and 25 ml of brine, dried with MgSO$_4$ and concentrated to give 600 mg of pale yellow solid. The product is chromatographed on 30 g of 230–400 mesh silica gel packed with 5% MeOH/CHCl$_3$ and eluted with 500 ml of 5% MeOH/CHCl$_3$ with 0.5% NH$_4$OH, 1 L of 10% MeOH/CHCl$_3$ with 1% NH$_4$OH and the rest 20% MeOH/CHCl$_3$ with 1% NH$_4$OH collecting 30 ml fractions. Pooling of fractions 29–56 yields 235 mg (0.33 mmol, 33%) of product as an off while solid: R$_f$=0.22 (silica gel, 20% MeOH/CHCl$_3$ with 1% NH$_4$OH); $^{13}$C—NMR (CD$_3$COCD$_3$) δ 157, 138.2, 129.1, 128.4, 96.9, 93.8, 74.6, 74.2, 71.8, 67.1, 66.4, 66.2, 60.5, 58.1, 57.6, 54.4, 48.1, 45.4, 44.2, 31.7, 27.3, 21.5; MS exact mass for M+—CH$_3$ on tetrakistrimethylsilyl derivative, C$_{47}$H$_{81}$N$_4$O$_{11}$Si$_4$. Calc'd: 989.4979. Found: 989.4968. MS 1004, 989, 493, 449, 359, 305, 273, 187, 115, 91, 58.

B. To a solution of 230 mg (0.32 mmol) of the reaction product of part A in 5 ml of methanol is added 150 mg of palladium black and 0.12 ml (3.2 mmol) of formic acid. The mixture is stirred 3 hr at room temperature and filtered rinsing the catalyst with methanol. The solvent is removed in vacuo and the residue is dissolved in H$_2$O and treated with 1.4 ml (1.4 mmol) of 1N HCl. Lyophilization yields 200 mg (0.33 mmol), 100%) of product as an off white solid: R$_f$=0.77 (silica gel, CHCl$_3$/MeOH/NH$_4$OH, 3/4/2); $^{13}$C NMR (D$_2$O, CH$_3$CN internal reference) δ 94.1; 93.2, 73.3, 70.5, 68.2, 66.9, 66.2, 62.4, 60.6, 59.3, 55.2, 51.4, 46.4, 43.9, 40.8, 31.9, 31.5, 21.7, 21.0; MS (hexakistrimethylsilyl derivative) 880 (M+), 865, 791, 273, 243, 230, 217, 187, 145, 116, 73, 58; exact mass for M+—CH$_3$, C$_{37}$H$_{85}$N$_4$O$_7$Si$_6$. Calc'd: 865.5034. Found, 865.5037.

EXAMPLE 46

N,N'-dicarbobenzyloxy-3'-(R)-3'-(n-butylaminomethyl)-3'-dihydrospectinomycin (Formula LVIII: R$_{62}$ is n-butyl and R$_3$, R$_7$ and R$_{61}$ are as in Example 44)

Refer to Chart D.

The formula LII α-epoxide of Example 32, part A (40 mg. 0.065 mmol) is dissolved in 2.0 ml of n-butylamine and warmed to 60° with protection from atmospheric moisture for 18 hr. The solvent is removed in vacuo, 5 ml of ethyl acetate is added and the solvent is removed again. The residue is purified by chromatography on a 20×20 cm 250μ silica gel preparative TLC plate with 254 mm phosphor, eluted with 10% methanol/CHCl$_3$. The band with Rf 0.6–0.75 (visualized by short wave UV light) is collected and the product is washed off of the silica gel with ethyl acetate. Concentration in vacuo gives 28 mg (0.040 mmol, 63%) of title product. $^{13}$C—NMR (d$_6$-Acetone) δ 157, 138.2, 129.1, 128.3, 128.1, 97.1, 93.8, 74.6, 74 (broad), 71.7, 67.1, 66.4, 65.2, 61.0, 60.2, 57.6, 54.4, 49.3, 44.5, 32.1, 31.6, 21.5, 20.8, 14.2; Rf=0.5 (silica gel, 10% methanol/CHCl$_3$); MS (for tetratrimethylsilyl derivative) m/z 975, 960, 800, 709, 675, 620, 545, 493, 449, 359, 305, 273, 91.

Exact mass for M+—CH$_3$ calc'd for C$_{46}$H$_{78}$N$_3$O$_{11}$Si$_4$: 960.4713; Found: 960.4703.

EXAMPLE 47

3-(R)-3'-(n-butylaminomethyl)-3'-dihydrospectinomycin trihydrochloride.

Refer to Chart D.

The Example 46 product is dissolved in 0.5 ml of methanol and 30 mg of palladium black is added followed by 22 μl (0.58 mmol) of 95% formic acid. The mixture is stirred 1 hr at room temperature and filtered, rinsing the catalyst with three portions of methanol. The solvent is removed in vacuo and the residue is dissolved in 4 ml of water. The pH is adjusted to 1.5 with 1N HCl and the solution was lyopholized to afford 21.5 mg of title product as a white solid:

$^{13}$CNMR (D$_2$O, CH$_3$CN reference) δ 94.1, 93.3, 73.3, 70.5, 68.3, 66.9, 66.2, 62.5, 60.6, 59.4, 51.0, 49.5, 40.9, 31.9, 31.5, 27.9, 21.0, 20.1, 13.9; Rf=0.85 (silica gel, CHCl$_3$/methanol/NH$_4$OH, 3:4:2); MS (for tetrakis-trimethylsilyl derivative) m/z 707, 692, 621, 349, 273, 171, 158, 145, 86, 73. Exact mass for M+—CH$_3$, calc'd for C$_{30}$H$_{66}$N$_3$O$_7$Si$_4$; 692.3978. Found 692.3967.

EXAMPLE 48

N,N'-dibenzyloxycarbonyl-3'-(S)-spectinomycin cyanohydrin (Formula LXVII: R$_3$ and R$_1$ are as in Example 1)

Refer to Chart F.

In 25 ml of methanol are combined 5.0 gm (8.33 mmol) of N,N'-dibenzyloxycarbonylspectinomycin and 0.76 ml (8.33 mmol) of acetone cyanohydrin. To this solution is then added 100 mg (0.72 mmol) of K$_2$CO$_3$. The reaction is stirred for 4.5 hr and then concentrated in vacuo. The residue is taken up in 40 ml of ethyl acetate, washed once with 50 ml brine and dried over Na$_2$SO$_4$. The solution is then filtered and concentrated in vacuo to afford 5.0 gm of a white solid. The product is taken up in CHCl$_3$ and chromatographed on 200 gm of silica, slurry packed in CHCl$_3$. The column is eluted as follows: 1 L 1% methanol/CHCl$_3$; 1 L 2% methanol/CHCl$_3$; 2 L 4% methanol/CHCl$_3$; 2 L 5% methanol/CHCl$_3$. In elution volume 3.3 L to 6.0 L is found 3.92 g of the title compound (75% yield): $^{13}$C—NMR (d$_4$-methanol) 138.1, 138.0, 129.4, 129.2, 128.8, 128.4, 94.4, 91.1, 74.8, 74.6, 74.5, 73.3, 68.2, 66.8, 66.4, 66.2, 60.9, 57.8, 42.1, 31.7 and 20.6 ppm; [α]$_D$ +4° (C, 0.8935, CHCl$_3$).

Mass spec m/e 816, 801, 745, 629, 493, 449, 359, 305, 270, 170, 144, 91 and 73.

EXAMPLE 49

3'-(S)-Spectinomycin cyanohydrin diformate

Refer to Chart F.

In 5 ml of methanol is dissolved 200 mg (0.32 mmol) of N,N-dicarbobenzyloxy-spectinomycin cyanohydrin. To this solution is added 200 mg of Pd black followed by 120 μl (3.2 mmol) of formic acid. The reaction is stirred for 0.5 hr and is filtered. Removal of the solvent in vacuo afforded 170 mg of title product, a white solid: $^{13}$C—NMR (D$_2$O) 93.5, 91.3, 73.0, 71.3, 68.2, 67.5, 67.4, 67.2, 62.7, 59.6, 41.3, 33.6, 32.0, and 20.6.

EXAMPLE 50

N,N'-dibenzyloxycarbonyl-3'-(S)-3'-(aminomethyl)-dihydrospectinomycin (Formula LXIII: R$_1$ and R$_3$ are as in Example 48)

Refer to Chart F.

In 10 ml of acetic acid is dissolved 3.33 g (5.31 mmol) of N,N'-dibenzyloxycarbonylspectinomycin-3'-(S)-cyanohydrin, Example 48. The solution is added to a Paar bottle containing 5.0 g of wet Raney nickel. The solution is then hydrogenated for 3.5 hr at an initial pressure of 15 psi. The solution is then filtered through magnesium silicate and the acetic acid is removed in vacuo. The residue is partitioned between water and ethyl acetate. The water is separated and combined with 2, 100 ml 1N HCl washes of the ethyl acetate. The aqueous washes are made alkaline with 1N HCl (pH=10) and extracted with ethyl acetate (2×100 ml). The combined organic extracts are then washed with 100 ml of brine and are dried over MgSO$_4$. After filtering, removal of the solvent in vacuo leaves 1.323 g (40% yield) of the title compound: $^{13}$C—NMR (d$_4$-methanol) 158.9, 158.4, 138.1, 129.5, 129.0, 128.7, 94.8, 93.7, 74.7, 73.9, 73.3, 68.7, 68.3, 67.7, 66.8, 65.7, 61.2, 57.9, 45.8, 39.7, 31.8 and 21.2 ppm.

EXAMPLE 51

N,N'-dibenzyloxycarbonyl-3'-(R)-spectinomycin cyanohydrin (Formula LXVIII: R$_1$ and R$_3$ are as in Example 48)

Refer to Chart F.

In 1 ml of methanol are combined 1.0 g (1.66 mmol) of N,N'-dibenzyloxycarbonylspectinomycin and 0.152 ml (1.66 mmol) of acetone cyanohydrin. To this solution is added 0.5 g of Amberlite IR-45 C.P. resin, followed by 1 ml of saturated aqueous NH$_4$Cl. The reaction is stirred for 24 hr at room temperature. The reaction is then filtered and the methanol removed in vacuo. the residue is partitioned between ethyl acetate and water. The ethyl acetate is separated and combined with the, ethyl acetate extract of the aqueous phase. The combined extracts are washed with brine and dried over MgSO$_4$. After filtering, the solvent is removed in vacuo to afford 1.229 g of a white solid. The material is taken up in CHCl$_3$ and chromatographed on 35 g of silica, slurry packed in CHCl$_3$. The column is eluted as follows: 200 ml 1% methanol/CHCl$_3$; 1 L 2% methanol/CHCl$_3$ and 1 L 4% methanol/CHCl$_3$. Elution volume 600–850 ml contains 364 mg of N,N'-dibenzyloxycarbonylspectinomycin. Elution volume 1100–1200 ml contains 131 mg of the title compound while 207 mg of N,N'-dibenzyloxycarbonyl-3'-(S)-spectinomycin cyanohydrin is found in elution volume 1450 ml–2100 ml. The yield of the desired cyanohydrin is 20%: $^{13}$C—NMR (d$_6$-Acetone) 156.9, 137.8, 129.0, 128.3, 120.1, 95.2, 91.5, 73.3, 74.8, 74.5, 74.1, 73.9, 67.8, 67.3, 66.2, 60.7, 60.6, 60.4, 57.6, 57.5, 57.3, 42.0, 31.7 and 20.6 ppm.

EXAMPLE 52

N,N'-dibenzyloxycarbonyl-3'-(R)-3'-(aminomethyl)-dihydrospectinomycin (Formula LXIV: R$_1$ and R$_3$ are as in Example 48)

Refer to Chart F.

In 1 ml of acetic acid is dissolved 130 mg (0.21 mmol) of N,N'-dibenzyloxycarbonyl-3'-(R)-spectinomycin cyanohydrin (Example 51). This solution is added to a Paar bottle containing 0.5 gm of wet Raney-Nickel. The solution is hydrogenated at 15 psi for 2 hr. The solution is filtered through magnesium silicate and rinsed with methanol. The filtrate is concentrated in vacuo and the residue partitioned between diethyl ether and water. The aqueous phase is separated and made alkaline with the addition of concentrated NH$_4$OH (pH-9). The basic solution is extracted with ethyl acetate (2×20 ml). The combined extracts are washed with 20 ml of brine and dried over MgSO$_4$. After filtering, removal of the solvent leaves 73 mg of the title compound (56.6% yield).

EXAMPLE 53

N,N'-dibenzyloxycarbonyl-3'-(R)-3'-(aminomethyl)-dihydrospectinomycin (Formula LXIV: R$_1$ and R$_3$ are as in Example 48)

In 25 ml of methanol is dissolved 10.0 g (16.6 mmol) N,N'-dicarbobenzyloxy-spectinomycin and 7.6 ml (83.2 mmol) of acetone cyanohydrin. To this solution is added 5.0 g of IR-45 C.P. resin. The mixture is stirred for 3.5 hr, filtered and concentrated in vacuo. Thr residue is taken up in ethyl acetate and washed with water (2×50 ml). The combined washes are backwashed with ethyl acetate (1×20 ml). The combined organics are washed with 50 ml of brine and dried over MgSo$_4$. After filtering, removal of the solvent in vacuo affords 11.34 g of a white solid. By TLC the products consist of unreacted material and both formula LXVII and LXVIII cyanohydrin epimers. The mixture is dissolved in 50 ml of acetic acid and the solution is added to a Paar bottle containing 17 g of wet Raney-Nickel. The solution is hydrogenated at 15 psi for 1 hr, and filtered through Magensol. The filtrate is concentrated in vacuo and the residue partitioned between diethyl ether and water. Enough ethyl acetate is added to solubilize everything. The aqueous phase is separated and made alkaline with concentrated NH$_4$OH. The basic solution is extracted with methyl acetate. An emulsion forms which is broken up by filtering through diatomaceous earth. The ethyl acetate is separated and combined with a 100 ml ethyl acetate extract of the aqueous phase. The combined extracts are washed with brine, dried over MgSO$_4$ and filtered. Removal of the solvent affords 3.49 g of a blue solid. The product is taken up in CHCl$_3$ and chromatographed on 100 g of silica, slurry packed in CHCl$_3$. The column is eluted as follows, with 1% aqueous NH$_4$OH added to the mobile phase: 200 ml 1% methanol/CHCl$_3$; 200 ml 2% methanol/CHCl$_3$; 200 ml 3% methanol/CHCl$_3$; 200 ml 4% methanol/CHCl$_3$; 3 L 5% methanol/CHCl$_3$; 1 L 10% methanol/CHCl$_3$. In elution volume 2.5 l to 4.2 l there is obtained 1.173 g of the title compound as a white solid (11.2% yield, based on starting material: $^{13}$C—NMR (d$_4$-methanol) 158.23, 138.0, 129.4, 128.8, 128.6, 96.3, 94.3, 74.6, 73.8, 68.1, 66.7, 65.5, 60.9, 60.8, 58.0, 45.6, 41.4, 31.8 and 21.5 ppm.

EXAMPLE 54

N,N'-dibenzyloxycarbonyl-3'-(R)-3'-(n-hexylaminomethyl)-dihydrospectinomycin (Formula LXVI: R$_{63}$ is hydrogen and R$_{64}$ is n-hexyl, R$_1$ and R$_3$ are as in Example 48) and N,N'-dicarbobenzyloxy-3'-(N,N-dihexylaminomethyl)-dihydrospectinomycin (Formula LXVI: R$_{63}$ and R$_{64}$ are both n-hexyl).

In 10 ml of methanol are combined 500 mg (0.79 mmol) of N,N'-dibenzyloxycarbonyl-3'-(R)-3'-(aminomethyl)-dihydrospectinomycin, 0.95 ml (7.9 mmol) of n-hexanal and 16.5 mg (0.26 mmol) of NaCNBH$_3$. A trace of methyl orange indicator is added and the pH is adjusted to the indicator's end point using 1N HCl/methanol. The reaction is stirred for 2 hr at room temperature, during which time an additional 33 mg (0.52 mmol) of NaCNBH$_3$ is added. The solvent is then removed in vacuo and the residue partitioned between water and ethyl acetate. The ethyl acetate is separated and combined with a 20 ml ethyl acetate extract of the aqueous phase. The combined extracts are washed with 50 ml of brine and dried over MgSO$_4$. After filtering, removal of the solvent affords an oil which is immediately taken up in CHCl$_3$ and chromatographed on 35 g of silica, slurry packed in CHCl$_3$. The column is eluted as follows: 100 ml CHCl$_3$; 200 ml 1% methanol/CHCl$_3$; 200 ml 2% methanol/CHCl$_3$; 200 ml 3% methanol/CHCl$_3$; and 1 liter of 5% methanol/CHCl$_3$. In elution volume 400–900 ml there is obtained 310 mg (49% yield) of N,N'-dibenzyloxycarbonyl-3'-(R)-3'-(N,N-dihexylaminomethyl)-dihydrospectinomycin as a white solid: $^{13}$C—NMR (d$_6$-Acetone) 138.2, 129.1, 128.7, 128.4, 128.2, 97.2, 93.8, 74.7, 74.4, 72.2, 67.2, 66.5, 65.4, 65.2, 61.0, 60.4, 60.3, 59.7, 57.7, 57.5, 55.9, 44.6, 32.4, 32.2, 32.0, 31.8, 31.5, 27.6, 26.9, 23.2, 21.5 and 14.3 ppm.

Exact mass calc'd for C$_{54}$H$_{94}$N$_3$O$_{11}$Si$_4$ (tetra TMS—CH$_3$): 1072.5965; Found: 1072.5968.

Elution volume 950–1400 ml contains 109 mg (19.3%) of N,N'-dibenzyloxycarbonyl-3'-(R)-3'-(N-hexylaminomethyl)-dihydrospectinomycin as a white solid: $^{13}$C—NMR (d$_6$-Acetone) 138.1, 129.1, 128.3, 128.1, 97.0, 93.8, 74.5, 71.7, 67.2, 66.4, 65.2, 57.6, 54.3, 49.7, 44.4, 32.2, 31.6, 29.9, 27.4, 23.1, 21.5, and 14.2 ppm.

Exact mass calc'd for C$_{49}$H$_{85}$N$_3$O$_{11}$Si$_4$ (tetra TMS): 1003.5261; Found: 1003.5278.

EXAMPLE 55

N,N'-dibenzyloxycarbonyl-3'-(R)-3'-(N-isobutylaminomethyl)-dihydrospectinomycin and 3'-(N,N-diisobutylaminomethyl9-dihydrospectinomycin (Formula LXVI: $R_{63}$ is hydrogen or isobutyl, respectively, $R_{64}$ is isobutyl, and $R_1$ and $R_3$ are as in Example 48)

Refer to Chart F.

To a soluion of 500 mg (0.79 mmol) of N,N'-dibenzyloxycarbonyl-3'-(R)-3'-(aminomethyl)-dihydrospectinomycin in 10 ml of methyl alcohol is added 0.72 ml (7.9 mmol) of isobutyraldehyde and a trace of methyl orange indicator. The pH is adjusted to the indicator's end point with methanolic HCl and 16.5 mg (0.26 mmol) of sodium cyanoborohydride in 1 ml of methyl alcohol is added. The reaction is stirred at room temperature and the pH is maintained near the endpoint of methyl orange by adding additional methanolic HCl. The reaction is easily followed by TLC using Analtech Silica plates and eluting with 10% $MeOH/CHCl_3/1\%$ $NH_4OH$ as a solvent. When the reaction is complete, the solvent is removed in vacuo and the residue is partitioned between $H_2O$ and EtOAc. The aqueous phase is made alkaline with the addition of concentrated $NH_4OH$ and the EtOAc is separated and combined with an additional EtOAc extract. The combined extracts are washed with brine and dried over $MgSO_4$. The solvent is then removed in vacuo to afford the crude product. The product is taken up in $CHCl_3$ and chromatographed on silica, slurry packed in $CHCl_3$. The column is eluted with a $MeOH/CHCl_3$ gradient (1%–5%), and 50 ml fractions are taken. The fractions are analyzed by TLC and pure fractions are pooled and concentrated in vacuo to afford 216 mg (39.8%) of N,N'-dibenzyloxycarbonyl-3'-(R)-3'-(N-isobutylaminomethyl)dihydrospectinomycin: $^{13}$C NMR ($d_6$-acetone): 138.1, 129.1, 128.6, 128.3, 128.1, 97.1, 93.8, 74.5, 71.7, 67.2, 66.4, 65.2, 57.8, 54.6, 44.4, 31.8, 31.6, 28.4, 21.5, 20.9, and 20.8 ppm. Exact mass calc'd for $C_{47}H_{81}N_3O_{11}Si_4$ (tetra TMS) 975.4948, found 975.4943.

The same procedure, using 631 mg (1.0 mmol) of the amine, 1.82 ml (20 mmol) of aldehyde and 188 mg (3.0 mmol) of sodium cyanoborohydride afforded 171 mg (23%) of N,N'-dibenzyloxycarbonyl-3'-(R)-3'-(N,N-diisobutylaminomethyl)-dihydrospectinomycin: $^{13}$C NMR ($d_6$-acetone) 138.1, 129.1, 128.3, 128.1, 97.0, 93.5, 74.6, 73.1, 67.3, 67.2, 66.4, 65.2, 61.1, 57.5, 44.1, 31.4, 26.8, 21.7 and 21.4 ppm; exact mass calc'd for $C_{48}H_{81}N_3O_{11}Si_4$ (tri—TMS) 959.5179, found, 959.5134.

EXAMPLE 56

N,N'-dibenzyloxycarbonyl-3'-(R)-3'-(N-cyclohexylmethylaminomethyl)-dihydrospectinomycin and N,N'-dibenzyloxycarbonyl-3'-(R)-3'-[N,N-di(cyclohexylmethyl)aminomethyl]-dihydrospectinomycin (Formula LXVI: $R_{63}$ is hydrogen or cyclohexylmethyl, respectively, $R_{64}$ is cyclohexylmethyl, and $R_1$ and $R_3$ are as in Example 48.)

Alkylation of 2.4 g (3.9 mmol) of N,N'-dibenzyloxycarbonyl-3'-(R)-3'-(aminomethyl)dihydrospectinomycin using 2.11 ml (19.5 mmol) of cyclohexane carboxaldehyde and 180 mg (2.8 mmol) of sodium cyanoborohydride following the procedure in example 55 afforded 982 mg (31%) of N,N'-dibenzyloxycarbonyl-3'-(R)-3'-[(N-cyclohexylmethyl)-aminomethyl]dihydrospectinomycin: $^{13}$C—NMR ($d_6$-Acetone) 138.1, 129.1, 128.3, 97.0, 93.7, 74.5, 71.7, 67.2, 66.5, 65.2, 57.6, 56.5, 54.6, 44.5, 38.0, 31.9, 31.6, 27.2, 26.5, and 21.5 ppm; exact mass calc'd for $C_{50}H_{85}N_3O_{11}Si_4$ (tetra TMS) 1015.5261, found 1015.5240.

Alkylation of 634 mg (1.0 mmol) of the amine using 1.08 ml (10 mmol) of aldehyde and 62.8 mg (1.0 mmol) of sodium cyanoborohydride gave 173 mg (21%) of N,N'-dibenzyloxycarbonyl-3'-(R)-3'-[N,N-di(cyclohexylmethyl)-aminomethyl]-dihydrospectinomycin: $^{13}$C—NMR ($d_6$-Acetone) 129.1, 128.4, 128.2, 97.3, 93.5, 74.7, 72.9, 67.4, 67.2, 66.5, 65.1, 61.2, 57.7, 57.6, 57.4, 44.6, 36.5, 32.6, 32.4, 31.7, 27.2, 26.7 and 21.4 ppm; exact mass calc'd for $C_{53}H_{86}N_3O_{11}Si_3$ (tri TMS—$CH_3$) 1024.5570, found 1024.5526.

EXAMPLE 57

Deprotection of the N,N'-dibenzyloxycarbonyl-3'-(R)-3'-mono and di-alkylaminomethyl-dihydrospectinomycin of Examples 54–56

The protected products of Example 54, 55, or 56 is dissolved in methanol and an equivalent weight of Pd black is added. To this mixture is added 20 equivalents of formic acid. The reaction is stirred for 45 min, filtered and concentrated to dryness. The residue is taken up in water and 3.5 equivalents of 1N HCl are added. The solution is frozen and lyophilized to afford the following final products:

(a) 3'-(R)-3'-(N-hexylaminomethyl)-dihydrospectinomycin trihydrochloride:

Deprotection of 87 mg (0.12 mmol) affords 58 mg (87% yield) of the title compound as a white solid: $^{13}$C—NMR ($D_2O$) 94.1, 93.3, 73.2, 70.5, 68.3, 66.9, 66.2, 62.5, 60.6, 59.3, 51.0, 49.8, 40.9, 31.9, 31.5, 31.4, 26.3, 25.8, 22.7, 21.0 and 14.3 ppm.

Exact mass calc'd for $C_{39}H_{89}N_3O_7Si_6$ (hexa—TMS): 879.5316; Found: 879.5303.

(b) 3'-(R)-3'-(N-isobutylaminomethyl)-dihydrospectinomycin trihydrochloride:

Deprotection of 216 mg (0.29 mmol) affords 152 mg (90% yield) of the title compound as a white solid: $^{13}$C—NMR ($D_2O$) 93.9, 93.3, 73.0, 70.3, 68.1, 66.8, 66.1, 62.3, 60.5, 59.2, 56.3, 51.3, 41.2, 31.8, 31.4, 25.5, 21.0, 19.9, and 19.7 ppm exact mass calc'd for $C_{37}H_{85}N_3O_7Si_6$ (hexa TMS) 851.5003, found 851.5020.

(c) 3'-(R)-3'-(N-cyclohexylmethylaminomethyl9-dihydrospectinomycin trichloride:

Deprotection of 928 mg (1.12 mmol) afford 640 mg of the title compound as a white solid (86% yield): $^{13}$C—NMR ($D_2O$) 94.2, 93.5, 73.2, 70.6, 68.3, 66.9, 66.3, 62.5, 60.6, 59.4, 55.3, 51.5, 41.3, 34.6, 31.9, 31.5, 30.7, 26.5, 25.9, and 21.0 ppm; exact mass calc'd for $C_{40}H_{89}N_3O_7Si_6$ (hexa TMS) 891.5316, found 891.5324.

(d) 3'-(R)-3'-(N,N-dihexylaminomethyl)-dihydrospectinomycin trihydrochloride:

Deprotection of 220 mg (0.28 mmol) affords 157 mg (88% yield) of the title compound as a white solid: $^{13}$C—NMR ($D_2O$) 94.1, 93.3, 70.5, 68.3, 68.1, 66.7, 66.6, 66.5, 66.3, 62.4, 60.5, 59.3, 56.9, 56.7, 31.9, 31.5, 26.3, 23.7, 22.8, 21.0 and 14.4 ppm. Exact mass calc'd for $C_{42}H_{93}N_3O_7Si_6$ (hexa TMS): 891.5860; found: 891.5853.

(e) 3'-(R)-3'-(N,N-diisobutylaminomethyl)-dihydrospectinomycin trihydrochloride:

Deprotection of 153 mg (0.20 mmol) affords 96 mg of the title compound (82% yield): $^{13}$C—NMR ($D_2O$) 94.3, 93.9, 73.3, 70.6, 68.2, 66.7, 66.6, 65.7, 62.6, 60.7, 59.6, 43.3, 31.9, 31.8, 31.6, 25.1, 24.8, 21.1, 21.0, 20.6, 20.4, 19.8 and 19.6 ppm; exact mass calc'd for $C_{38}H_{85}N_3O_7Si_5$ (penta—TMS) 835.5234, found 835.5241.

(f) 3'-(R)-3'-(N,N-di[cyclohexylmethyl]aminomethyl)dihydrospectinomycin trihydrochloride:

Deprotection of 149 mg (0.18 mmol) affords 124 mg of the title compound as a white solid (100% yield): $^{13}C$—NMR ($D_2O$) 94.3, 93.8, 73.2, 70.5, 68.2, 66.9, 66.5, 65.2, 64.5, 62.6, 60.7, 59.5, 43.2, 34.1, 33.7, 31.9, 31.8, 31.3, 30.9, 30.7, 26.5, 25.9, and 21.1 ppm; exact mass calc'd for $C_{41}H_{85}N_3O_7Si_4$ (tetra TMS) 843.5465, found 843.5459.

EXAMPLE 58

N,N'-dibenzyloxycarbonyl-3'-(R)-3'-(cycloalkylaminomethyl)dihydrospectinomycins (Formula XLVI: At least one of $R_{63}$ and $R_{64}$ is cycloalkyl.)

Refer to Chart F.

In 3 ml of methanol are combined 1 mmol of N,N'-dibenzyloxycarbonyl-3'-(R)-3'-(aminomethyl)dihydrospectinomycin, Example 52, and 10 mmol of the cycloalkanone. To this solution is added 0.33 mmol of sodium cyanoborohydride. The pH is adjusted to 6 with methanolic hydrogen chloride. The reaction is followed by TLC on silica eluting with 90:10:1 chloroform/methanol/concentrated aqueous ammonia. When the reaction is complete, the solvent is removed in vacuo and the residue partitioned between ethyl acetate and water, made alkaline with concentrated aqueous ammonia. The ethyl acetate is separated, combined with a second extract, washed with brine and dried over magnesium sulfate. After filtering, the solvent is removed in vacuo and the residue chromatographed on 40 g of silica, slurry packed in chloroform. The column is eluted with a methanol chloroform gradient and 45 ml fractions are collected. The desired product is found by TLC analysis. The pure fractions are pooled and concentrated to afford the following final products:

(a) N,N'-dibenzyloxycarbonyl-3'-(R)-3'-(cyclopentylaminomethyl)dihydrospectinomycin (Formula LXVI: $R_{63}$ is cyclopentyl and $R_{64}$ is hydrogen.)

The title compound is obtained in a 47% yield, 328 mg of a white solid were obtained: $^{13}C$—NMR ($d_6$-acetone) 157.0, 138.2, 129.1, 128.3, 128.1, 97.2, 93.8, 74.6, 71.7, 67.1, 66.0, 65.2, 60.9, 60.2, 59.6, 57.7, 57.6, 57.5, 53.0, 44.6, 33.3, 32.5, 31.6, 24.4, 24.3, and 21.5 ppm; exact mass calc'd for $C_{48}H_{81}N_3O_{11}Si_4$ (tetra TMS) 987.4948. Found 987.4924.

(b) N,N'-dibenzyloxycarbonyl-3'-(R)-3'-(cyclohexylaminomethyl)dihydrospectinomycin (Formula LXVI: $R_{63}$ is cyclohexyl and $R_{64}$ is hydrogen.)

Chromatography affords 240 mg (34% yield) of the title compound as a white solid: $^{13}C$—NMR ($d_6$-acetone) 157.0, 138.2, 129.1, 128.3, 128.1, 97.2, 93.8, 74.6, 71.6, 67.1, 67.0, 66.4, 65.2, 60.9, 60.2, 57.6, 57.5, 56.6, 51.4, 44.5, 33.4, 33.3, 31.6, 26.6, 25.4, and 21.5 ppm; exact mass calc'd for $C_{49}H_{83}N_3O_{11}Si_4$ (tetra TMS): 1001.5104. Found: 1001.5132.

(c) N,N'-dibenzyloxycarbonyl-3'-(R)-3'-(cycloheptylaminomethyl)dihydrospectinomycin (Formula LXVI: $R_{63}$ is cycloheptyl and $R_{64}$ is hydrogen.)

Chromatography affords 178 mg (24.5%) of the title compound as a white solid: $^{13}C$—NMR ($d_6$-acetone) 157.0, 138.0, 129.0, 128.2, 128.0, 97.0, 93.6, 74.5, 71.5, 67.1, 66.4, 65.2, 60.6, 60.0, 58.7, 57.5, 51.7, 44.5, 34.7, 34.6, 31.6, 28.8, 24.5, and 21.4 ppm; exact mass calc'd for $C_{50}H_{85}N_3O_{11}Si_4$: 1015.5261. Found: 1015.5282.

EXAMPLE 59

Preparation of 3'-(R)-3'-(cycloalkylaminomethyl)dihydrospectinomycin trihydrochlorides Refer to Chart F.

The N,N'-dibenzyloxycarbonyl-3'-(R)-3'-(cycloalkylablack are combined in 10 ml of methanol. To the mixture is added 10 equivalents of formic acid. After stirring for 20 min, the reaction mixture is filtered and the solvent is removed in vacuo. The solid residue is taken up in water and treated with 3.5 equivalents of 1N hydrochloric acid. The solution is frozen and lyophilized to afford the following final products:

(a) 3'-(R)-3'-(cyclopentylaminomethyl)dihydrospectinomycin trihydrochloride

Deprotection of 320 mg (0.45 mmol) affords 244 mg (100%) of the title compound as a white solid: $^{13}C$—NMR ($D_2O$) 94.2, 93.3, 73.4, 70.6, 68.4, 67.0, 66.3, 62.6, 61.8, 60.7, 59.4, 50.4, 40.7, 31.9, 31.5, 30.1, 24.7, and 21.0 ppm; exact mass calc'd for $C_{39}H_{87}N_3O_7Si_6$ (hexa—TMS): 877.5159. Found: 877.5143.

(b) 3'-(R)-3'-(cyclohexylaminomethyl)dihydrospectinomycin trihydrochloride

Deprotection of 240 mg (0.33 mmol) affords 154 mg (84.1% yield) of the title compound as a white solid: $^{13}C$—NMR ($D_2O$) 94.1, 93.3, 73.3, 70.6, 68.3, 66.9, 66.3, 62.5, 60.6, 59.8, 59.4, 48.1, 40.8, 31.9, 31.5, 29.5, 29.3, 25.4, 25.0, and 21.0 ppm. Exact mass calc'd for $C_{39}H_{87}N_3O_7Si_6$ (hexa TMS): 877.5159. Found 877.5143.

(c) 3'-(R)-3'-(cycloheptylaminomethyl)dihydrospectinomycin trihydrochloride

Deprotection of 160 mg (0.22 mmol) affords 120 mg (96%) of the title compound as a white solid: $^{13}C$—NMR ($D_2O$) 94.1, 93.3, 73.3, 70.5, 68.3, 66.9, 66.3, 62.5, 61.7, 60.6, 59.3, 48.1, 40.9, 31.9, 31.5, 31.1, 27.9, 24.6, and 21.0 ppm; exact mass calc'd for $C_{40}H_{89}N_3O_7Si_6$ (hexa TMS): 891.5316. Found: 891.5350.

EXAMPLE 60

N,N'-dibenzyloxycarbonyl-3'-(R)-3'-[(2-hydroxyethyl)aminomethyl]dihydrospectinomycin (Formula LXVI: $R_{63}$ is hydrogen and $R_{64}$ is 2-hydroxyethyl.)

Refer to Chart F.

In 5 ml of methanol are combined 1.0 g (1.6 mmol) of N,N'-dibenzyloxycarbonyl-3'-(R)-3'-(aminomethyl)-dihydrospectinomycin (Example 52) and 528 mg (8.8 mmol) of glycolaldehyde. The pH is adjusted to 4 with 1N methanolic hydrogen chloride and 33 mg of sodium cyanoborohydride in 1 ml of methanol is added. The reaction is stirred for 30 min and the solvent is removed in vacuo. The residue is partitioned between ethyl acetate and water, made alkaline with concentrated aqueous ammonia. The ethyl acetate is separated and combined with an additional ethyl acetate extract. The extracts are then washed with brine and dried over magnesium sulfate. After filtering, the solvent is removed in vacuo to afford 966 mg of a white solid. The product is taken up in chloroform and chromatographed on 35 g of silica, slurry packed in chloroform. The column is then eluted with 1% methanol chloroform (200 ml), 2% (200 ml), 5% (200 ml) and 10% (1 l). Elution volume 900-1050 ml contains 311 mg of the title compound (39% yield): $^{13}C$—NMR ($d_6$-acetone) 157.7, 138.2, 129.1, 128.4, 128.2, 97.0, 93.9, 74.6, 71.8, 67.2, 66.4, 65.2, 61.2, 60.9, 60.3, 57.7, 57.6, 54.2, 51.8, 44.4, 31.7, and 21.5

(Example 61) and 320 mg of palladium black. To this solution is added 390 μl (10.0 mmol) of formic acid. The mixture is stirred for 30 min, filtered and concentrated in vacuo to afford 584 mg of a white solid. The product is taken up in water and treated with 4 ml of 1N hydrochloric acid. The solution is frozen and lyophilized to afford 539 mg (96.8%) of the title compound as a white solid: $^{13}$C—NMR (D$_2$O) 93.9, 93.3, 73.1, 70.3, 68.2, 66.7, 66.1, 62.3, 62.1, 604, 59.2, 50.9, 49.5, 40.7, 31.8, 31.5, 25.5, 23.0 and 20.9; Exact mass calcd for C$_{41}$H$_{95}$N$_3$O$_8$Si$_7$ (hepta TMS): 953.5504. Found: 953.5555.

EXAMPLE 66

3′-(R)-3′-[(6-chlorohexyl)aminomethyl]dihydrospectinomycin trihydrochloride

Refer to Chart F.

In 5 ml of methanol is dissolved 138 mg (0.18 mmol) of N,N′-dibenzyloxycarbonyl-3′-(R)-3′-[(6-chlorohexyl)aminomethyl]dihydrospectinomycin (Example 62). To this solution is added 116 mg of palladium black followed by 70 μl (1.8 mmol) of formic acid. The reaction is stirred for 5 min and is filtered. Removal of the solvent in vacuo affords a white solid which is taken up in water and treated with 1 ml of 1N hydrochloric acid. The solution is frozen and lyophilized to afford 94 mg (88.3% yield) of the title compound as a white solid: $^{13}$C—NMR (D$_2$O) 94.2, 93.4, 73.4, 70.7, 68.4, 67.0, 66.4, 62.6, 60.7, 59.5, 51.1, 49.7, 46.7, 41.0, 32.6, 31.9, 31.6, 26.6, 26.0, 25.8 and 21.0 ppm; Exact mass calcd for C$_{39}$H$_{72}$N$_3$O$_7$Si$_6$ (hexa TMS): 913.4926. Found: 913.4930.

EXAMPLE 67

3′-(R)-3′-[(carbomethoxymethyl)aminomethyl]dihydrospectinomycin trihydrochloride Refer to Chart F.

In 5 ml of methanol is dissolved 200 mg (0.28 mmol) of N,N′-dibenzyloxycarbonyl-3′-(R)-3′-[(carbomethoxymethyl)aminomethyl]dihydrospectinomycin (Example 63). To this solution is added 200 mg of palladium black and 0.122 ml (3.12 mmol) of formic acid. The reaction is stirred for 20 min, filtered, and concentrated in vacuo to afford 127 mg of a white solid. The product is taken up in water and treated with 1 ml of 1N hydrochloric acid. The solution is frozen and lyophilized to afford 133 mg (87% yield) of the title compound as a white solid: $^{13}$C—NMR (D$_2$O) 168.4, 94.0, 93.3, 73.1, 70.4, 68.2, 66.8, 66.2, 62.4, 60.51, 59.3, 54.5, 51.8, 48.9, 41.1, 31.8, 31.5, and 21.0 ppm; Exact mass calcd for C$_{30}$H$_{65}$N$_3$O$_9$Si$_4$ (tetra TMS): 723.3798. Found: 723.3823.

EXAMPLE 68

N,N′-dibenzyloxycarbonyl-3′-(R)-3′-[(benzyloxycarbonylmethyl)aminomethyl]dihydrospectinomycin (Formula LXVI: R$_{63}$ is hydrogen and R$_{64}$ is benzyloxycarbonyl methyl)

Refer to Chart F.

In 10 ml of ethylene dichloride are combined 631 mg (1 mmol) of N,N′-dibenzyloxycarbonyl-3′-(R)-3′-(aminomethyl)dihydrospectinomycin, and 164 mg (1 mmol) of benzylglyoxylate. The solution is refluxed for 3 hr and the solvent is removed in vacuo. The yellow solid obtained is taken up methanol and treated with 105 mg of sodium cyanoborohydride (1.67 mmol), added portionwise over a period of 2 hr. The pH is maintained at 4 by adding 2N methanolic hydrogen chloride. The solvent is removed in vacuo and the residue partitioned between ethyl acetate and water, made alkaline with concentrated aqueous ammonia. The ethyl acetate is separated and combined with a second ethyl acetate extract. The extracts are washed with brine and dried over magnesium sulfate. After filtering, the solvent is removed in vacuo to afford 771 mg of a white solid. The product is taken up in chloroform and chromatographed on 37 g of silica, slurry packed in chloroform. The column is eluted with 1% methanol/chloroform (500 ml), 2% (1 l) and 3% (1 l), and 45 ml fractions are taken. Based on TLC analysis of each fraction, fractions 8–21 are pooled and concentrated to afford 396 mg (50.8% yield) of the title compound as a white solid: $^{13}$C—NMR (d$_6$-acetone) 172.0, 157.2, 156.5, 138.1, 136.4, 129.1, 128.8, 128.3, 128.1, 96.6, 93.7, 74.5, 72.1, 67.1, 66.7, 66.5, 65.2, 60.0, 57.5, 53.7, 50.5, 44.0, 31.6, and 21.5 ppm. Exact mass calc'd for C$_{51}$H$_{78}$N$_3$O$_{13}$Si$_4$ (tetra TMS): 1052.4611. Found: 1052.4601.

EXAMPLE 69

3′-(R)-3′-[(carboxymethyl)aminomethyl]dihydrospectinomycin trihydrochloride

Refer to Chart F.

In 10 ml of methanol is dissolved 390 mg (0.5 mmol) of N,N′-dibenzyloxycarbonyl-3′-(R)-3′-[(benzyloxycarbonylmethyl)aminomethyl]dihydrospectinomycin (Example 68). To this solution is added 390 mg of palladium black followed by 0.2 ml (5.0 mmol) of formic acid. The reaction is stirred for 20 min and an additional 0.1 ml (2.5 mmol) of formic acid is added. After stirring for 1.5 hr, the reaction is filtered thru celite and concentrated in vacuo to afford 328 mg of a white solid. The product is taken up in water and treated with 2 ml of 1N hydrochloric acid. The solution is frozen and lyophilized to afford 237 mg (84.5% yield) of a white solid: $^{13}$C—NMR (D$_2$O) 170.9, 94.2, 93.5, 73.2, 70.6, 68.3, 67.0, 66.3, 62.6, 60.7, 59.4, 52.0, 50.8, 41.5, 31.9, 31.5, and 21.1 ppm; exact mass calc'd for C$_{32}$H$_{71}$N$_3$O$_9$Si$_5$ (penta TMS) 781.4036. Found: 781.4063.

EXAMPLE 70

N,N′-dibenzyloxycarbonyl-3′-(R)-3′-(N-acetylaminomethyl) dihydrospectinomycin (Formula LXXXVIII: R$_{45}$ is methyl)

Refer to Chart F.

To a solution of 631 mg (1.0 mmol) of N,N′-dibenzyloxycarbonyl-3′-(R)-3′-aminomethyldihydrospectinomycin in 4 ml of methanol stirred at 0° under a nitrogen atmosphere is added 0.15 ml (1.1 mmol) of triethylamine and 0.10 ml (1.1 mmol) of acetic anhydride. The mixture is stirred 1.15 hr at 0°, and then concentrated in vacuo. The residue is dissolved in 35 ml of ethyl acetate and washed twice with 5 ml of water, once with 20 ml of brine and dried over MgSO$_4$. Removal of solvent in vacuo affords 600 mg of white solid. The product is purified by chromatography on 40 g of 230–400 mesh silica gel packed with 1% methanol/chloroform and eluted with 1 l of 1% methanol/chloroform, 2 l of 2% methanol/chloroform and finally 3% methanol/chloroform, taking 45 ml fractions. Fractions 71–98 are pooled and concentrated to give 212 mg (0.32 mmol, 32%) of title product as a white solid: $^{13}$C—NMR (d$_6$-acetone) δ 171.7, 157.0, 138.2, 129.1, 128.4, 95.0, 93.3, 75.8, 74.5, 67.7, 67.4, 70.0, 66.6, 60.0, 57.0, 42.2, 39.6, 31.8, 22.9, and 21.5; MS exact mass for ppm; exact mass calc'd for $C_{48}H_{85}N_3O_{12}Si_5$: 1035.4979. Found: 1035.4965.

EXAMPLE 61

N,N'-dibenzyloxycarbonyl-3'-(R)-3'-[(5-hydroxylpentyl)aminomethyl]dihydrospectinomycin (Formula LXVI: $R_{63}$ is hydrogen and $R_{64}$ is 5-hydroxypentyl.)

Refer to Chart F.

In 95 ml of methanol are combined 5.0 g (7.9 mmol) of N,N'-dibenzyloxycarbonyl-3'-(R)-3'-(aminomethyl)-dihydrospectinomycin (Example 52) and 7.6 ml (8.02 g, 79 mmol) of 5-hydroxypentanal. The pH is adjusted to 4.5–5.0 with 2N HCl in methanol and 51.1 mg (0.813 mmol) of sodium cyanoborohydride is added. The reaction is allowed to stir for 40 min and the solvent is removed in vacuo. The residue is partitioned between water and ethyl acetate. The aqueous phase is made alkaline with concentrated aqueous ammonia and the ethyl acetate is separated. The extract is combined with an additional ethyl acetate extract of the aqueous phase. The extracts are then washed with brine and dried over magnesium sulfate. After filtering, the solvent is removed in vacuo to afford 9.31 g of a liquid. The product is taken up in chloroform and chromatographed on 300 g of silica, which is slurry packed in chloroform. The column is eluted with 1% methanol chloroform (1 l), 2% (1 l), 3% (2 l), 4% (2 l), 5% (2 l), 5% with 0.5% added concentrated aqueous ammonia (4 l) and 10% with 1% added concentrated ammonia (2 l). The desired product is found by TLC analysis of each 50 ml fraction. The pure fractions are combined and the solvent removed to afford 1.82 g (32% yield) of the title compound as a white solid: $^{13}$C—NMR ($d_6$-acetone) 138.2, 129.1, 128.4, 128.2, 97.1, 93.6, 74.6, 71.7, 67.2, 66.5, 65.3, 62.3, 57.3, 57.6, 54.4, 49.7, 44.5, 33.3, 31.7, 29.8, 24.2 and 21.6 ppm; exact mass calc'd for $C_{51}H_{91}N_3O_{12}Si_5$ (penta TMS): 1077.5449. Found: 1077.5492.

EXAMPLE 62

N,N'-dibenzyloxycarbonyl-3'-(R)-3'-[(6-chlorohexyl)aminomethyl]dihydrospectinomycin (Formula LXVI: $R_{63}$ is hydrogen and $R_{64}$ is 6-chlorohexyl)

Refer to Chart F.

In 20 ml of methanol are combined 1.0 g (1.58 mmol) of N,N'-dibenzyloxycarbonyl-3'-(R)-3'-(aminomethyl)-dihydrospectinomycin (Example 52) and 1.08 g (8.06 mmol) of 6-chlorohexanal. To this solution is added 33 mg (0.52 mmol) of sodium cyanoborohydride. The pH is adjusted to 4 with 2N methanolic hydrogen chloride and the reaction is allowed to stir for 30 min. The solvent is removed in vacuo and the residue partitioned between ethyl acetate and water, made alkaline with concentrated aqueous ammonia. The ethyl acetate was separated and combined with a second ethyl acetate extract. The combined extracts are washed with saturated aqueous sodium bisulfite and brine. After drying over magnesium sulfate, the solvent is removed in vacuo to afford 1.371 g of a white solid. The product is taken up in chloroform and chromatographed on 100 g of silica, slurry packed in chloroform. The column is eluted with 500 ml of chloroform, 1% methanol chloroform (1 l) 2% (1 l) and 5% (1 l). The desired product is found by TLC analysis of each 45 ml fraction. Fractions 50–60 are pooled and concentrated to afford 170 mg (14% yield) of the title compound as a white solid: $^{13}$C—NMR ($d_6$-acetone) 157.5, 156.6, 138.2, 129.1, 128.3, 128.1, 97.1, 93.8, 74.6, 71.7, 67.2, 66.4, 65.2, 61.0, 57.7, 57.6, 54.3, 49.6, 45.6, 44.5, 33.2, 31.6, 29.8, 27.2, 27.0, and 21.5 ppm: Exact mass calcd for $C_{48}H_{81}ClN_3O_{11}Si_4$ (tetra TMS minus methyl): 1022.4636. Found: 1022.4607.

EXAMPLE 63

N,N'-dicarbobenzyloxy-3'-(R)-3'-[carbomethoxymethyl)aminomethyl]dihydrospectinomycin (Formula LXVI: $R_{63}$ is hydrogen and $R_{64}$ is carbomethoxymethyl)

Refer to Chart F.

In 5 ml of methylene chloride are combined 1.13 g (1.8 mmol) of N,N'-dibenzyloxycarbonyl-3'-(R)-3-(aminomethyl)dihydrospectinomycin (Example 52) and 1.58 mg (1.8 mmol) of methyl glyoxylate. The resulting solution is refluxed for 5 hr and the solvent removed in vacuo. The solid residue is taken up in methanol and treated with 4.52 mg (7.2 mmol) of sodium cyanoborohydride. The pH is adjusted to 4 with 2N methanolic hydrogen chloride and the reaction is stirred for 30 min. The solvent is removed in vacuo and the residue partitioned between ethyl acetate and water, made alkaline with concentrated aqueous ammonia. The ethyl acetate is separated and combined with a second ethyl extract. The extracts are washed with brine and dried over magnesium sulfate. After filtering, the solvent is removed in vacuo to afford 1.12 g of a white solid. The product is taken up in chloroform and chromatographed on 40 g of silica, slurry packed in chloroform. The column is eluted with 1% methanol chloroform (500 ml), 2% (1 l) and 3% (1 l). Each 45 ml fraction is analyzed by TLC. Fractions 15–28 are pooled and concentrated to afford 697 mg (55.1%) of the title compound as a white solid: $^{13}$C—NMR ($d_6$-acetone) 172.5, 156.0, 138.1, 129.1, 128.3, 128.1, 96.6, 93.7, 74.4, 72.1, 67.1, 66.4, 65.2, 60.0, 57.6, 53.4, 51.9, 50.3, 31.6, and 21.5 ppm; Exact mass calcd for $C_{45}H_{77}N_3O_{13}Si_4$ (tetra TMS): 991.4534. Found: 991.4499.

EXAMPLE 64

3'-(R)-3'-[(2-hydroxyethyl)aminomethyl]dihydrospectinomycin trihydrochloride

Refer to Chart F.

In 5 ml of methanol is dissolved 300 mg (0.44 mmol) of N,N'-dibenzyloxcarbonyl-3'-(R)-3'-[(2-hydroxyethyl)aminomethyl]dihydrospectinomycin (Example 60). To this solution is added 300 mg of palladium black followed by 173 μl (4.4 mmol) of formic acid. The reaction is stirred for 20 min, filtered and concentrated in vacuo to afford 215 mg of a white solid. The product is taken up in water and treated with 1.5 ml of 1N hydrochloric acid. The solution is frozen and lyophilized to afford 200 mg of the title compound as a white solid (88.1% yield): $^{13}$C—NMR ($D_2O$) 94.1, 93.4, 73.1, 70.5, 68.3, 66.9, 66.3, 62.5, 60.6, 59.4, 57.0, 51.3, 50.8, 41.3, 31.9, 31.6, and 21.0 ppm; Exact mass calcd for $C_{38}H_{89}N_3O_8Si_7$ (hepta TMS): 911.5034. Found 911.4995.

EXAMPLE 65

3'-(R)-3'-[(5-hydroxypentyl)aminomethyl]dihydrospectinomycin trihydrochloride

Refer to Chart F.

In 10 ml of methanol are combined 720 mg (1.0 mmol) of N,N'-dibenzyloxycarbonyl-3'-(R)-3'-[(5-hydroxypentyl)aminomethyl]dihydrospectinomycin pentatrimethylsilyl derivative $C_{48}H_{83}N_3O_{12}Si_5$. Calc'd: 1033.4823. Found: 1033.4807.

EXAMPLE 71

3'-(R)-3'-(acetylaminomethyl)-dihydrospectinomycin dihydrochloride

Refer to Chart F.

To a solution of 205 mg (0.30 mmol) of the title product of Example 70 in 5 ml of methanol is added 200 mg of palladium black and 0.11 ml (3.0 mmol) of formic acid. The mixture is stirred 30 min at room temperature, filtered and concentrated in vacuo. The residue is dissolved in 5 ml of $H_2O$, treated with 0.6 ml (0.6 mmol) of 1.0N HCl and lyophilized to afford 200 mg of white solid: $^{13}C$—NMR ($D_2O$, $CH_3CN$ internal reference) $\delta$ 175.5, 94.3, 93.4, 76.1, 70.5, 68.7, 66.9, 65.9, 62.4, 60.5, 59.2, 42.6, 39.1, 31.9, 31.3, 22.8, and 21.0; MS exact mass for hexatrimethylsilyl derivative $C_{35}H_{79}N_3O_8Si_6$. Calc'd: 837.4483. Found: 837.4472.

EXAMPLE 72

3'-(R)-3'-[N-glycylaminomethyl]-dihydrospectinomycin trihydrochloride

Refer to Chart F.

A. To a solution of 185 mg (0.29 mmol) of N,N'-dibenzyloxycarbonyl-3'-(R)-3'-aminomethyldihydrospectinomycin (Example 52) in 10 ml dry tetrahydrofuran is added 60 mg (0.29 mmol) of N-benzyloxycarbonylglycine, 60 mg (0.29 mmol) of dicyclohexylcarbodiimide and 10 mg (0.08 mmol) of 4-dimethylaminopyridine. The mixture is stirred 5 hr at room temperature, concentrated in vacuo and partitioned between 100 ml of ethyl acetate and 10 ml of $H_2O$. The ethyl acetate layer is dried with brine and $MgSO_4$ and concentrated in vacuo to give 230 mg of white solid. The product is chromatographed on 20 g of 230–400 mesh silica gel packed with 1% methanol/chloroform and eluted with 500 ml of 1%, 500 ml of 2%, and 1 l of 2.5% methanol/chloroform. The pure fractions, as determined by TLC on silica gel (10% methanol/chloroform, $R_f=0.32$) are pooled to afford 112 mg (0.14 mmol, 47%) of the product as a white solid: $^{13}C$—NMR ($d_6$-acetone) $\delta$ 171.0, 158.0, 138.2, 128.6, 128.5, 128.3, 95.1, 93.3, 75.8, 74.5, 67.3, 67.0, 66.5, 66.4, 60.5, 57.5, 45.0, 42.4, 39.7, 31.8, and 21.4; MS (tetrakistrimethylsilyl derivative) 1110, 1095, 1002, 987, 889, 818, 745, 493, 449, 359, 329, 305, 257, 91; exact mass, for M+, $C_{53}H_{82}N_4O_{14}Si_4$. Calc'd: 1110.4904. Found: 1110.4841.

B. To a solution of 110 mg (0.13 mmol) of the reaction product of part A in 5 ml of methyl alcohol is added 100 mg of palladium black and 50 $\mu$l (1.34 mmol) of formic acid. The mixture is stirred 35 min at room temperature, filtered and concentrated in vacuo. The residue is dissolved in 5 ml of $H_2O$, treated with 0.45 ml (0.45 mmol) of 1N HCl and lyophilized to give 70 mg (0.12 mmol, 92%) of title product as a white solid: $^{13}C$—NMR ($D_2O$, $CH_3CN$ internal reference) $\delta$ 168.3, 94.4, 93.5, 76.0, 70.7, 68.8, 67.0, 66.1, 62.6, 60.6, 59.4, 42.6, 41.6, 39.3, 32.0, 31.4, and 21.1; MS exact mass for M+ $-CH_3$ for heptatrimethylsilyl derivative, $C_{38}H_{88}N_4O_8Si_7$. Calc'd: 924.4987. Found: 924.4989.

EXAMPLE 73

3'-(R)-3'-[N-(pyrolle-2-carbonyl)aminomethyl]-dihydrospectinomycin dihydrochloride.

Refer to Chart F.

A. To a solution of 631 mg (1.0 mmol) of N,N'-dibenzyloxycarbonyl-3'-(R)-3'-aminomethyldihydrospectinomycin (Example 52) in 20 ml of dry tetrahydrofuran stirred at room temperature with a nitrogen atmosphere is added 216 mg (1.05 mmol) of dicyclohexylcarbodiimide, 10 mg (0.08 mmol) of 4-dimethylaminopyridine and 111 mg (1.0 mmol) of pyrolle-2-carboxylic acid. The mixture is stirred 2 hr at room temperature and 4 equivalents of each of the last three reactants are added. After 2 hr stirring, the mixture is concentrated in vacuo, diluted with 200 ml of EtOAc and extracted with 50 ml of 5% $NaHCO_3$. Some insoluble material is removed with the aqueous layer. The EtOAc solution is washed with 5% $NaHCO_3$ and brine and dried with $MgSO_4$. Concentration in vacuo affords 1.43 g of brown gum.

The product is chromatographed on 140 g of 230–400 mesh silica gel pcked with 1% methanol/chloroform and eluted with 1 l of 1% methanol/chloroform and the remainder 2% methanol/chloroform collecting 45 ml fractions. Fractions 105–154 are pooled to afford 252 mg (0.35 mmol, 35%) of the product as a white solid: $^{13}C$—NMR ($d_6$-acetone) $\delta$ 162.8, 157.0, 138.2, 129.1, 128.4, 126.6, 122.6, 111.0, 110.0, 95.2, 93.4, 76.1, 74.5, 67.4, 66.5, 65.6, 60.0, 57.8, 55.4, 42.5, 40.0, 31.8, and 21.4; MS for pentatrimethylsilyl ether 1084, 1069, 997, 889, 799, 339, 195, 166, 91; exact mass for $C_{51}H_{84}N_4O_{12}Si_5$. Calc'd: 1084.4932. Found, 1084.4927.

B. To a solution of 240 mg (0.33 mmol) of the reaction product of part A in 5 ml of methanol is added 200 mg of palladium black and 0.125 ml (3.3 mmol) of formic acid. The mixture is stirred 30 min at room temperature, filtered and concentrated in vacuo. The residue is dissolved in 5 ml of $H_2O$, treated with 0.66 ml (0.66 mmol) of 1N HCl and lyophilized to afford 174 mg of the title product as a white solid: $^{13}C$—NMR ($D_2O$, $CH_3CN$ internal reference) $\delta$ 164.3, 125.4, 124.2, 113.0, 110.8, 94.4, 93.7, 76.6, 70.7, 68.9, 67.1, 66.1, 62.6, 60.6, 59.4, 42.6, 39.3, 32.0, 31.4, and 21.4; MS exact mass for heptatrimethylsilyl ether $C_{41}H_{88}N_4O_8Si_7$. Calc'd: 960.4987. Found, 960.4982.

EXAMPLE 74

N,N'-dibenzyloxycarbonyl-3'-(R)-3'-(succinylaminomethyl) dihydrospectinomycin (Formula LXXXVIII: $R_{45}$ is —$CH_2CH_2COOH$)

Refer to Chart F.

In 0.5 ml of methanol are combined 100 mg (0.15 mmol) of N,N'-dibenzyloxycarbonyl-3'-(R)-3'-(aminomethyl) dihydrospectinomycin (Example 52), 16.5 mg (0.165 mmol) of succinic anhydride and 23 $\mu$l (0.165 mmol) of triethylamine. The solution is stirred for 1 hr and concentrated in vacuo. The residue is partitioned between ethyl acetate and water. The water is acidified with concentrated hydrochloric acid and the ethyl acetate is separated. After extracting a second time with ethyl acetate, the extracts are combined, washed with brine, and dried over magnesium sulfate. After filtering, the solvent is removed in vacuo to afford 100 mg of a white solid (91.2% yield): $^{13}C$—NMR ($d_6$-acetone) 174.5, 173.5, 157.5, 138.3, 129.2, 128.5, 128.3, 95.3, 93.4, 76.0, 74.8, 74.5, 67.9, 67.4, 66.4, 65.4, 60.5, 60.4, 57.6, 42.7, 39.8, 31.8, 30.8, and 21.4 ppm.

EXAMPLE 75

3'-(R)-3'-(succinylaminomethyl)dihydrospectinomycin trihydrochloride

Refer to Chart F.

In 5 ml of methanol is dissolved 80 mg (0.10 mmol) of N,N'-dibenzyloxycarbonyl-3'-(R)-3'-(succinylaminomethyl)dihydrospectinomycin (Example 74). To this solution is added 75 mg of palladium black followed by 27 μl (0.69 mmol) of formic acid. After stirring for 40 min, the reaction is filtered and the solvent is removed in vacuo to afford 63 mg of a white solid. The product is taken up in water and treated with 1 ml of 1N hydrochloric acid. The solution is frozen and lyophilized to afford 58 mg (100% yield) of the title compound as a white solid: $^{13}C$—NMR ($D_2O$) 177.7, 176.2, 94.4, 93.6, 76.4, 70.7, 69.0, 67.0, 66.1, 62.6, 60.6, 59.4, 42.6, 39.0, 32.0, 31.4, 31.2, 30.3, and 21.0 ppm; exact mass calc'd for $C_{40}H_{89}N_3O_{10}Si_7$ (hepta TMS): 967.4933. Found: 967.4953.

EXAMPLE 76

N,N'-di-benzyloxycarbonyl-3'-(S)-3'-(N-ethylaminomethyl) dihydrospectinomycin (Formula LXV: $R_{63}$ is hydrogen and $R_{64}$ is ethyl).

Refer to Chart F.

In 6 ml of MeOH are combined 500 mg (0.774 mmol) of N,N'-dibenzyloxycarbonyl-3'-(S)-3'-(aminomethyl) dihydrospectinomycin (Example 50), 44 μl (0.774 mmol) of acetaldehyde and a trace of methyl orange indicator in MeOH. To this solution is then added 16.2 mg (0.258 mmol, 0.774 mmol $H^-$) of $NaCNBH_3$ in 1 ml of MeOH. The pH is adjusted with the addition of 1N methanolic HCl until the indicator is just pink. The reaction is then stirred at room temperature and additional 1N HCl/MeOH is added to keep the indicator pink. After 2.5 hours the MeOH is removed and the residue partitioned between $H_2O$ and EtOAc. The aqueous phase is extracted again with EtOAc (2×30 ml). The combined organics are washed with brine (1×50 ml) and dried over $MgSO_4$. After filtering, the solvent is removed in vacuo to afford 458 mg of a white solid. The product is taken up in $CHCl_3$ and chromatographed on 20 gm of silica gel, slurry packed in $CHCl_3$. The column is eluted as follows: 100 ml, 1% MeOH/$CHCl_3$; 100 ml, 2% MeOH/$CHCl_3$; 100 ml 3% MeOH/$CHCl_3$; 100 ml 5% MeOH/$CHCl_3$; 100 ml 7% MeOH/$CHCl_3$; and 700 ml 10% MeOH/$CHCl_3$. In elution volume 520–720 ml there is contained 306 mg of the title compound as a white solid (60% yield): $^{13}C$—NMR ($d_6$-acetone) 138.1, 129.1, 128.3, 94.2, 74.4, 73.1, 67.2, 66.6, 65.1, 57.6, 57.5, 57.3, 55.7, 45.0, 40.3, 31.4, 21.1, and 15.3 ppm; exact mass calc'd for $C_{41}H_{66}N_3O_{11}Si_3$ (tri—OTMS,—$CH_3$) 860.4005, found 860.4008.

EXAMPLE 77

N,N'-di-benzyloxycarbonyl-3'-(S)-3'-(N-butylaminomethyl) dihydrospectinomycin (Formula LXV: $R_{63}$ is hydrogen and $R_{64}$ is n-butyl).

Refer to Chart F.

In 10 ml of MeOH is dissolved 507 mg (0.803 mmol) of N,N'-dibenzyloxycarbonyl-3'-(S)-3'-(aminomethyl) dihydrospectinomycin, Example 50. To this solution is added 0.71 ml (8.0 mmol) of n-butyraldehyde and a drop of methyl orange indicator in MeOH. This is followed by the addition of 17 mg of $NaCNBH_3$ in 1 ml of MeOH. The pH is adjusted to 4 with the addition of 1N HCl/MeOH. The pH is maintained at 4 for 0.5 hr while the reaction is stirred. The MeOH is then removed in vacuo and the residue partioned between EtOAC and $H_2O$. The EtOAC is separated and combined with 1, 25 ml EtOAC extract of the aqueous phase. The combined extracts are washed with 50 ml of brine and dried over $MgSO_4$. After filtering, removal of the solvent affords 616 mg of a white solid. The product is taken up in $CHCl_3$ and chromatographed on 30 g of silica gel, slurry packed in $CHCl_3$. The column is eluted as follows: 100 ml 1% MeOH/$CHCl_3$ 100 ml 2% MeOH/$CHCl_3$; 100 ml 3% MeOH/$CHCl_3$; 100 ml 4% MeOH/$CHCl_3$; 1.3 l 5% MeOH/$CHCl_3$. In elution volution volume 850–1400 ml there is recovered 250 mg of the title compound as a white solid: (45.3% yield): $^{13}C$—NMR ($d_6$-acetone) 138.2, 129.2, 128.4, 94.2, 74.5, 73.1, 67.3, 66.7, 65.2, 57.6, 57.5, 55.9, 50.5, 40.3, 32.5, 31.6, 21.2, 20.9, and 14.2 ppm; exact mass calc'd for $C_{46}H_{78}N_3O_{11}Si_4$ (tetra TMS—$CH_3$) 960.4713, found 960.4722.

EXAMPLE 78

N,N'-di-benzyloxycarbonyl-3'-(S)-3'-(N-octylaminomethyl)dihydrospectinomycin (Formula LXV: $R_{63}$ is hydrogen and $R_{64}$ is n-octyl).

Refer to Chart F.

In 5 ml of MeOH is dissolved 500 mg (0.79 mmol) of N,N'-dibenzyloxycarbonyl-3'-(S)-3'-(aminomethyl)-dihydrospectinomycin, Example 50. To this solution is added 1.23 ml of n-octanal and a drop of methyl orange/MeOH solution. Then 17 mg of $NaCNBH_3$ in 1 ml of MeOH is added. The pH lowered to 4 with 1N HCl/MeOH. The reaction is stirred for 1 hr, maintaining the pH at 4. The MeOH is then removed in vacuo and the residue is taken up in $CHCl_3$. The solution is washed with 50 ml of brine and dried over $MgSO_4$. After filtering, the solvent is removed to afford an oil. The product is taken up in $CHCl_3$ and chromatographed on 30 g of silica, slurry packed in $CHCl_3$. The column is eluted as follows: 200 ml $CHCl_3$; 500 ml 1% MeOH/$CHCl_3$; 1 l 2% MeOH/$CHCl_3$; 500 ml 3% MeOH/$CHCl_3$; 1 l 5% MeOH/$CHCl_3$. In elution volume 1100–1400 ml there is recovered 186 mg of the title compound as a white solid (32% yield): $^{13}C$—NMR ($d_6$-acetone) 138.2, 129.2, 128.4, 94.2, 74.5, 74.2, 74.1, 72.9, 67.3, 66.7, 66.5, 65.2, 61.4, 61.1, 60.6, 60.5, 57.6, 57.4, 55.8, 50.8, 40.4, 32.4, 31.5, 30.8, 30.3, 30.1, 29.9, 27.8, 23.2, 21.2, and 14.3 ppm; exact mass calc'd for $C_{51}H_{89}N_3O_{11}Si_4$ (tetra TMS) 1031.5574, found 1031.5585.

EXAMPLE 79

3'-(S)-3'-(N-ethylaminomethyl)dihydrospectinomycin trihydrochloride

Refer to Chart F.

In 10 ml of MeOH are combined 294 mg (0.44 mmol) of N,N'-dibenzyloxycarbonyl-3'-(S)-3'-(N-ethylaminomethyl)dihydrospectinomycin (Example 76) and 200 mg of Pd black. To this solution is added 170 μl of formic acid. The reaction is stirred for 40 minutes and is filtered. Removal of the solvent in vacuo affords 225 mg of a white solid. The product is dissolved in 2 ml of $H_2O$ and 1.5 ml of 1N HCl is added. The solution is frozen and lyophilized to afford 215 mg of a white solid (97.5% yield): $^{13}C$—NMR ($D_2O$) 96.3, 95.1, 75.5, 74.2, 70.6, 70.5, 70.3, 65.5, 65.0, 62.2, 54.5, 47.6, 41.7, 35.3, 34.6, 23.2, and 13.79 ppm; exact mass calc'd for $C_{35}H_{81}N_3O_7Si_6$ (hexa TMS) 823.4690, found 823.4690.

EXAMPLE 80

3'-(S)-3'-(N-butylaminomethyl)dihydrospectinomycin trihydrochloride

Refer to Chart F.

In 10 ml of MeOH is dissolved 245 mg (0.39 mmol) of N,N'-dibenzyloxycarbonyl-3'-(S)-3'-(N-butylaminomethyl)dihydrospectinomycin (Example 77). To this solution is added 250 mg of Pd black followed by 152 μl of HCOOH. The reaction is stirred for 45 min and is filtered. Removal of the solvent in vacuo affords 195 mg of a white solid. The material is taken up in 2 ml of H$_2$O and 1.5 ml of 1N HCl is added. The solution is frozen and lyophilized to afford 166 mg of a white solid (80% yield): $^{13}$C—NMR (D$_2$O) 96.2, 95.3, 75.6, 73.4, 70.8, 69.7, 69.5, 65.1, 63.9, 61.7, 54.9, 52.4, 41.7, 34.8, 34.6, 30.8, 23.4, 22.9, and 16.6 ppm; exact mass calc'd for C$_{37}$H$_{85}$N$_3$O$_7$Si$_6$ (Hexas—TMS) 851.5003, found 851.4980; exact mass calc'd for C$_{36}$H$_{82}$N$_3$O$_7$Si$_6$ (Hexa-TMS-CH$_3$) 836.4768, found 836.4757.

EXAMPLE 81

3'-(S)-3'-(N-octylaminomethyl)dihydrospectinomycin trihydrochloride

Refer to Chart F.

In 5 ml of MeOH is dissolved 180 mg of N,N'-di-benzyloxycarbonyl-3'-(S)-3'-(N-octylaminomethyl)dihydrospectinomycin (Example 78). To this solution is added 200 mg of Pd black followed by 94 μl of HCOOH. The reaction is stirred for 30 min and is filtered. The solvent is removed in vacuo to afford 150 mg of a white solid. The product is taken up in 2 ml of H$_2$O and 0.8 ml of 1N HCL is added. The solution is frozen and lyophilized overnight to afford 135 mg of a white solid (96% yield): $^{13}$C-NMR (D$_2$O) 96.2, 95.3, 75.6, 73.4, 70.6, 69.7, 69.5, 65.1, 63.9, 61.7, 54.9, 50.7, 41.8, 34.8, 34.6, 32.0, 29.5, 28.8, 25.8, 23.4, and 17.2 ppm; exact mass calc'd for C$_{41}$H$_{93}$N$_3$O$_7$Si$_6$ (hexa TMS) 907.5629, found 907.5618.

EXAMPLE 82

Procedure for the Preparation of 3-(R)-3'-(N-alkylated)dihydrospectinomycins

A. For predominant monoalkylation, N,N'-dibenzyloxycarbonyl-3'-(R)-3'-(aminomethyl)dihydrospectinomycin (Example 52) is dissolved in MeOH. To the solution is added 10 equivalents of the appropriate aldehyde and a trace of methyl orange indicator. The pH is then adjusted to the indicator's endpoint with methanolic HCl and 0.33 equivalents of NaCNBH$_3$ in MeOH is added. The reaction is stirred at room temperature and the pH is maintained near the endpoint of methyl orange by adding additional methanolic HCl. The reaction is easily followed by TLC using Analtech Silica plates and eluting with 10% MeOH/CHCl$_3$/1% NH$_4$OH as a solvent. When the reaction is complete, the solvent is removed in vacuo and the residue is partitioned between H$_2$O and EtOAc. The aqueous phase is made alkaline with the addition of concentrated NH$_4$OH and the EtOAc is separated and combined with an additional EtOAc extract. The combined extracts are washed with brine and dried over MgSO$_4$. The solvent is then removed in vacuo to afford the crude product. The product is taken up in CHCl$_3$ and chromatographed on silica, slurry packed in CHCl$_3$. The column is eluted with a MeOH/CHCl$_3$ gradient (1%–5%), and 50 ml fractions are taken. The fractions are analyzed by TLC and pure fractions are pooled and concentrated in vacuo to afford the product.

B. For predominant dialkylation, the above procedure is followed using 0.66 equivalents of NaCNBH$_3$.

According to the procedure above, there are prepared (a) N,N'-dibenzyloxycarbonyl-3'-(R)-3'-(N-ethylaminomethyl)dihydrospectinomycin: Alkylation of 491 mg (0.78 mmol) of N,N'-dibenzyloxycarbonyl-3'-(R)-3'-(aminomethyl)dihydrospectinomycin affords 123 mg (24% yield) of the title compound after chromatography:
$^{13}$C—NMR (d$_6$-acetone) 138.1, 129.1, 128.3, 128.1, 97.0, 93.8, 74.5, 71.6, 67.1, 66.4, 65.2, 57.6, 54.0, 44.4, 43.8, 31.6, 21.5 and 14.9 ppm; exact mass calc'd for C$_{45}$H$_{77}$N$_3$O$_{11}$Si$_4$ (tetra TMS) 947.4653, found 947.4601.

(b) N,N'-dibenzyloxycarbonyl-3'-(R)-3'-(N-propylaminomethyl)dihydrospectinomycin: Alkylation of 1.7 g (2.7 mmol) of amine affords 1.1 g of the title product after chromatography (61% yield): $^{13}$C—NMR (d$_6$-acetone) 158.0, 157.0, 138.1, 129.1, 128.3, 128.1, 97.1, 93.8, 74.5, 71.6, 67.2, 66.4, 65.2, 57.6, 54.3, 51.5, 48.9, 44.5, 31.8, 31.6, 23.0, 21.5, and 11.9 ppm; exact mass calc'd for C$_{46}$H$_{79}$N$_3$O$_{11}$Si$_4$ (tetra TMS) 961.4791, found 961.4789.

(c) N,N'-dibenzyloxycarbonyl-3'-(R)-3'-(N-pentylaminomethyl)dihydrospectinomycin: Alkylation of 2.0 g (3.16 mmol) of amine affords 653 mg of the title compound after chromatography (29% yield):
$^{13}$C—NMR (d$_6$-acetone) 138.2, 129.1, 128.3, 128.1, 97.1, 93.8, 74.6, 71.7, 67.2, 66.5, 65.2, 61.0, 60.9, 57.7, 54.4, 49.7, 44.5, 31.6, 30.0, 29.7, 23.0, 21.5, and 14.3 ppm; exact mass calc'd for C$_{48}$H$_{83}$N$_3$O$_{11}$Si$_4$ (tetra TMS) 989.5104, found 989.5113.

(d) N,N'-dibenzyloxycarbonyl-3'-(R)-3'-(N-hexylaminomethyl)dihydrospectinomycin: Alkylation of 500 mg (0.79 mmol) of amine using an excess of NaCNBH$_3$ affords a mixture of mono and dialkylated products. The mixture is chromatographed to afford 109 mg (19% yield) of mono alkylated product:
$^{13}$C—NMR (d$_6$-acetone) 138.1, 129.1, 128.3, 128.1, 97.0, 93.8, 74.5, 71.7, 67.2, 66.4, 65.2, 57.6, 54.3, 49.7, 44.4, 32.2, 31.6, 29.9, 27.4, 23.1, 21.5, and 14.2 ppm; exact mass calc'd for C$_{49}$H$_{85}$N$_3$O$_{11}$Si$_4$ (tetra TMS) 1003.5261, found 1003.5278; and 310 mg (49% yield) of dialkylated product: $^{13}$C—NMR (d$_6$-acetone) 138.2, 129.1, 128.7, 128.4, 128.2, 97.2, 93.8, 74.7, 74.4, 72.2, 67.2, 66.5, 65.4, 65.2, 61.0, 60.4, 60.3, 59.7, 57.7, 55.9, 44.6, 32.2, 32.0, 31.8, 31.5, 27.6, 26.9, 23.2, 21.5, and 14.3 ppm; exact mass calc'd for C$_{54}$H$_{94}$N$_3$O$_{11}$Si$_4$ (tetra TMS—CH$_3$) 1072.5965, found 1072.5968.

(e) N,N'-dibenzyloxycarbonyl-3'-(R)-3'-(N-octylaminomethyl)dihydrospectinomycin: Alkylation of 2.3 g (3.6 mmol) of amine affords 1.65 g of the title compound after chromatography (62% yield); $^{13}$C—NMR (d$_6$-acetone) 157.7, 157.6, 138.1, 129.1, 128.3, 128.1, 97.1, 93.7, 74.5, 74.6, 73.8, 71.6, 67.1, 66.4, 65.2, 61.1, 60.9, 60.8, 57.6, 54.4, 49.7, 44.5, 32.4, 31.6, 30.0, 29.8, 27.8, 23.2, 21.5, and 14.3 ppm; exact mass calc'd for C$_{50}$H$_{86}$N$_3$O$_{11}$Si$_4$ (tetra TMS—CH$_3$) 1016.5339, found 1016.5327.

(f) N,N'-dibenzyloxycarbonyl-3'-(R)-3'-(N-isobutylaminomethyl)dihydrospectinomycin: Alkylation of 500 mg (0.79 mmol) of amine affords 216 mg of the title compound after chromatography (39.8% yield): $^{13}$C—NMR (d$_6$-acetone): 138.1, 129.1, 128.6, 128.3, 128.1, 97.1, 93.8, 74.5, 71.7, 67.2, 66.4, 65.2, 57.8, 54.6, 44.4, 31.8, 31.6, 28.4, 21.5, 20.9, and 20.8 ppm. Exact mass calc'd for $C_{47}H_{81}N_3O_{11}Si_4$ (tetra TMS) 975.4948, found 975.4943.

(g) N,N'-dibenzyloxycarbonyl-3'-(R)-3'-[N-(2-methyl butyl)aminomethyl]dihydrospectinomycin: Alkylation of 2.0 g (3.16 mmol) of amine affords 478 mg of the title compound after chromatography (21.6% yield): $^{13}C$—NMR (d$_6$-acetone) 138.2, 129.1, 128.4, 128.2, 97.1, 93.8, 74.6, 71.6, 67.2, 66.5, 65.3, 61.1, 61.0, 60.3, 57.7, 56.0, 54.8, 44.6, 35.0, 31.6, 28.0, 26.7, 21.6, 17.9, and 11.5 ppm; exact mass calc'd for $C_{47}H_{80}N_3O_{11}Si_4$ (tetra TMS—CH$_3$) 974.4870, found 974.4859.

(h) N,N'-dibenzyloxycarbonyl-3'-(R)-3'-[N-cyclohexylmethyl)aminomethyl]dihydrospectinomycin: Alkylation of 2.47 g (3.9 mmol) of amine affords 982 mg of the title compound as a white solid (30.6% yield): $^{13}C$—NMR (d$_6$-acetone) 138.1, 129.1, 128.3, 97.0, 93.7, 74.5, 71.7, 67.2, 66.5, 65.2, 57.6, 56.5, 54.6, 44.5, 38.0, 31.9, 31.6, 27.2, 26.5, and 21.5 ppm; exact mass calc'd for $C_{50}H_{85}N_3O_{11}Si_4$ (tetra TMS) 1015.5261, found 1015.5240.

(i) N,N'-dibenzyloxycarbonyl-3'-(R)-3'-[N-(cyclooctylmethyl)-aminomethyl]dihydrospectinomycin: Alkylation of 1.5 gm (2.27 mmol) of amine affords 729 mg of the title compound. Also recovered is 503 mg of unreacted amine. The yield of the title compound based on recovered amine is 61.3%: $^{13}C$—NMR (d$_6$-acetone) 138.3, 129.1, 128.4, 128.2, 97.2, 93.8, 74.6, 71.8, 67.1, 67.0, 66.5, 65.3, 61.1, 61.0, 60.2, 57.7, 57.3, 54.7, 44.6, 37.7, 31.6, 31.5, 31.2, 27.7, 27.0, 26.1, 26.0 and 21.5 ppm; exact mass calc'd for $C_{51}H_{86}N_3O_{11}Si_4$ (tetra TMS—CH$_3$) 1028.5339, found 1028.5255.

(j) N,N'-dibenzyloxycarbonyl-3'-(R)-3'-[N,N-(dicyclohexylmethyl)aminomethyl]dihydrospectinomycin: Dialkylation of 634 mg (1.0 mmol) of amine affords 173 mg of the title compound (21% yield): $^{13}C$—NMR (d$_6$-acetone) 129.1, 128.4, 128.2, 97.3, 93.5, 74.7, 72.9, 67.4, 67.2, 66.5, 65.1, 61.2, 57.7, 57.6, 57.4, 44.6, 36.5, 32.6, 32.4, 31.7, 27.2, 26.7, and 21.4 ppm; exact mass calc'd for $C_{53}H_{86}N_3O_{11}Si_3$ (tri TMS—CH$_3$) 1024.5570, found 1024.5526.

(k) N,N'-dibenzyloxycarbonyl-3'-(R)-3'-(N,N-diisobutylaminomethyl)dihydrospectinomycin: Dialkylation of 631 mg (1 mmol) of amine affords 171 mg of the title compound as a white solid (23% yield): $^{13}C$—NMR (d$_6$-acetone) 138.1, 129.1, 128.3, 128.1, 97.0, 93.5, 74.6, 73.1, 67.3, 67.2, 66.4, 65.2, 61.1, 57.5, 44.1, 31.4, 26.8, 21.7, and 21.4 ppm; exact mass calc'd for $C_{48}H_{81}N_3O_{11}Si_4$ (tri—TMS) 959.5179, found, 959.5134.

EXAMPLE 83

Deprotection of N,N'-dibenzyloxycarbonyl-3'-(R)-3'-N-mono and N,N-dialkylaminomethyl dihydrospectinomycins The protected substrate is dissolved in MeOH and an equivalent weight of Pd black is added. To this mixture is added 10 equivalents of formic acid. The reaction is stirred for 45 min, filtered and concentrated to dryness. The residue is taken up in H$_2$O and 3.5 equivalents of 1N HCl are added. The solution is frozen and lyophilized to afford the final product.

Accordingly, the products of Example 82 yield:

(a) 3'-(R)-3'-(N-ethylaminomethyl)dihydrospectinomycin trihydrochloride: Deprotection of 123 mg (0.19 mmol) affords 83 mg (89% yield) of the title compound: $^{13}C$—NMR (D$_2$O) 94.0, 93.2, 73.2, 70.4, 68.2, 66.8, 66.2, 62.4, 60.5, 59.3, 50.5, 45.1, 40.7, 31.9, 31.5, 21.0, and 11.1 ppm; exact mass calc'd for $C_{35}H_{81}N_3O_{11}Si_6$ (hexa TMS) 823.4690, found 823.4665.

(b) 3'-(R)-3'-(N-propylaminomethyl)dihydrospectinomycin trihydrochloride: Deprotection of 1.1 gm (1.6 mmol) affords 0.68 gm of the title compound as a white solid (82.8% yield): $^{13}C$-NMR (D$_2$O) 94.1, 93.3, 73.3, 70.5, 68.2, 66.9, 66.2, 62.5, 60.6, 59.3, 51.2, 51.0, 41.0, 32.0, 31.6, 21.0, 19.5, and 11.2 ppm; exact mass calc'd for $C_{36}H_{80}N_3O_7Si_6$ (hexa TMS) 837.4846, found 837.4867.

(c) 3'-(R)-3'-(N-pentylaminomethyl)dihydrospectinomycin trihydrochloride: Deprotection of 650 mg (0.92 mmol) affords 573 mg of the title compound as a white solid: $^{13}C$—NMR (D$_2$O) 94.3, 93.5, 73.4, 70.9, 68.4, 67.1, 66.5, 62.7, 60.9, 59.6, 51.2, 49.8, 41.2, 31.9, 31.5, 28.9, 25.6, 22.5, 21.1, 20.8, and 14.2 ppm; exact mass calc'd for $C_{38}H_{87}N_3O_7Si_6$ (hexa TMS) 865.5159, found 865.5167.

(d) 3'-(R)-3'-(N-hexylaminomethyl)dihydrospectinomycin trihydrochloride: Deprotection of 87 mg (0.12 mmol) afforded 58 mg (87% yield) of the title compound as a white solid: $^{13}C$—NMR (D$_2$O) 94.1, 93.3, 73.2, 70.5, 68.3, 66.9, 66.2, 62.5, 60.6, 59.3, 51.0, 49.8, 40.9, 31.9, 31.5, 31.4, 26.3, 25.8, 22.7, 21.0, and 14.3 ppm; exact mass calc'd for $C_{39}H_{89}N_3O_7Si_6$ (hexa—TMS) 879.5316, found 879.5303.

(e) 3'-(R)-3'-(N-octylaminomethyl)dihydrospectinomycin trihydrochloride: Deprotection of 1.65 g (2.2 mmol) affords 1.12 g of the title compound as a white solid (87% yield): $^{13}C$—NMR (D$_2$O) 94.0, 93.2, 73.2, 70.4, 68.2, 66.8, 66.2, 62.4, 60.5, 59.2, 50.9, 49.7, 32.1, 31.9, 31.5, 29.3, 26.8, 25.8, 23.0, 20.9, and 14.5 ppm; exact mass calc'd for $C_{41}H_{93}N_3O_{11}Si_6$ (hexa TMS) 907.5629, found 907.5627.

(f) 3'-(R)-3'-(N-isobutylaminomethyl)dihydrospectinomycin trihydrochloride: Deprotection of 216 mg (0.29 mmol) affords 152 mg (90% yield) of the title compound as a white solid: $^{13}C$—NMR (D$_2$O) 93.9, 93.3, 73.0, 70.3, 68.1, 66.8, 66.1, 62.3, 60.5, 59.2, 56.3, 51.3, 41.2, 31.8, 31.4, 25.5, 21.0, 19.9, and 19.7 ppm; exact mass calc'd for $C_{37}H_{85}N_3O_7Si_6$ (hexa TMS) 851.5003, found 851.5020.

(g) 3'-(R)-3'-[N-(2-methylbutyl)aminomethyl]dihydrospectinomycin trihydrochloride: Deprotection of 478 mg (0.68 mmol) affords 338 mg of the title compound as a white solid (87% yield): $^{13}C$—NMR (D$_2$O) 94.0, 93.4, 73.0, 70.4, 68.2, 66.8, 66.2, 62.4, 60.5, 59.3, 55.1, 51.6, 51.5, 41.3, 31.8, 31.7, 31.5, 27.1, 21.0, 16.9, and 11.1 ppm; exact mass calc'd for $C_{38}H_{87}N_3O_7Si_6$ (hexa TMS) 865.5159, found 865.5150.

(h) 3'-(R)-3'-[N-(cyclohexylmethyl)aminomethyl]dihydrospectinomycin trihydrochloride: Deprotection of 928 mg (1.12 mmol) affords 640 mg of the title compound as a white solid (86% yield): $^{13}C$—NMR (D$_2$O) 94.2, 93.5, 73.2, 70.6, 68.3, 66.9, 66.3, 62.5, 60.6, 59.4, 55.3, 51.5, 41.3, 34.6, 31.9, 31.5, 30.7, 26.5, 25.9 and 21.0 ppm; eact mass calc'd for $C_{40}H_{89}N_3O_7Si_6$ (hexa TMS) 891.5316, found 891.5324.

(i) 3'-(R)-3'-[N-(cyclooctylmethyl)aminomethyl]dihydrospectinomycin trihydrochloride: Deprotection of 792 mg (1.04 mmol) affords 550 mg of the title compound as a white solid (88.9% yield): $^{13}C$—NMR (D$_2$O, as the triformate) 94.4, 93.6, 73.2, 70.8, 68.4, 67.0, 66.4, 62.7, 60.8, 59.6, 55.9, 51.8, 41.7, 34.6, 31.9, 31.5, 30.0, 27.5, 26.8, 25.4 and 21.1 ppm; exact mass calc'd for $C_{42}H_{93}N_3O_7Si_6$ (hexa—TMS) 919.5629, found 919.5656.

(j) 3'-(R)-3'-(N,N-dihexylaminomethyl)dihydrospectinomycin trihydrochloride: Deprotection of 220 mg (0.28 mmol) affords 157 mg (88% yield) of the title compound as a white solid: $^{13}C$—NMR ($D_2O$) 94.1, 93.3, 70.5, 68.3, 68.1, 66.7, 66.6, 66.5, 66.3, 62.4, 60.5, 5trihydrochloride: Deprotection of 220 mg (0.28 mmol) affords 157 mg (88% yield) of the title compound as a white solid: $^{13}C$—NMR ($D_2O$) 94.1, 93.3, 70.5, 68.3, 68.1, 66.7, 66.6, 66.5, 66.3, 62.4, 60.5, 59.3, 56.9, 56.7, 31.9, 31.5, 26.3, 23.7, 22.8, 21.0 and 14.4 ppm; exact mass calc'd for $C_{42}H_{93}N_3O_7Si_6$ (hexa TMS) 891.5860, found 891.5853.

(k) 3'-(R)-3'-[N,N-(dicyclohexylmethyl)aminomethyl]dihydrospectinomycin trihydrochloride: Deprotection of 149 mg (0.18 mmol) affords 124 mg of the title compound as a white solid (100% yield):

$^{13}C$—NMR ($D_2O$) 94.3, 93.8, 73.2, 70.5, 68.2, 66.9, 66.5, 65.2, 64.5, 62.6, 60.7, 59.5, 43.2, 34.1, 33.7, 31.9, 31.8, 31.3, 30.9, 30.7, 26.5, 25.9 and 21.1 ppm; exact mass calc'd for $C_{41}H_{85}N_3O_7Si_4$ (tetra TMS) 843.5465, found 843.5459.

(l) 3'-(R)-3'-(N,N-diisobutylaminomethyl)dihydrospectinomycin trihydrochloride: Deprotection of 153 mg (0.20 mmol) affords 96 mg of the title compound (82% yield: $^{13}C$—NMR ($D_2O$) 94.3, 93.9, 73.3, 70.6, 68.2, 66.7, 66.6, 65.7, 62.6, 60.7, 59.6, 43.3, 31.9, 31.8, 31.6, 25.1, 24.8, 21.1, 21.0, 20.6, 20.4, 19.8 and 19.6 ppm; exact mass calc'd for $C_{38}H_{85}N_3O_7Si_5$ (penta—TMS) 835.5234, found 835.5241.

The hydrogenation and isomerization processes illustrated in Chart F can be carried out at any temperature at which reactants will be sufficiently soluble, in the solvent being used, at which reactants and products will not thermally decompose and at which the reaction will proceed at a rate acceptable to the person using the process. A person of ordinary skill can easily ascertain the limit of the temperature ranges for any combination of reactants for any solvent, base or basic ion-exchange resin and product. The preferred range is 20°–30° C.

The isomerization reaction illustrated in Chart F is catalyzed by base or basic ion-exchange resin.

In both the hydrocyanation and the isomerization, preferred bases, if used, are triethylamine and potassium or sodium carbonate. Preferred ion-exchange resin, if such resin is used, is Amberlite® IRA-45 available from the Rohm and Haas Co. of Philadelphia, Pa. Most preferred in the isomerization reaction from 3'(R) to 3'(S) epimer and the hydrocyanation process wherein more of the 3'(S) epimer than of the 3'(R) epimer is desired, is potassium carbonate as base and methanol as solvent.

Most preferred in the hydrocyanation reaction when more of the 3'(R) epimer than of the 3'(S) epimer is desired, is use of Amberlite® IR-45 resin with methanol as solvent and at least a two-fold molar excess of acetone cyanohydrin as source of cyano groups.

Removal of basic ion-exchange resin, or its neutralization with acid, or neutralization of base, if only base is used, slows the R to S isomerization drastically. "Quenching" means slowing sufficiently to permit the isolation of the R epimer and its stabilization by, for example, further reaction, before the ratio of the amount of R epimer to the amount of S epimer becomes less than 1.

Whenever synthetic methods disclosed herein result in two or more compounds related as stereoisomers, such compounds will also be related as diasteriomers and consequently will have differing physical and chemical properties. These differing properties can be used to separate the stereoisomers from each other by any of numerous techniques known to the skilled in the art.

As used in the present specification:

"Basic ion-exchange resin" is ion-exchange resin wherein the ion-exchange groups are basic in character, i.e., acceptor of protons from or donors of electron pairs to compounds which pass or diffuse through the resin. Examples of basic ion-exchange resins wherein the ion-exchange groups are tertiary amino groups include the following:

Amberlite® IRA-45, IRA-68, IRA-93, and IRA-94, and

Amberlyst® A-21, all available from the Rohm and Haas Co. of Philadelphia, Pa.;

Dowex® 3-X'4, available from the Dow Chemical Co. of Midland, Mich.; and

Dudlite® A-2, A-6, A-4F and A-7 available from the Diamond Shamrock Corp. of Cleveland, Ohio.

"Halogen" means fluorine, chlorine, bromine or iodine.

"Mcg" means "microgram"

A compound which is a "source of cyano groups" means any compound which, under the basic reaction conditions, in the unreactive solvent employed in the hydrocyanation reaction illustrated in Chart F, will produce by, for example, decomposition or dissociation, a cyano group which can react with the 3' carbon of the spectinomycin or spectinomycin-analog starting material. Preferred source of cyano groups is acetone cyanohydrin.

FORMULAS

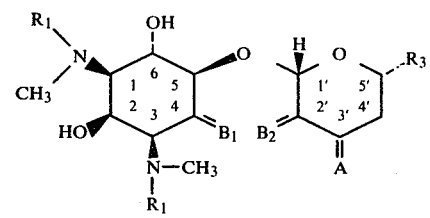

I

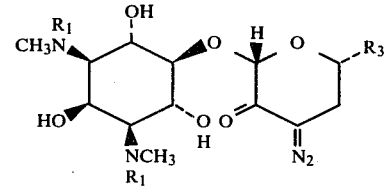

II

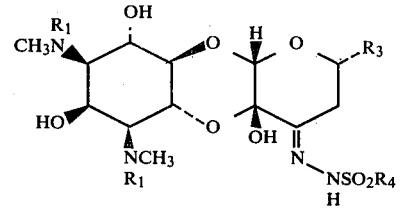

III

FORMULAS

FORMULAS

CHART A

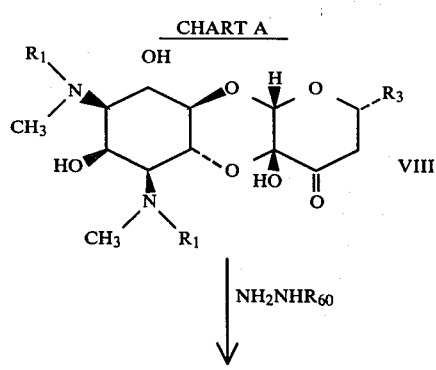

VIII

↓ NH$_2$NHR$_{60}$

CHART A

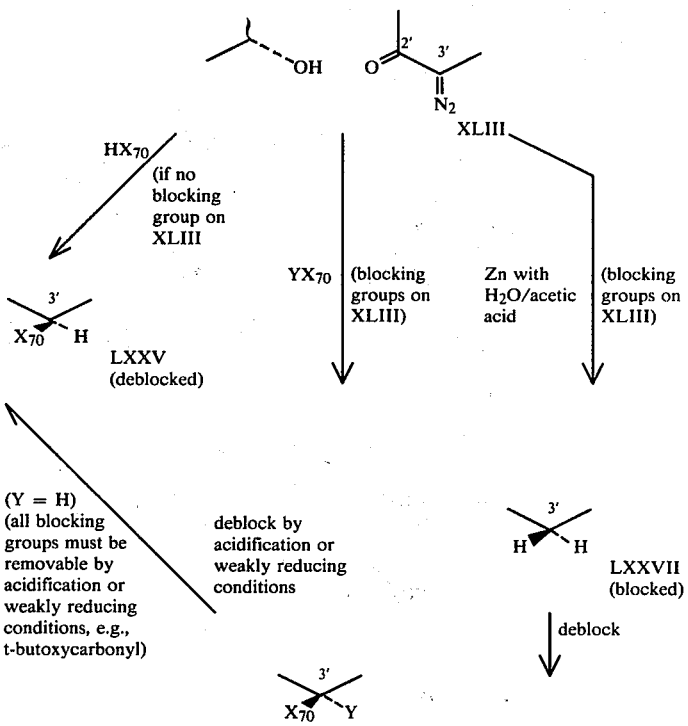

XLII (R$_{60}$ = H) transition metal oxide oxidizing agent (e.g. MnO$_2$, Ag$_2$O, HgO)

(R$_{60}$ = —S(O)$_2$—R$_4$) base

XLIII

CHART B

XLIII

HX$_{70}$ (if no blocking group on XLIII)

YX$_{70}$ (blocking groups on XLIII)

Zn with H$_2$O/acetic acid (blocking groups on XLIII)

LXXV (deblocked)

(Y = H) (all blocking groups must be removable by acidification or weakly reducing conditions, e.g., t-butoxycarbonyl)

deblock by acidification or weakly reducing conditions

LXXVII (blocked)

↓ deblock

CHART B
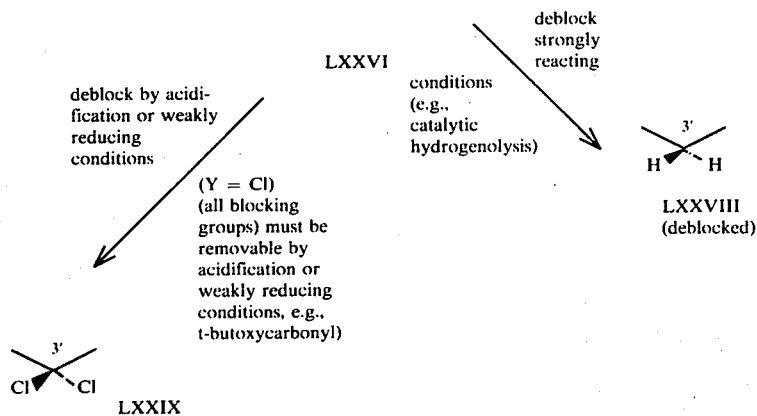
CHART C
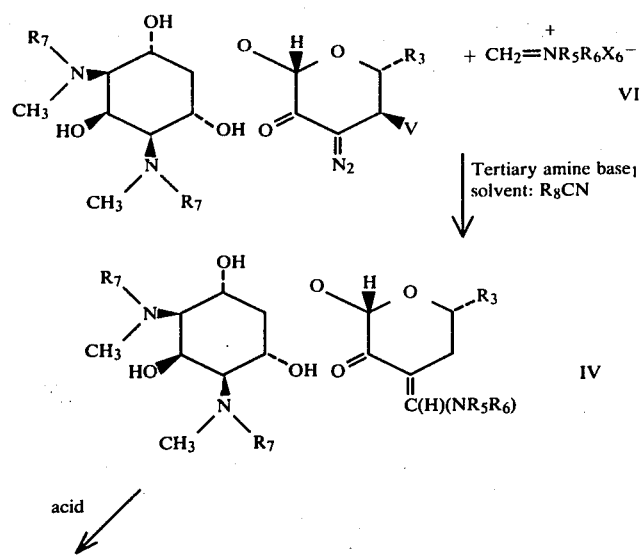

CHART C
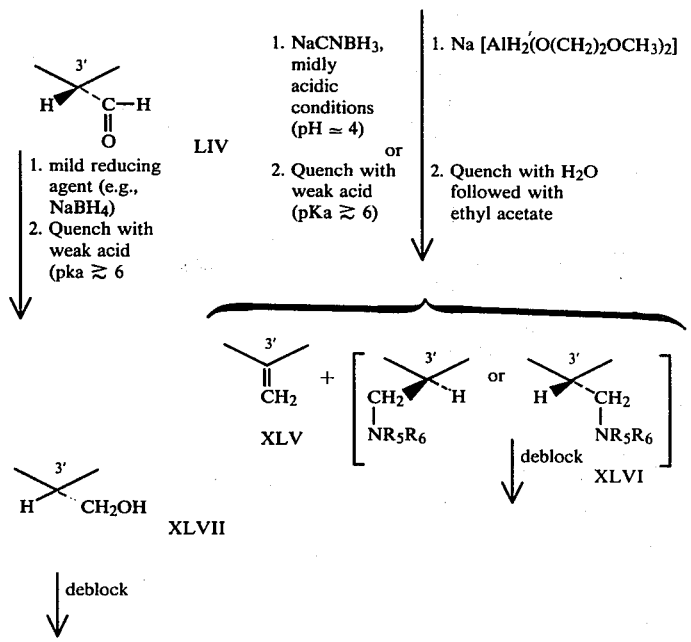
CHART D
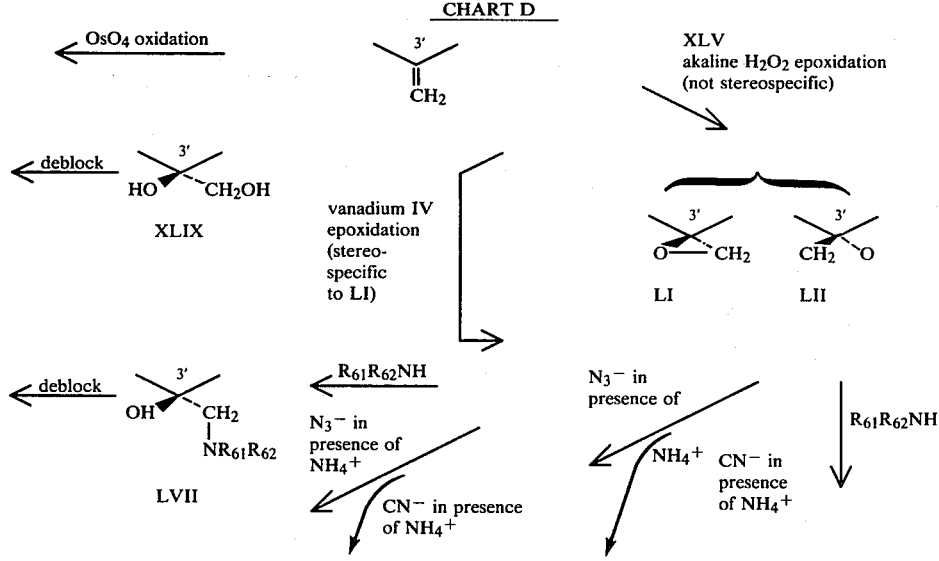

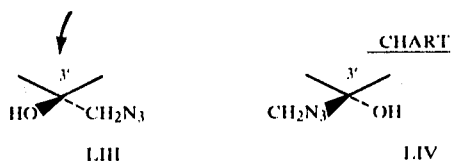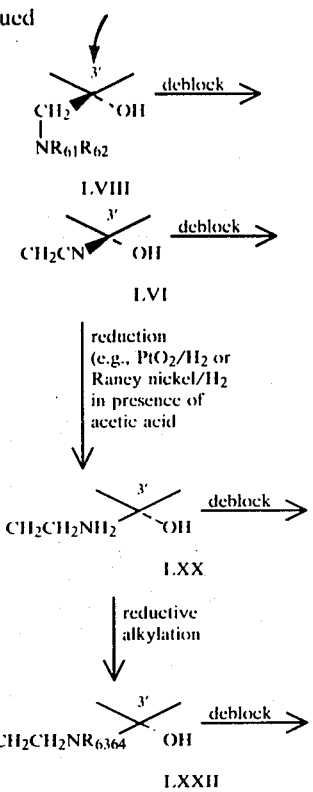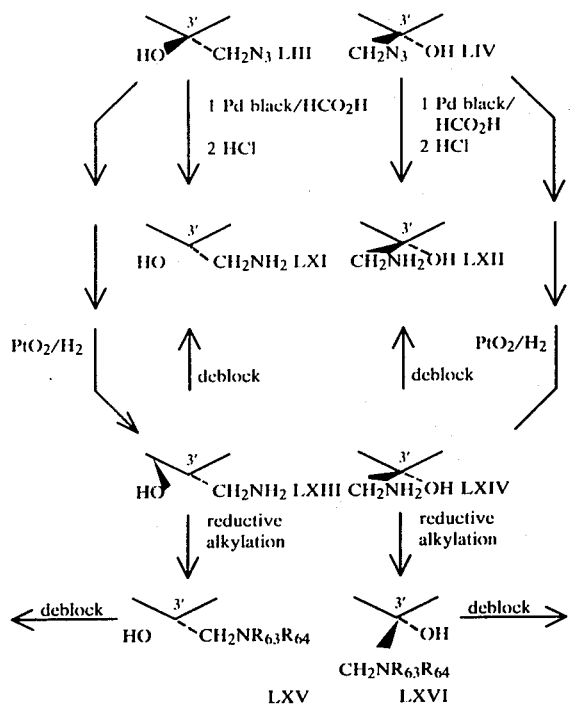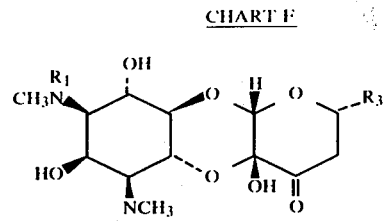

-continued
CHART F $$\xleftarrow{\text{deblock}} \underset{\underset{NH-CO-R_{45}}{|}}{\overset{HO}{\underset{LXXXVII}{\bigwedge}} \overset{3'}{\underset{CH_2}{\bigvee}}} \xrightarrow{\text{acylation}} \underset{\underset{NH-CO-R_{45}}{|}}{\overset{3'}{\underset{CH_2}{\bigvee}} \overset{OH}{\underset{LXXXVIII}{\bigwedge}}} \xrightarrow{\text{deblock}}$$

What is claimed is:

1. A compound of formula I,

[structure diagram]

wherein $R_1$ is
(a) hydrogen or
(b) a blocking group;
wherein $R_3$ is
(a) hydrogen
(b) alkyl of 1 to 8 carbon atoms, inclusive,
(c) $-R_{31}-O-R_{32}$, wherein $R_{31}$ is alkylene of 1 to 4 carbon atoms, inclusive, and $R_{32}$ is hydrogen or alkyl of 1 to 6 carbon atoms, inclusive, with the proviso that the sum of the number of carbon atoms in $R_{31}$ and the number of carbon atoms in $R_{32}$ is less than or equal to 7,
(d) $-R_{31}-NR_{33}R_{34}$, wherein $R_{31}$ is as defined above, wherein $R_{33}$ is hydrogen or alkyl of 1 to 6 carbon atoms, inclusive, and $R_{34}$ is hydrogen, alkyl of 1 to 6 carbon atoms, inclusive, or a blocking group, with the proviso that if $R_{34}$ is not a blocking group, the sum of the number of carbon atoms in $R_{31}$ and the number of carbon atoms in whichever of $R_{33}$ or $R_{34}$ has the larger number of carbon atoms is less than or equal to 7, or
(e) alkyl of 1 to 4 carbon atoms, inclusive, substituted with 1, 2, or 3 halogen atoms;
wherein A is
(a) $=N_2$,
(b) $\alpha-H:\beta-H$,
(c) $\alpha-H:\beta-X$, wherein X is chlorine or bromine, i.e., the configuration at C-3' is (R),
(d) $\alpha-Cl:\beta-Cl$,
(e) $=CH(NR_5R_6)$, with the proviso that
  (i) $R_1$ is a blocking group and
  (ii) $R_{34}$ is not hydrogen and, if $R_{33}$ is hydrogen, $R_{34}$ is a blocking group, and wherein $R_5$ and $R_6$, being the same or different, are alkyl of 1 to 6 carbon atoms, inclusive, and wherein the configuration at the vinylogous carbon bonded to C-3' is, with respect to C-2', E or Z, but not both,
(f) $\alpha-CHO:\beta-H$, i.e., the configuration at C-3' is (R), with the proviso that
  (i) $R_1$ is a blocking group and
  (ii) $R_{34}$ is not hydrogen and, if $R_{33}$ is hydrogen, $R_{34}$ is a blocking group,
(g) methylene ($=CH_2$), with the proviso that
  (i) $R_1$ is a blocking group and
  (ii) $R_{34}$ is not hydrogen and, if $R_{33}$ is hydrogen, $R_{34}$ is a blocking group,
(h) $\alpha-CH_2OH:\beta-H$, i.e., the configuration at C-3' is (R),
(i) $\alpha-H:\beta-CH_2NR_5R_6$ or $\alpha-CH_2NR_5R_6:\beta-H$, i.e., the configuration at C-3' is (R) or (S) but not both,
(j) $\alpha-CH_2OH:\beta-OH$, i.e., the configuration at C-3' is (S),
(k) epoxymethano ($-O-CH_2-$ or $-CH_2-O-$), with the proviso that
  (i) $R_1$ is a blocking group and
  (ii) $R_{34}$ is not hydrogen and, if $R_{33}$ is hydrogen, $R_{34}$ is a blocking group,
(l) $\alpha-OH:\beta-CH_2N_3$ or $\alpha-CH_2N_3:\beta-OH$, i.e., the configuration at C-3' is (R) or (S), with the proviso that
  (i) $R_1$ is a blocking group and
  (ii) $R_{34}$ is not hydrogen and, if $R_{33}$ is hydrogen, $R_{34}$ is a blocking group,
(m) $\alpha-OH:\beta-(CH_2)_m-CN$ or $\alpha-(CH_2)_m-CN:\beta-OH$, wherein m is 0 or 1, i.e., the configuration at C-3' is (R) or (S),
(n) $\alpha-OH:\beta-(CH_2)_p-NR_{41}R_{42}$ or $\alpha-(CH_2)_p-NR_{41}R_{42}:\beta-OH$, wherein p is 1 or 2, and $R_{41}$ and $R_{42}$, being the same or different, are
  (i) hydrogen
  (ii) alkyl of 1 to 12 carbon atoms, inclusive,
  (iii) aryl of 6 to 12 carbon atoms,
  (iv) aralkyl of 7 to 12 carbon atoms, inclusive, optionally substituted by one or two
    (1) fluoro, chloro or iodo,
    (2) $-NR_{46}R_{47}$, wherein $R_{46}$ and $R_{47}$ are hydrogen or alkyl of one to 6 carbon atoms, inclusive, being the same or different,
    (3) cyano,
    (4) hydroxy,
    (5) carboxy,
    (6) alkoxycarbonyl of 2 to 5 carbon atoms, inclusive, or
    (7) alkoxy of one to 4 carbon atoms, inclusive,
  (v) $-R_{43}-R_{44}$, wherein $-R_{43}-$ is a single bond or $R_{43}$ is alkylene of 1 to 4 carbon atoms, inclusive, and $R_{44}$ is cycloalkyl of 3 to 10 carbon atoms, inclusive, or
  (vi) $-CO-R_{45}$, wherein $R_{45}$ is
  (a) alkyl of one to 12 carbon atoms, inclusive, or aryl or aralkyl of 7 to 12 carbon atoms optionally substituted by one or two
    (1) fluoro, chloro or iodo,
    (2) $-NR_{46}R_{47}$, wherein $R_{46}$ and $R_{47}$ are hydrogen or alkyl of one to 6 carbon atoms, inclusive, being the same or different,
    (3) cyano,
    (4) hydroxy,
    (5) carboxy,
    (6) alkoxycarbonyl of 2 to 5 carbon atoms, inclusive, or
    (7) alkoxy of one to 4 carbon atoms, inclusive,
  (b) $-R_{43}-R_{44}$ wherein $R_{43}$ and $R_{44}$ are as defined above, or
  (c) pyridyl, piperazyl, pyrollyl or morpholinyl optionally substituted by
    (1) fluoro, chloro or iodo,
    (2) $-NR_{46}R_{47}$, wherein $R_{46}$ and $R_{47}$ are hydrogen or alkyl of one to 6 carbon atoms, inclusive, being the same or different,
    (3) cyano, (4) hydroxy,
(5) carboxy,
(6) alkoxycarbonyl of 2 to 5 carbon atoms, inclusive, or
(7) alkoxy of one to 4 carbon atoms, inclusive;
and wherein $B_1$ is $\alpha$—OH:$\beta$—H and $B_2$ is oxo, when A is =$N_2$ or =CH(NR$_5$R$_6$), or $B_1$ is $\alpha$—$B_3$:$\beta$—H and $B_2$ is $\alpha$—$B_4$:$\beta$—OH wherein $B_3$ and $B_4$ are taken together to form oxa (—O—), when A is not =$N_2$ or =CH(NR$_5$R$_6$); or the pharmacologically acceptable acid addition salts thereof when $R_1$ and $R_{34}$ are not blocking groups and A is not =$N_2$.

2. A compound according to claim 1 selected from the group consisting of:

3'-chloro-3'-deoxo-N,N'-di-tert-butoxycarbonyl spectinomycin;

3'-bromo-3'-deoxo-N,N'-di-tert-butoxycarbonyl spectinomycin;

3'-deoxo-N,N'-di-tert-butoxycarbonyl-3',3'-dichlorospectinomycin;

3'-chloro-3'-deoxospectinomycin dihydrochloride;

3'-bromo-3'-deoxospectinomycin dihydrochloride;

3',3'-dichloro-3'-deoxospectinomycin dihydrochloride;

3'-(dimethylamino)methylene-N,N'-dicarbobenzyloxyseco-spectinomycin;

N,N'-dicarbobenzyloxy-3'-deoxo-3'-formylspectinomycin;

N,N'-dicarbobenzyloxy-3'-deoxo-3'-(hydroxymethyl)spectinomycin;

3'-deoxo-3'-(hydroxymethyl)spectinomycin;

N,N'-dicarbobenzyloxy-3'-deoxo-3'-methylenespectinomycin;

N,N'-dibenzyloxycarbonyl-3'-deoxo-3'-(N,N-dimethylaminomethyl)dihydrospectinomycin;

N,N'-dicarbobenzyloxy-3'-(hydroxymethyl)dihydrospectinomycin;

3'-(hydroxymethyl)dihydrospectinomycin dihydrochloride;

N,N'-dibenzyloxycarbonyl-3'-deoxo-3'-(N,N-dimethylaminomethyl)spectinomycin;

3'-deoxo-3'-(N,N-dimethylaminomethyl)spectinomycin trihydrochloride;

N,N'-dibenzyloxycarbonyl-3'-deoxo-3'-methylenespectinomycin oxide;

N,N'-dibenzyloxycarbonyl-3'-azidomethyldihydrospectinomycin;

3-S-3'-aminomethyldihydrospectinomycin trihydro

3'-(cyanomethyl)dihydrospectinomycin dihydrochloride;

N,N'-dibenzyloxycarbonyl-3-(S)-3'-aminomethyldihydro-spectinomycin;

N,N'-dibenzyloxycarbonyl-3'-(R)-3'-aminomethyldihydro-spectinomycin;

N,N'-dibenzyloxycarbonyl-3'-(R)-3'-(N-ethylaminomethyl)dihydrospectinomycin;

N,N'-dibenzyloxycarbonyl-3'-(R)-3'-(N-octylaminomethyl)dihydrospectinomycin;

3'-(R)-3'-(N-ethylaminomethyl)dihydrospectinomycin trihydrochloride;

3'-(R)-3'-(N-octylaminomethyl)dihydrospectinomycin trihydrochloride;

N,N'-dibenzyloxycarbonyl-3'-(S)-3'-(N-ethylaminomethyl)-dihydrospectinamycin;

3'-(S)-3'-(N-ethylaminomethyl)dihydrospectinomycin trihydrochloride;

N,N'-dibenzyloxycarbonyl-3'-(S)-3'-(N-butylaminomethyl)dihydrospectinomycin;

3'-(S)-3'-(N-butylaminomethyl)dihydrospectinomycin trihydrochloride;

N,N'-dibenzyloxycarbonyl-3'-(S)-3'-(N-octylaminomethyl)dihydrospectinomycin;

3'-(S)-3'-(N-octylaminomethyl)dihydrospectinomycin trihydrochloride;

3'-(R)-3'-aminomethyldihydrospectinomycin trihydrochloride;

3'-(S)-3'-(n-propylaminomethyl)-3'-dihydrospectinomycin trihydrochloride;

3'-R-3'-[(3-dimethylaminopropyl)-aminomethyl]-dihydrospectinomycin tetrahydrochloride;

N,N'-dicarbobenzyloxy-3'-(R)-3'-(n-butylaminomethyl)-3'-dihydrospectinomycin;

3-(R)-3'-(n-butylaminomethyl)-3'-dihydrospectinomycin trihydrochloride;

N,N'-dibenzyloxycarbonyl-3'-(S)-3'-(aminomethyl)-dihydrospectinomycin;

N,N'-dibenzyloxycarbonyl-3'-(R)-spectinomycin cyanohydrin;

N,N'-dibenzyloxycarbonyl-3'-(R)-3'-(aminomethyl)-dihydrospectinomycin;

N,N'-dibenzyloxycarbonyl-3'-(R)-3'-(N-hexylaminomethyl)-dihydrospectinomycin;

N,N'-dicarbobenzyloxy-3'-(N,N-dihexylaminomethyl)-dihydrospectinomycin;

N,N'-dibenzyloxycarbonyl-3'-(R)-3'-(N-isobutylaminomethyl)-dihydrospectinomycin;

3'-(N,N-diisobutylaminomethyl)-dihydrospectinomycin;

N,N'-dibenzyloxycarbonyl-3'-(R)-3'-(N-cyclohexylmethyl-aminomethyl)-dihydrospectinomycin;

N,N'-dibenzyloxycarbonyl-3'-(R)-3'-[N,N-di(cyclohexylmethyl)amino-methyl]-dihydrospectinomycin;

3'-(R)-3'-(N-hexylaminomethyl)-dihydrospectinomycin trihydrochloride;

3'-(R)-3'-(N-isobutylaminomethyl)-dihydrospectinomycin trihydrochloride;

3'-(R)-3'-(N-cyclohexylmethylaminomethyl)-dihydrospectinomycin trihydrochloride;

3'-(R)-3'-(N,N-dihexylaminomethyl)-dihydrospectinomycin trihydrochloride;

3'-(R)-3'-(N,N-diisobutylaminomethyl)-dihydrospectinomycin trihydrochloride;

3'-(R)-3'-(N,N-di[cyclohexylmethyl]aminomethyl)-dihydro-spectinomycin trihydrochloride;

N,N'-dibenzyloxycarbonyl-3'-(R)-3'-(cyclopentylaminomethyl)dihydrospectinomycin;

N,N'-dibenzyloxycarbonyl-3'-(R)-3'-(cyclohexylaminomethyl)dihydrospectinomycin;

N,N'-dibenzyloxycarbonyl-3'-(R)-3'-(cycloheptylaminomethyl)dihydrospectinomycin;

3'-(R)-3'-(cyclopentylaminomethyl)dihydrospectinomycin trihydrochloride;

3'-(R)-3'-(cyclohexylaminomethyl)dihydrospectinomycin trihydrochloride;

3'-(R)-3'-(cycloheptylaminomethyl)dihydrospectinomycin trihydrochloride;

N,N'-dibenzyloxycarbonyl-3'-(R)-3'-[(2-hydroxyethyl)aminomethyl]dihydrospectinomycin;

N,N'-dibenzyloxycarbonyl-3'-(R)-3'-[(5-hydroxylpentyl)aminomethyl]dihydrospectinomycin;

N,N'-dibenzyloxycarbonyl-3'-(R)-3'-[(6-chlorohexyl)aminomethyl]dihydrospectinomycin;

N,N'-dicarbobenzyloxy-3'-(R)-3'-[carbomethoxymethyl)aminomethyl]dihydrospectinomycin;

3'-(R)-3'-[(2-hydroxyethyl)aminomethyl]dihydrospectinomycin trihydrochloride;

3′-(R)-3′-[(5-hydroxypentyl)aminomethyl]dihydrospectinomycin trihydrochloride;
3′-(R)-3′-[(6-chlorohexyl)aminomethyl]dihydrospectinomycin trihydrochloride;
3′-(R)-3′-[(carbomethoxymethyl)aminomethyl]dihydrospectinomycin trihydrochloride;
N,N′-dibenzyloxycarbonyl-3′-(R)-3′-[(benzyloxycarbonylmethyl)aminomethyl]dihydrospectinomycin;
3′-(R)-3′-[(carboxymethyl)aminomethyl]dihydrospectinomycin trihydrochloride;
N,N′-dibenzyloxycarbonyl-3′-(R)-3′-(N-acetylaminomethyl)dihydrospectinomycin;
3′-(R)-3′-(acetylaminomethyl)-dihydrospectinomycin dihydrochloride;
3′-(R)-3′-[N-glycylaminomethyl]-dihydrospectinomycin trihydrochloride;
3′-(R)-3′-[N-(pyrolle-2-carbonyl)aminomethyl]-dihydrospectinomycin dihydrochloride;
N,N′-dibenzyloxycarbonyl-3′-(R)-3′-(succinylaminomethyl)dihydrospectinomycin;
3′-(R)-3′-(succinylaminomethyl)dihydrospectinomycin trihydrochloride;
N,N′-di-benzyloxycarbonyl-3′-(S)-3′-(N-ethylaminomethyl)dihydrospectinomycin;
N,N′-di-benzyloxycarbonyl-3′-(S)-3′-(N-butylaminomethyl)dihydrospectinomycin;
N,N′-di-benzyloxycarbonyl-3′-(S)-3′-(N-octylaminomethyl)dihydrospectinomycin;
3′-(S)-3′-(N-ethylaminomethyl)dihydrospectinomycin-trihydrochloride;
3′-(S)-3′-(N-butylaminomethyl)dihydrospectinomycin-trihydrochloride;
3′-(S)-3′-(N-octylaminomethyl)dihydrospectinomycin-trihydrochloride;
N,N′-dibenzyloxycarbonyl-3′-(R)-3′-(N-ethylaminomethyl)dihydrospectinomycin;
N,N′-dibenzyloxycarbonyl-3′-(R)-3′-(N-propylaminomethyl)dihydrospectinomycin;
N,N′-dibenzyloxycarbonyl-3′-(R)-3′-(N-pentylaminomethyl)dihydrospectinomycin;
N,N′-dibenzyloxycarbonyl-3′-(R)-3′-(N-hexylaminomethyl)dihydrospectinomycin;
N,N′-dibenzyloxycarbonyl-3′-(R)-3′-(N-octylaminomethyl)dihydrospectinomycin;
N,N′-dibenzyloxycarbonyl-3′-(R)-3′-(N-isobutylaminomethyl)dihydrospectinomycin;
N,N′-dibenzyloxycarbonyl-3′-(R)-3′-[N-(2-methylbutyl)aminomethyl]dihydrospectinomycin;
N,N′-dibenzyloxycarbonyl-3′-(R)-3′-[N-cyclohexylmethyl)aminomethyl]dihydrospectinomycin;
N,N′-dibenzyloxycarbonyl-3′-(R)-3′-[N-cyclooctylmethyl)aminomethyl]dihydrospectinomycin;
N,N′-dibenzyloxycarbonyl-3′-(R)-3′-[N,N-(dicyclohexylmethyl)aminomethyl]dihydrospectinomycin;
N,N′-dibenzyloxycarbonyl-3′-(R)-3′-(N,N-diisobutylaminomethyl)dihydrospectinomycin;
3′-(R)-3′-(N-ethyl-aminomethyl)dihydrospectinomycin trihydrochloride;
3′-(R)-3′-(N-propyl-aminomethyl)dihydrospectinomycin trihydrochloride;
3′-(R)-3′-(N-pentyl-aminomethyl)dihydrospectinomycin trihydrochloride;
3′-(R)-3′-(N-hexyl-aminomethyl)dihydrospectinomycin trihydrochloride;
3′-(R)-3′-(N-octyl-aminomethyl)dihydrospectinomycin trihydrochloride;
3′-(R)-3′-(N-isobutyl-aminomethyl)dihydrospectinomycin trihydrochloride;
3′-(R)-3′-[N-(2-methylbutyl)aminomethyl]dihydrospectinomycin trihydrochloride;
3′-(R)-3′-[N-(cyclohexylmethyl)aminomethyl]dihydrospectinomycin trihydrochloride;
3′-(R)-3′-[N-(cyclooctylmethyl)aminomethyl]dihydrospectinomycin trihydrochloride;
3′-(R)-3′-(N,N-dihexylaminomethyl)dihydrospectinomycin trihydrochloride;
3′-(R)-3′-[N,N-(dicyclohexylmethyl)aminomethyl]-dihydrospectinomycin trihydrochloride; and
3′-(R)-3′-(N,N-diisobutylaminomethyl)dihydrospectinomycin trihydrochloride.

3. A compound of claim 1 wherein A is α—OH:-β—$(CH_2)_m$—CN or α—$(CH_2)_m$—CN:β—OH wherein m is 0 or 1.

4. A compound of claim 1 wherein A is α—OH:-β—$(CH_2)_p$—$NR_{41}R_{42}$ or α—$(CH_2)_p NR_{41}R_{42}$:β—OH wherein p, $R_{41}$ and $R_{42}$ have the meanings defined in claim 2.

5. A compound of claim 2 which is N,N′-dibenzyloxycarbonyl-3′-(R)-3′-aminomethyldihydrospectinomycin.

6. A compound of claim 2 which is 3′-(R)-3′-(N-pentylaminomethyl)dihydrospectinomycin trihydrochloride.

* * * * *

UNITED STATES PATENT AND TRADEMARK OFFICE
CERTIFICATE OF CORRECTION

PATENT NO. : 4,465,848　　　　　　　　　　　　　　　Page 1 of 3

DATED : August 14, 1984

INVENTOR(S) : R.C. Thomas and E.L. Fritzen

It is certified that error appears in the above-identified patent and that said Letters Patent is hereby corrected as shown below:

Column 20, line 3: "200-500" should read --200-550--.
Column 20, line 39: "602," should read --60.2,--.
Column 21, line 35: "($CH_3$'s)" should read --($CH_3N$'s)--.
Column 23, line 30: "(55)" should read --(55%)--.
Column 27, line 30: "66.859.3, 37.8," should read --66.8, 65.9, 62.4, 61.6, 59.3, 37.8,--.
Column 36, line 60: "66.2," should read --65.2,--.
Column 40, line 2: "methyl" should read --ethyl--.
Column 41, line 5: "methyl9-" should read --methyl)- --.
Column 42, line 46 and 47: "methyl9-" should read --methyl)- -- (and) "trichloride" should read --trihydrochloride--.
Column 44, lines 8-9: "cycloalkylablack are combined" should read --cycloalkylaminomethyl)-dihydrospectinomycin (Example 58) and an equal weight of palladium black are combined--.
Column 45, line 35: "62.3, 57.3, 57.6," should read --62.3, 57.6,--.
Column 47, line 48: "60.51," should read --60.5,--.
Column 57, lines 3,4,5,6: "60.5, 5trihydrochloride: Deprotection of 220 mg... (repeated from Column 56, line 68) (Lines 4,5,6 & 7 of Column 57 should be deleted thru 60.5)" should read --60.5, 59.3, 56.9, 56.7, 31.9, 31.5, 26.3, 23.7, 22.8, 21.0 and 14.4--.

UNITED STATES PATENT AND TRADEMARK OFFICE
CERTIFICATE OF CORRECTION

PATENT NO. : 4,465,848

DATED : August 14, 1984

INVENTOR(S) : R.C. Thomas and E.L. Fritzen

It is certified that error appears in the above-identified patent and that said Letters Patent is hereby corrected as shown below:

Column 59 (Structure VII) line 35: " 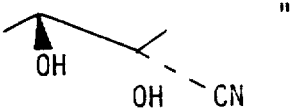 "

should read --  --.

Column 61 (between lines 5-10): "FORMULAS" may be deleted. (Formula XXXI completes Formulas at end of Column 60.)

Column 61, line 20: " 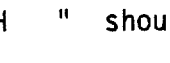 " should read -- 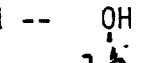 --.

Column 62, (Chart B): " 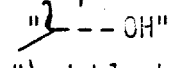 " should read -- 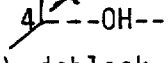 --.

Column 64 (Chart B): "\deblock   should read --\deblock
                       \strongly                \strongly
                       \reacting"               \reducing--.

Columns 63 & 64 (Chart C): " 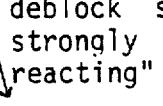 " should read -- 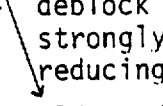 --.

and " 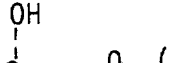 " should read -- 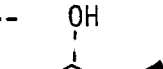 --.

Column 66 (LII): "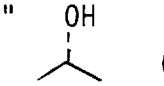" should read ----.

UNITED STATES PATENT AND TRADEMARK OFFICE
CERTIFICATE OF CORRECTION

PATENT NO. : 4,465,848

DATED : August 14, 1984

INVENTOR(S) : R.C. Thomas and E.L. Fritzen

It is certified that error appears in the above-identified patent and that said Letters Patent is hereby corrected as shown below:

Column 71, line 48: "trihydro" should read --trihydrochloride; and line 3 should read --N,N'-dibenzyloxycarbonyl-3'-(cyanomethyl)-dihydrospectinomycin;--.

Signed and Sealed this

Twentieth Day of September, 1988

Attest:

DONALD J. QUIGG

*Attesting Officer*   *Commissioner of Patents and Trademarks*